United States Patent [19]
Alberts et al.

[11] Patent Number: 5,635,506
[45] Date of Patent: Jun. 3, 1997

[54] 1,2-DIHYDRO-3H-DIBENZISOQUINOLINE-1, 3-DIONE ANTICANCER AGENTS

[75] Inventors: David S. Alberts; Robert T. Dorr; William A. Remers; Salah M. Sami, all of Tucson, Ariz.

[73] Assignee: Research Corporation Technologies, Inc., Tucson, Ariz.

[21] Appl. No.: 142,283

[22] PCT Filed: Sep. 13, 1993

[86] PCT No.: PCT/US93/08640

§ 371 Date: Nov. 18, 1993

§ 102(e) Date: Nov. 18, 1993

[87] PCT Pub. No.: WO94/06771

PCT Pub. Date: Mar. 31, 1994

Related U.S. Application Data

[63] Continuation-in-part of Ser. No. 943,634, Sep. 11, 1992, abandoned, which is a continuation-in-part of Ser. No. 803,314, Dec. 4, 1991, abandoned, which is a continuation of Ser. No. 543,596, Jun. 26, 1990, abandoned.

[51] Int. Cl.$^6$ .......... A61K 31/435; C07D 221/18; C07D 411/06; C07D 413/06
[52] U.S. Cl. .......... 514/232.8; 514/253; 514/254; 514/280; 514/284; 544/125; 544/361; 546/58; 546/59; 546/76
[58] Field of Search .......... 544/125, 361; 546/58, 59, 76; 514/232.1, 253, 254, 280, 284

[56] References Cited

U.S. PATENT DOCUMENTS

| | | | |
|---|---|---|---|
| 1,253,252 | 1/1918 | Kardos et al. | 546/76 |
| 1,892,241 | 12/1932 | Kranzlein et al. | 546/58 |
| 3,940,398 | 2/1976 | Wade et al. | 514/241 |
| 4,665,071 | 5/1987 | Zee-Cheng et al. | 514/232.8 |

FOREIGN PATENT DOCUMENTS

| | | |
|---|---|---|
| 0125439 | 11/1984 | European Pat. Off. |
| 2392978 | 7/1974 | France. |
| 92/00281 | 1/1992 | WIPO. |

OTHER PUBLICATIONS

Bergmann, et al., *J. Organic Chemistry*, 23, 907–908 (1958).
Sami, et al., *J. Med. Chem.*, 36, 765–770 (1993).

*Primary Examiner*—Philip I. Datlow
*Attorney, Agent, or Firm*—Scully, Scott, Murphy & Presser

[57] ABSTRACT

This invention relates to a compound useful for the treatment of tumors having the formula:

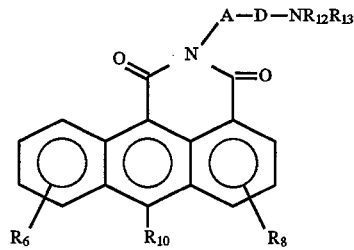

83 Claims, No Drawings

1,2-DIHYDRO-3H-DIBENZISOQUINOLINE-1, 3-DIONE ANTICANCER AGENTS

This is a 371 National Stage Application of International Case PCT/US 93/08640 filed Sep. 13, 1993, which is a continuation in part of U.S. Ser. No. 943,634, filed Sep. 11, 1992, now abandoned which is a continuation in part of U.S. Ser. No. 803,314, filed Dec. 4, 1991, now abandoned, which is a Rule 60 continuation of U.S. Ser. No. 543,596, filed Jun. 26, 1990, now abandoned.

STATEMENT OF THE INVENTION

This invention is directed towards derivatives of azonafide having improved anti-tumor activity.

BACKGROUND OF THE INVENTION

The search for compounds showing anti-tumor activity has, in recent years, included fused ring structures such as derivatives of anthracene, and heterocyclics such as isoquinoline and acridine. The first anthracene derivative to show promise was 2,2'-(9,10 anthracene-dimethylene)bis-(2-thiopseudourea)dihydrochloride, which unfortunately suffered from phototoxicity (U.S. Pat. No. 3,190,795 and Carter, *Cancer Chemother. Rep.*, 1, 153–163, 1968). See also, Frei, E. III, et al., *Cancer Chemother Rep.*, 55, 91–97 (1971). Furthermore, Brana, et al. in *Cancer Chemother Pharmacol*, 4, 61–66 (1980) and in *Eur. J. Med.*, 16, 207–212 (1981) disclose 2- and 5- substituted benz[de]-isoquinoline-1,3-diones having the formula:

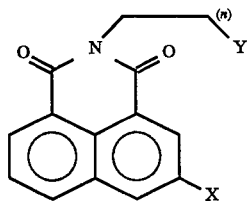

wherein X is H, $NO_2$, $NH_2$, Cl, OH, $NHCO_2Et$, $OCH_3$, $NHCOCH_3$ or t-Bu and Y is a disubstituted amine, OH, $OCH_3$, $CH(CH_3)_2$, SH or $NHCOCH_3$ and n is an integer ranging from zero to three. It is alleged that the compounds therein inhibit HeLa Cells.

Miller, et al. in U.S. Pat. No. 4,108,896 discloses compounds having the formula:

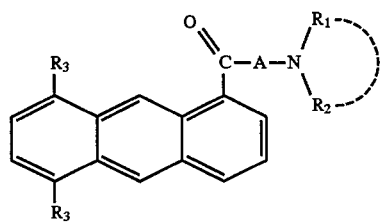

wherein A is a straight or branched alkylene chain having from 1 to 6 carbon atoms; $R_1$ and $R_2$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, or $R_1$ and $R_2$ taken together with the nitrogen atom to which they are attached, represent the pyrrolidinyl, piperidino or morpholino radical; $R_3$ is selected from the group consisting of hydrogen and the radical,

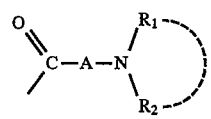

with the proviso that one and only one such R group is hydrogen.

The compounds are disclosed as having use as antiviral agents.

However, the teachings of the references discussed hereinabove are limited to the anthracene and isoquinoline derivatives. None of these references suggest that the dibenzisoquinoline 1,3-diones of the present invention would be useful and effective as anti-tumor agents.

Amonafide (NSC 308847) is an isoquinoline dione derivative having anti-tumor activity. More specifically, amonafide, amino-N-dimethylaminoethylbenz[de]-isoquinoline, has undergone extensive tests for its anti-tumor activity. The National Cancer Institute prepared and distributed a brochure summarizing the anti-tumor activity of amonafide in 1984. Although the level of activity found for amonafide was and continues to be of high interest, this material does have significant deficiencies which indicate the continuing need for agents with improved properties. In the first place, amonafide has produced substantial myelotoxicity leading to some deaths in patients receiving five daily doses of the drug. In addition, this report showed that amonafide had only moderate activity in leukemia models in mice. Also, it showed that amonafide has no activity in human tumor xenografts in mice with colon, lung and mammary cancers. Thus, while amonafide showed significant activity, it does not have a substantially broad spectrum of activity in murine tumor models.

Another group has shown that amonafide or natidimide as poor activity when tested in primary human solid tumors in vitro. See, Ajani, J. A. et al., *Invest New Drugs*, 6, 79–83 (1988).

In view of the shortcomings of these various drugs available heretofore, the present inventors searched for other drugs which were more effective anti-cancer agents. They searched for compounds having the following characteristics:

1) Increased tumor cell cytotoxtc potency;

2) Minimal, if any, cross resistance with multidrug resistant (MDR) tumor cells;

3) Relativity low cytotoxic potency in normal heart cells;

4) Activity in malignant tumors, especially solid tumors, hematological tumors, and leukemia.

As a result of their research, the present inventors have developed compounds meeting these objectives. The present inventors have found that compounds based on anthracene instead of naphthalene show surprising anti-tumor activity.

SUMMARY OF INVENTION

The present invention is directed to 1,2-dihydro-3H-dibenzisoquinoline-1,3-dione derivatives which exhibit anti-tumor activity and are useful as anti-cancer agents.

BRIEF SUMMARY OF THE INVENTION

More particularly, the present invention is directed to compounds of the formula:

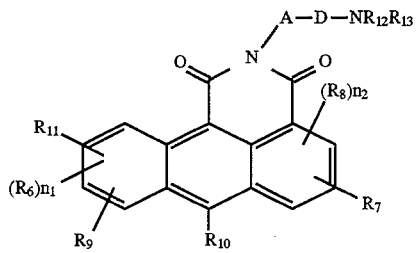

I

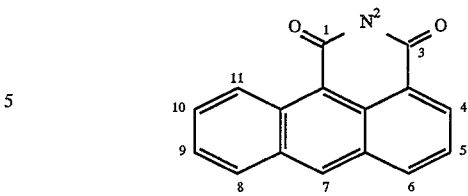

wherein $R_8$, $R_{10}$ and $R_6$ are independently hydrogen, lower alkyl, aryl, lower alkanoyl, formyl, halogen, nitro, heterocyclic lower alkyl, lower alkyl sulfonyl, hydrazino, $NR_2R_3$, $OR_1$, amino-loweralkyleneoxy, monoloweralkylamino-lower alkyleneoxy, diloweralkylaminoloweralkyleneoxy,

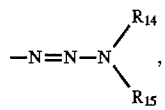

loweralkanoylamino, cyano, $CO_2H$, $CONR_1R_2$, $SO_2NR_1R_2$ or $SR_1$;

$R_1$ is hydrogen, lower alkyl, aryl lower alkyl, aryl, formyl or lower alkanoyl;

$R_2$ and $R_3$ are independently hydrogen, lower alkyl, aryl lower alkyl, aryl, formyl, lower alkanoyl, monoalkyl amino lower alkylene, dialkylamino lower alkylene, or hydroxy lower alkyl, $R_9$, $R_{11}$, and $R_7$ are independently hydrogen or lower alkyl or $R_9$ and $R_{11}$ taken together with the carbon atoms to which they are attached form a phenyl ring, or $R_9$ and $R_{10}$ taken together with the carbon atoms to which they are attached form a phenyl ring or $R_7$ and $R_{10}$ taken together with the carbon atoms to which they are attached form a phenyl ring;

A is $(CR_4R_5)n_3$, lower cycloalkyl, aryl, or a chemical bond, each $R_4$ and $R_5$ are independently hydrogen or lower alkyl;

$R_{12}$ and $R_{13}$ are independently hydrogen or lower alkyl which is unsubstituted or substituted with hydroxy, mercapto, lower alkoxy, lower alkylcarbonyloxy, carboxy or carboloweralkoxy, or $R_{12}$ and $R_{13}$ taken together with the nitrogen atom to which they are attached form a 3 to 6-membered heterocyclic ring;

$R_{14}$ and $R_{15}$ are independently hydrogen or lower alkyl;

D is a chemical bond, or taken together with $NR_{12}$ forms a 5 or 6-membered heterocyclic ring;

$n_1$ and $n_2$ are independently 0, 1, or 2 and $n_3$ is 0, 1, 2, 3, 4 or 5.

These compounds are useful in treating cancer in animals, including mammals by administering to said animals, an effective anti-tumor dose of said compounds.

DETAILED DESCRIPTION OF THE INVENTION

As indicated hereinabove, the present invention is directed to 1,2-dihydro-3H-dibenz(deh)isoquinoline-1,3-dione derivatives. Since the ring structure may have substituents at various positions, to aid in the understanding of the various derivatives, the nomenclature with respect to the dibenzisoquinoline structure is as indicated hereinbelow:

As used herein, the term "alkyl", when used alone or in combination, consists of a carbon chain containing from one to six carbon atoms. The alkyl groups may be a straight chain or a branched chain. It includes such groups as methyl, ethyl, propyl, isopropyl, n-butyl, sec-butyl, iso-butyl, t-butyl, n-pentyl, amyl, n-hexyl, and the like. The preferred alkyl group is methyl.

The term "aryl", when used alone or In combination, consists of an aromatic monocyclic or bicyclic structure having 6 to 10 ring carbon atoms and up to a total of 15 total carbon atoms. It includes such structures as phenyl, α-naphthyl or β-naphthyl. The preferred aryl group is phenyl.

The term "aryl lower alkyl", is an aryl group attached to the dibenzisoquinoline ring through an alkylene group, such as methylene, ethylene, propylene and the like. Examples include benzyl, phenethyl and the like. The preferred aryl lower alkyl group is benzyl.

"Alkylene", as used herein, whether alone or in combination, is an alkyl group attached to the principal chain of the compounds of the present invention through two carbon linkages. This group may be straight chained or branched. It includes such groups as methylene (—$CH_2$—), ethylene (—$CH_2$—$CH_2$—), propylene (—$CH_2$—$CH_2$—$CH_2$—), isopropylene

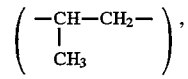

, isobutylene, butylene, sec-butylene, and the like.

As used herein, the term "alkanoyl" is an alkyl group substituted by an oxo group. The oxo group can be substituted at any carbon atom, but it is preferred that it is substituted at the 1-position, i.e., the carbon atoms directly attached to the dibenzisoquinoline ring structure. This group includes acetyl, propanoyl, butanoyl, and the like. The preferred group is acetyl.

Halogen, as used herein, refers to fluorine, chlorine, bromine or iodine.

The term "lower cycloalkyl" refers to a monocyclic alkyl group containing from 3 to 6 ring carbon atoms and up to a total of 10 carbon atoms. This group includes cyclopropyl, cyclobutyl, cyclopentyl, cyclohexyl and the like. The preferred cycloalkyl groups are cyclopentyl and cyclohexyl.

The term "lower alkyl sulfonyl" refers to a lower alkyl group, as defined herein, attached to a sulfonyl, ($SO_2$). Examples include methyl sulfonyl, ethyl sulfonyl, propyl sulfonyl, 1-propyl sulfonyl and the like. The preferred lower alkyl sulfonyl is methyl sulfonyl.

The term "monoalkylamino" refers to an amino group substituted with a lower alkyl group, while "diloweralkylamino" refers to an amino group substituted with two lower alkyl groups.

The term "monoalkylamino lower alkylene" refers to an alkylene group, as defined herein, to which is attached an alkylamino group. Examples include $H_3CHNCH_2CH_2$—,

CH₃CH₂NHCH₂—,

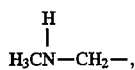

and the like.

"Dialkylamino lower alkylene" refers to an alkylene group, as defined herein, to which is attached a dialkylamino group, such as —CH₂CH₂N(CH₃)₂, —CH₂N(CH₃)₂, —CH₂—CH₂N(C₂H₅)₂, CH₂CH₂N(CH₃)(C₂H₅) and the like. The preferred group is CH₂CH₂N(CH₃)₂.

"Hydroxyloweralkylene amino" refers to an amino group to which is attached a lower alkyl group, as defined herein, and a hydroxy group is substituted on the alkyl group. It is preferred that the hydroxy group is substituted on the omega position.

The term "loweralkyleneoxy" refers to an 0-alkylene group containing 1–6 carbon atoms attached to the polycyclic base structure such as, the dibenzisoquinoline structure, by the oxygen atom. Examples include OCH₂— OCH₂CH₂—, and the like.

The term "aminoloweralkyleneoxy" refers to a lower 0-alkylene group, as defined hereinabove, that bridges an amino group (NH₂) with the polycyclic structure. Examples include OCH₂NH₂, OCH₂CH₂NH₂, and the like.

The term "monoloweralkylaminoloweralkyleneoxy" refers to a lower alkyleneoxy group as defined hereinabove that bridges a loweralkylamino with the polycyclic structure.

Examples include

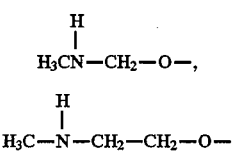

and the like.

The term "diloweralkylaminoloweralkyleneoxy" refers to a lower alkyleneoxy group as defined hereinabove that bridges a loweralkylamino and the polycyclic structure.

Examples include

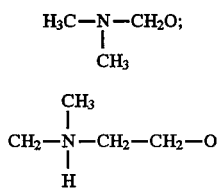

and the like.

The term "loweralkanoylamino" includes such substituents as amino carbonyl bridging the polycyclic structure and an alkyl group. Examples include acetamide, —NH—COC (CH₃)₃, and the like.

The heterocyclic rings as defined herein are 3–6 membered rings containing at least one oxygen, sulfur or nitrogen ring atom and up to a total of 4 ring heteroatoms. It is preferred, however, that there are one or two ring heteroatoms. Especially preferred is one ring heteroatom. The preferred heteroatom is nitrogen. The heterocyclic ring may be completely saturated or partially unsaturated or may be heteroaromatic. It is preferred that the heterocyclic ring contains 5 or 6 ring atoms. Examples include thiophene, furan, pyran, pyrrole, imidazole, pyrazole, pyridine, pyrazine, pyrimidine, pyridazine, isothiazole, furazan, isoxazole, imtdazolidine, imidazoline, pyrazolidine, piperidtne, morpholine, pyrrolidine, tetrahydrofuran, tetrazole, and the like. The preferred heterocyclic groups are piperidino, pyrrolidino, morpholino, pyridyl, piperazino, or imidazolyl, pyridyl, or aziridinyl. The especially preferred heterocyclic groups are piperidino and pyrrolidino.

As indicated in the above formula, the side chain "A—D—NR₁₂R₁₃" is attached to the nitrogen at the 2-position of the dibenzisoquinoline-1,3-diones. This group can be a straight chain, such as (CH₂)n₃NR₁₂R₁₃, wherein n₃ is 1–5 and R₁₂ and R₁₃ are each lower alkyl or hydrogen. Alternatively, R₁₂ and R₁₃ may with the nitrogen to which they are attached from a 3 to 6 membered ring, such as pyrrolidine or piperidine.

In addition, the NR₁₂ group together with D may form a 5 or 6 membered nitrogen heterocyclic ring, such as a piperidtne or pyrrolidine, e.g.,

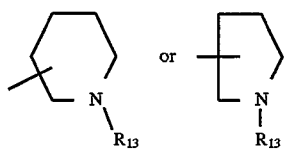

wherein R₁₃ is as defined hereinabove.

The groups R₉ and R₁₀ may together form an aryl ring. For example, if R₉ and R₁₀ form a phenyl ring, the compound of Formula I becomes:

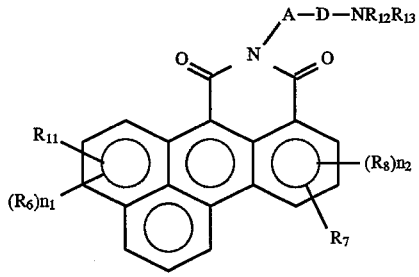

Alternatively, R₁₁ and R₉ may together form an aryl ring, e.g., phenyl ring. Then the compound of Formula I will become:

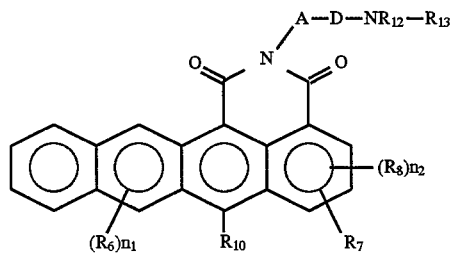

Furthermore, when R₉ and R₁₀ taken together with the carbon atoms to which they are attached form an aryl group, such as phenyl, the compound of Formula I becomes:

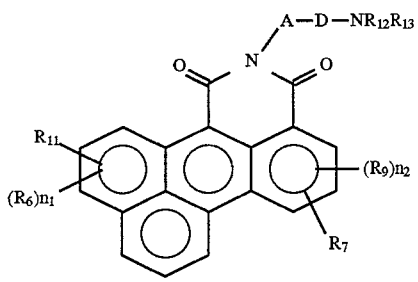

In all of these structures hereinabove, $R_{11}$, $R_6$, $R_9$, $R_{10}$, $R_7$, $R_8$, A, D, $R_{12}$, $R_{13}$, $n_1$ and $n_2$ are as defined hereinabove.

A preferred embodiment of the present invention has the formula:

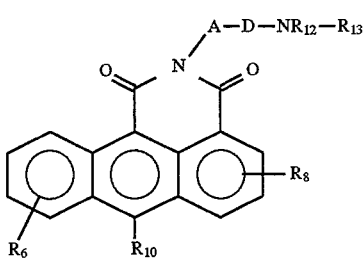

wherein $R_6$, $R_8$, A, D, $R_{12}$ and $R_{13}$ are as defined hereinabove. It is preferred that $R_6$ is hydrogen, nitro, amino, hydroxy, halo, sulfonamido, aminoloweralkanoyl loweralkanoylamino, lower alkyl, diloweralkyltriazino, or lower alkoxy. It is more preferred that $R_6$ is hydrogen, nitro, amino, hydroxy, halo, sulfonamide, aminoloweralkanoyl or lower alkoxy. It is preferred that n is 1.

It is preferred that $R_{10}$ is hydrogen, lower alkyl, halo, hydroxy, lower alkoxy, lower alkylthio, lower alkanoylamino, diloweralkylamino lower alkylene amino, amino or aziridino lower alkylene.

It is also preferred that $R_8$ is hydrogen, lower alkyl, lower alkanoylamino, diloweralkylamino lower alkylene amino, nitro, amino, hydrazino, halo, diloweralkylamino, lower alkylamino, amino lower alkyl hydroxy, lower alkoxy, lower alkylthio, or lower alkyl sulfonyl. It is also preferred that $R_8$ is loweralkanoyl amino, and diloweralkylaminolower alkyleneoxy. It is also preferred that $n_2$ is 1.

In a preferred embodiment, $R_8$, $R_6$ and $R_{10}$ are all hydrogen or two of $R_8$, $R_6$ and $R_{10}$ are hydrogen.

Moreover, it is preferred that $R_6$ is substituted on the 8-, 9, 10- or 11-position of the dibenzisoquinoline-1,3-dione of the present invention.

The preferred $R_1$, $R_2$ and $R_3$ groups are hydrogen or methyl. Therefore, it is preferred that $NR_2R_3$, $OR_1$, and $SR_1$ groups are amino, hydroxy, methoxy, or mercapto, or methylthio.

It is preferred that A is alkylene containing from 1–4 carbon atoms, aryl or a chemical bond. It is especially preferred that the alkylene group is of the formula $(CH_2)n_3$, wherein $n_3$ is 2–3. The preferred aryl group is phenyl.

The most preferred $R_{12}$ and $R_{13}$ groups are lower alkyl or lower alkyl substituted with hydroxy. When $NR_{12}$ does not form a ring with D, it is preferred that the $R_{12}$ and $R_{13}$ groups be the same, or one is hydrogen and the other is lower alkyl, especially methyl. The most preferred $R_{12}$ and $R_{13}$ groups are methyl or $CH_2CH_2OH$. It is most preferred that $ADNR_{12}R_{13}$ is $CH_2CH_2N(CH_3)_2$.

It is preferred that $R_{10}$ is hydrogen, methyl, amino, methoxy, chloro, bromo, or hydroxy.

An especially preferred embodiment of the present invention has the formula:

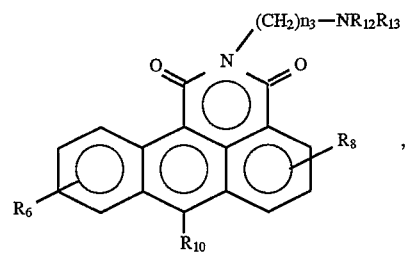

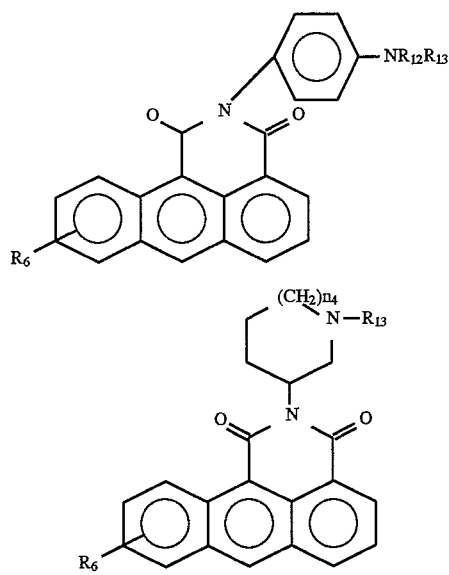

wherein $R_{12}$, $R_{13}$, $n_3$, $R_6$, $R_8$ and $R_{10}$ are as defined hereinabove, and $n_4$ is 0 or 1.

The compounds of the present invention can be prepared by art recognized techniques. More specifically, the compounds of this invention can be prepared by the condensation of anthracene-1,9-dicarboxylic anhydride of formula II, or the corresponding dicarboxylic acid, with an amine of formula $NH_2$—A—D—$NR_{12}R_{13}$ (III) as indicated hereinbelow:

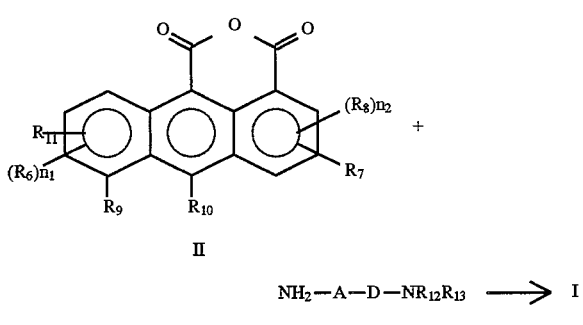

II $NH_2$—A—D—$NR_{12}R_{13}$ $\longrightarrow$ I

III

In the above equation, $R_1$, $R_2$, $R_3$, $R_4$, $R_5$, $R_6$, $R_7$, $R_8$, $R_9$, $R_{10}$, $R_{11}$, $R_{12}$, $R_{13}$, A, D, $n_1$, $n_2$ and $n_3$ are as defined hereinabove.

The reaction is carried out in inert solvents which are inert to both reactants and products and will dissolve both reactants, e.g., toluene, benzene, petroleum ether, hexanes, methylene chloride, chloroform, carbon tetrachloride, alcohol, e.g., methanol, ethanol, and the like. The reaction can be effected at room temperature up to the reflux temperature of the solvent. The preferred solvent is toluene, and it is preferred that the reaction be run at reflux temperatures for a time sufficient for the condensation to occur, e.g., 2–24 hours.

When $R_6$, $R_8$, or $R_{10}$ is halogen, the ether or alcohol groups representative of $R_6$, $R_8$ or $R_{10}$ can be prepared by nucleophilic displacement of said halogen at by strong nucleophiles such as hydroxide and methoxide.

If $R_6$ or $R_8$ is a reactive group, such as $NH_2$, OH, or $SR_1$, it can be protected by blocking groups known in the art. Many of these blocking groups are described in "Protective Groups in Organic Synthesis" by T. W. Greene, John Wiley and Sons, New York, New York, 1981, the contents of which are incorporated herein by reference. For example, when $R_8$ or $R_6$ is $NH_2$, it can be protected by such groups as N-formyl, and N-acetyl, and the like.

Alternatively, these reactive groups can be placed on the rings after the condensation takes place. The following scheme is exemplary:

An exemplary procedure is indicated hereinbelow:

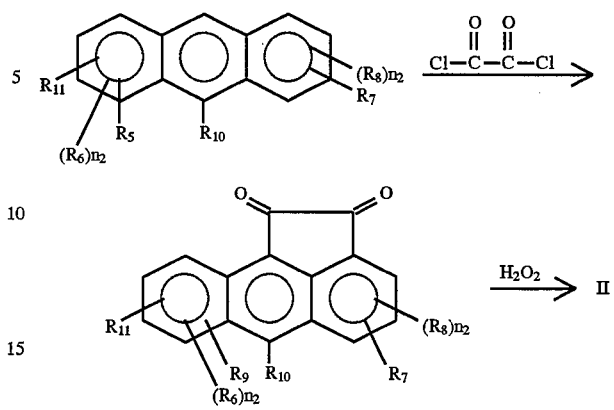

In the above procedure, $R_{11}$, $R_6$, $R_9$, $R_{10}$, $R_9$, $R_8$, $n_1$ and $n_2$ are as defined hereinabove.

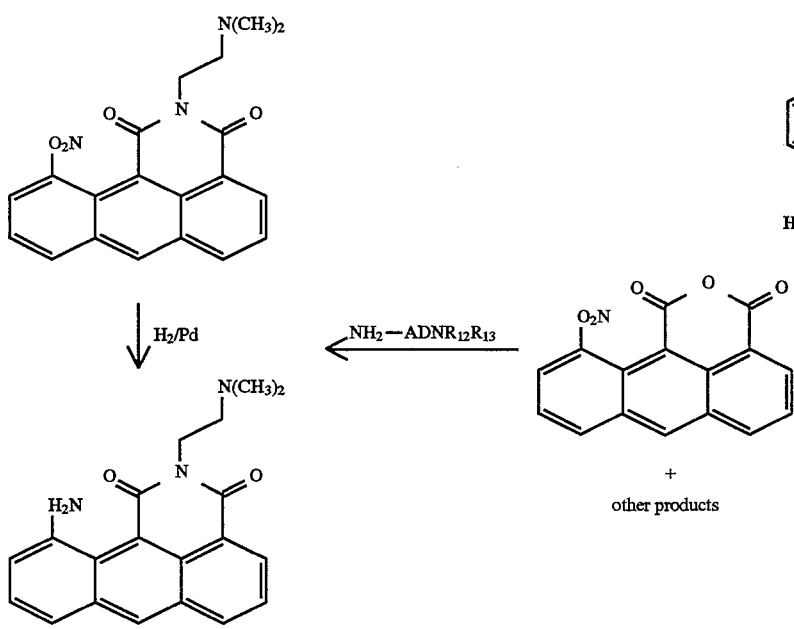

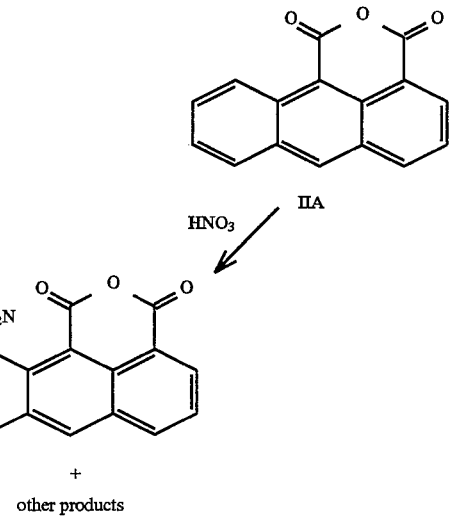

In this scheme, A, D, $R_{12}$ and $R_{13}$ are as defined hereinabove.

The anthracene-1,9-dicarboxylic anhydride (II A) is nitrated with nitric acid, which is then condensed with the amine to form the nitrated dibenz-isoquinoline-1,3-dione derivative. The nitrated compound is then reduced by a reducing agent, such as $H_2$/Pd, or $H_2$/Pt and the like, to form the corresponding amine.

As another example, a compound of Formula I, wherein A, D, $R_1$, $R_2$, $R_3$, $R_4$, $R_5$, $R_7$, $R_8$, $R_9$, $R_{10}$, $R_{11}$, $n_1$, $n_2$ and $n_3$ are as defined hereinabove and $R_6$ is $SO_2NH_2$ can be formed as follows:

A compound of Formula I, wherein A, D, $R_8$, $R_{10}$, $R_1$, $R_2$, $R_3$, $R_9$, $R_{11}$, $R_7$, $R_4$, $R_5$, $R_{12}$ and $R_{13}$ are as defined hereinabove and $R_6$ is hydrogen, is reacted with chlorosulfonic acid ($ClSO_3H$) followed of simple addition by $NR_{12}R_{13}$ to form the above compound.

The anthracene 1,9-dicarboxylic anhydride (II) can also be prepared by art recognized techniques.

The anthracene derivative II is prepared by treating an anthracene with oxalyl chloride, followed by oxidation with hydrogen peroxide in accordance with the procedure described by E. D. Bergmann and R. Ikan, *J. Org. Chem.*, 23, 907 (1958); and then refluxed with acetic anhydride.

When $R_6$, $R_8$, or $R_{10}$ is amino, other groups representative of these positions can be prepared by converting the amino group to a diazonium ion and decomposing this ion under appropriate conditions. For example, diazotization of 9-aminoazonafide followed by heating the diazonium chloride in water affords a mixture of 9-chloroazonafide and 9-hydroxyazonafide.

5-Substituted compounds of formula I can also be prepared from 7-substituted-1,2,3,4-tetrahydroanthracenes. For example, 7-nitro-1,2,3,4-tetrahydroanthracene is reduced catalytically to the corresponding amine, which is protected by a pivaloyl group. Treatment of the product with oxalyl chloride and aluminum chloride, followed by dehydrogenation with an agent such as 2,3-dichloro-5,6-dicyanobenzoquinone (DDQ) and then oxidation with alkaline hydrogen peroxide, gives a diacid. Heating this diacid with an amine such as dimethylethylenediamine and then removal of the protecting group by acid hydrolysis provides the desired 5-amino compound of formula I.

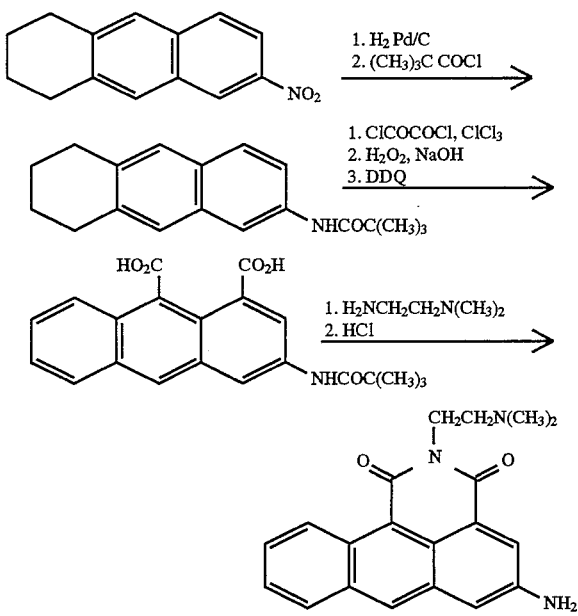

The compounds of the invention containing basic nitrogen form salts with acids, both organic and inorganic acids. Of particular value are salts with pharmaceutically-acceptable acids especially in dosage forms predicated on aqueous systems where the enhanced water solubility of the salts is most advantageous. Salts formed with pharmaceutically unacceptable acids are also useful in the isolation and purification of the basic nitrogen-containing present new compounds. Salts include those formed with hydrochloric, sulfuric, nitric, perchloric, benzenesulfonic, toluenesulfonic, phosphoric, acetic, malic, malonic, tartaric and similar such acids.

The compounds of the present invention can be administered to the host in a variety of forms adapted to the chosen route of administration, i.e., orally, intravenously, intramuscularly or subcutaneously.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium, stearate; and a sweetening agent such as sucrose, lactose or saccharin may be added or a flavoring agent such as peppermint, oil of wintergreen, or cherry flavoring. When the dosage unit form is a capsule, It may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can, be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention. These examples are provided solely for illustrative purposes; thus, the present invention should not be limited thereto.

In the following examples the numbers following the name of the compound refers to the compound number.

EXAMPLE 1

Preparation of Anthracene-1,9-Dicarboxylic Acid Anhydride

A suspension of 6.5 g of anthracene-1,9-dicarboxylic acid (E. D. Bergmann and R. Ikan, *J. Org. Chem.*, 23, 907 (1958)) in 100 ml of acetic anhydride was heated at reflux for 3 hours. The mixture was cooled and the orange precipitate was collected by filtration, washed with ether and dried in air to give 5.1 g (68%) of the title compound. Recrystallization from dimethylsulfoxide or toluene gave orange plates with melting point 289°–290° C.

EXAMPLE 2

2-[2'-(dimethylamino)ethyl]-1,2-dihydro-3H-dibenz (deh)-isoquinoline-1,3-dione A suspension of 248 mg (1 mmol) of anthracene-1,9-dicarboxylic acid anhydride in 25 ml of toluene was treated with 106 mg (1.2 mmol) of N,N-dimethylethylenediamine. The mixture was refluxed for 4 hours. The clear yellow reaction solution was concentrated under reduced pressure to an oily residue which was isolated on a silica gel column using a mixture of chloroform-methanol (9.5–0.5 or 9:1) as a solvent to give 245 mg (77%) of the title compound, crystallized from toluene, m.p 126°–128° C. and providing the following analysis. $^1$H NMR ($d_6$DMSO, TS), δ values in ppm. δ2.3 [s,6,N—$CH_3$), 2.4–2.65 (t,2,N—$CH_2$), 4.0–4.25 (t,2,CON—$CH_2$), 7.55–7.9 (m,3,protons 5+9+10), 8.05–8.20 (d,1,H-8), 8.3–8.5 (t<<d over d>>,2,H-4+H-6), 8.9 (s,1,H-7), 9.6–9.8 (d,1,H-11).

EXAMPLE 3

2-[2'-(N-pyrrolidino)ethyl]-1,2-dihydro-3H-dibenz (deh)isoquinoline-1,3-dione (8)

A suspension of 500 mg (2.02 mmol) of anthracene-1,9-dicarboxylic anhydride in 10 ml toluene was treated with 250 mg (2.20 mmol) of 1-(2-aminoethyl)pyrrolidine. The mixture was refluxed overnight. The clear reaction solution was separated from resins by decantation. It was then allowed to cool to room temperature. The crystalline yellow material deposited (640 mg. 92%) was collected and recrystallized from hexane-toluene 1:1 to give yellow crystals of the title compound having a m.p. of 162°–164° C. and providing the following analysis:

$^1$H NMR ($CDCl_3$,TS), δ values in ppm. δ1.65–1.95 (m,4, —$CH_2$—), 2.5–3.0 (m,6,N—$CH_2$), 4.35–4.55 (t,2,CON—$CH_2$), 7.53–7.9 (m,3,H-5+H-9+H-10), 8.0–8.1 (d,1,H-8), 8.23–8.33 (d,1, H-4), 8.65–8.75 (s over d,2,H-6+H-7), 9.9–10.0 (d,1,H-11).

EXAMPLE 4

2-[2'-(N-piperidino)ethyl]-1,2-dihydro-3H-dibenz (deh)iso-quinoline-1,3-dione (7)

A suspension of 500 mg (2.02 mmol) of anthracene-1,9-dicarboxylic anhydride in 10 ml toluene was treated with 283 mg (2.21 mmol) of 1-(2-aminoethyl)piperidine. The mixture was refluxed overnight under nitrogen. The clear reaction solution was separated from tarry material by decantation. It was then allowed to cool to room temperature. The dark yellow solid that precipitated (715 mg, 99%) was collected and crystallized from a mixture of hexane-toluene 1:1, affording yellow crystals of m.p. 171°–173° C. and providing the following analysis:

$^1$H NMR ($CDCl_3$, TS), δ values in ppm. δ1.1–1.8 (m,6, —$CH_2$—), 2.5–2.9 (m,6,N—$CH_2$), 4.35–4.55 (t,2,CON—$CH_2$), 7.55–7.90 (m,3,H-5+H-9+H-10), 8.05–8.15 (d,1,H-8), 8.25–8.35 (d,1,H-4), 8.65–8.75 (s over d, 2, H-6+H-7), 9.9–10.0 (d,2,H-11).

EXAMPLE 5

2-(1'-ethyl-3'piperidinyl)-1,2-dihydro-3H-dibenz (deh)-isoquinoline-1,3-dione (9)

A suspension of 600 mg (2.42 mmol) of anthracene-1,9-dicarboxylic acid anhydride in 10 ml toluene was treated with 343 mg (2.68 mmol) of 3-amino-1-ethyl piperidine. The mixture was refluxed under nitrogen overnight. The clear reaction solution was separated from tarry material by decantation. The toluene was evaporated to give 800 mg (92%) of light brown solid, which was crystallized from a mixture of hexane-toluene (2:1) as buff crystals of the title compound, having melting point 163°–165° C. and providing the following analysis:

$^1$H NMR ($CDCl_1$, TS), δ values in ppm δ1.05–1.20 (t,3,$CH_3$), 1.3–2.2 (m,4,—$CH_2$—), 2.25–2.75 (m,4,N—$CH_2$ endocyclic), 2.9–3.1 (m,2,N—$CH_2$ exocyclic), 5.2–5.62 (m,1,CON—CH), 7.5–7.9 (m,3,H-5+H-9+H-10), 8.0–8.10 (d,1,H-8), 8.25–8.35 (d,1,H-4), 8.65–8.75 (s over d,2,H-6+H-7), 9.85–9.95 (d,1,H-11).

EXAMPLE 6

2-[3'-(Diethanolamino)propyl]-1,2-dihydro-3H-dibenz (deh)isoquinoline-1,3-dione (12)

A suspension of 248 mg (1 mmol) of anthracene-1,9-dicarboxylic anhydride in 45 ml of dry toluene was treated with 194 mg (1.2 mmole) of N-(3-aminopropyl) diethanolamine in 1 ml of absolute ethanol. The mixture was refluxed under nitrogen for 7 hours. The solvent was evaporated and the residue was isolated on a silica gel column using a mixture of chloroform-methanol (8:2) as a solvent to give 311 mg (79%) of the title compound which was crystallized from toluene into yellow needles of melting point 139°–141° C. and providing the following analysis:

$H^1$ NMR ($CDCl_3$, TS), δ values in ppm 1.8–2.1 (quintuplet,2,—$CH_2$—), 2.65–2.8 (m,6,N—$CH_2$), 3.68–3.78 (t,4,$CH_2$—OH), 3.0–3.3 (br s,2,OH), 4.2–4.4 (t,2, CON—$CH_2$), 7.5–7.85 (m,3,H-5+H-9+H-10), 7.95–8.05 (d,1,H-8), 8.15–8.25 (d,1,H-4), 8.6–8.7 (s over d,2,H-6+H-7), 9.75–9.85 (d,1,H-11).

EXAMPLE 7

2-[3'-(dimethylamino)propyl]-1,2-dihydro-3H-dibenz(deh)-isoquinoline-1,3-dione (11)

A suspension of 600 mg (2.42 mmol) of anthracene-1,9-dicarboxylic acid anhydride in 15 ml toluene was treated with 280 mg (2.75 mmol) of 3-dimethylaminopropylamine. The mixture was refluxed under nitrogen overnight. The clear solution was separated from tarry material by decantation. Evaporation of the solvent gave 715 mg (89%) of the title compound which crystallized from a mixture of hexane-toluene (2:1) as yellow needles of melting point 111°–113° C. and providing the following analysis:

$^1$H NMR ($CDCl_3$, TS), δ values in ppm δ1.9–2.15 (quintuplet, 2, —$CH_2$—), 2.3 (s,6,N—$CH_3$), 2.4–2.6 (t,2, N—$CH_2$), 4.2–4.4 (t,2,CON—$CH_2$), 7.48–7.85 (m,3,H-5+H-9+H-10), 7.95–8.05 (d,1,H-8), 8.2–8.3 (d,1,H-4), 8.60–8.70 (s over d,2,H-6+H-7), 9.85–9.995 (d,1,H-11).

EXAMPLE 8

2-(4'-dimethylaminophenyl)-1,2-dihydro-3H-dibenz (deh)-isoquinoline-1,3-dione (10)

A suspension of 300 mg (1.21 mmole) of anthracene-1, 9-dicarboxylic anhydride in 40 ml of absolute ethanol was treated with a solution of 494 mg (3.63 mmole) of N,N-dimethyl-p-phenylenediamine in 10 ml of absolute ethanol. After refluxing the mixture under nitrogen for 24 hours, 20 ml of dry toluene was added and the mixture was refluxed for another 72 hours. The insoluble yellow solid (340 mg) was filtered off and dried in air. It was boiled with 100 ml of dioxane and the insoluble material (110 mg) which represents unreacted anhydride was filtered off. The filtrate, upon evaporation, gave 230 mg (82% based on reacted amount of starting material) of the title compound which was crystallized from dioxane into yellow needles having a melting point of 332°–334° C. and providing the following analysis:

$^1$H NMR ($d_6$DMSO, TS), δ values in ppm.

δ3.18 (s,6,N—CH$_3$), 7.37–7.43 (t,1,H-9), 7.47–7.61 (m<<d over t>>,4,H-5+H-10+H-3'+H-5'), 7.69–7.72 (d,2,H-2'+H-6'), 7.89–7.92 (d,1,H-8), 8–18–8.22 (d,1,H-4), 8.41–8.44 (d,1,H-6), 8.65 (s,1,H-7), 9.50–9.56 (d,1,H-11).

EXAMPLE 9

2-[2'-(dimethylamino)ethyl]-1,2-dihydro-8-nitro-3H-dibenz-(deh)isoquinoline-1,3-dione (13) and 2-[2'-(dimethylamino)-ethyl]-1,2-dihydro-1-nitro-2H-dibenz(deh)isoquinoline-1,3-dione (2)

A stirred solution of 416 mg (1.68 mmol) of anthracene-1,9-dicarboxylic acid anhydride in 25 ml of concentrated sulfuric acid was treated at –10° to –12° C. with a solution of 155 mg of 70% nitric acid (1.7 mmol) in 1 ml of concentrated sulfuric acid. Stirring was continued for 15 minutes after the addition was completed and then the mixture was poured over ice water. The resulting yellow precipitate, a mixture of isomeric mononitro derivatives, was washed well with water and dried in air. It was used directly in the next step.

A suspension of 570 mg (1.95 mmol) of a mixture of mononitro derivatives in 50 ml of dry toluene was treated with a solution of 206 mg (2.35 mmol) of N,N-dimethylethylenediamine in 15 ml of dry ethanol. The mixture was heated at reflux for 4 hours, during which time a clear brownish-yellow solution formed. After evaporation of the solvent, the solid residue was separated into its components by chromatography on a silica gel column using chloroform-acetone (1:1) as solvent. Concentration of the first yellow fraction gave 247 mg (35%) of 2-[2'-(dimethylamino)ethyl]-1,2-dihydro-11-nitro-3H-dibenz (deh)isoquinoline-1,3-dione, which was crystallized from toluene to give yellow flakes with melting point 238°–240° C. and providing the following analysis:

$^1$H NMR ($d_6$DMSO, TS), δ values in ppm.

δ2.99 (s,6,NCH$_3$), 3.52–3.57 (t,2,NCH$_2$), 4,49–4.53 (t,2,CONCH$_2$), 7.79–7.86 (t,1,H-5), 7.92–7.98 (t,1,H-9), 8.47–8.50 (d,1,H-4), 8.59–8.67 [doublet over doublet (appears as triplet), 2,H-6+H-8], 8.75–8.77 (d,1,H-10), 9.32 (s,1,H-7).

Concentration of the second yellow fraction gave 181 mg (26%) of 2-[2'-(dimethylamino)ethyl]-1,2-dihydro-8-nitro-3H-dibenz(deh)isoquinoline-1,3-dione, which was crystallized from hexane-toluene (1:1) into brownish-yellow cubes with melting point 210°–212° C. and providing the following analysis:

$^1$H NMR (CDCl$_3$, TS), δ values in ppm.

δ2.40 (s,6,NCH$_3$), 2.70–2.77 (t,2,NCH$_2$), 4.39–4.45 (t,2,CON—CH$_2$), 7.77–7.86 (m,2,H-5+H-10), 8.27–8.30 (d,1,H-4), 8.35–8.39 (d,1,H-6), 8.75–8.80 (d,1,H-9), 9.42 (s,1,H-7), 10.34–10.38 (d,1,H-11).

EXAMPLE 10

8-Amino-2-[2'-(dimethylamino)ethyl]-1,2-dihydro-3H-dibenz-(deh)isoquinoline-1,3-dione (14)

A solution of 84 mg of 2-[2'-(dimethylamino)ethyl]-8-nitro-1,2-dihydro-3H-dibenz-(deh)isoquinoline-1,3-dione in 100 ml of absolute ethanol was treated with 10 mg of palladium-on-carbon catalyst and shaken with hydrogen at 42 p.s.i. for 5 hours. The mixture was filtered and the filtrate was evaporated to give 77 mg (99.9%) of the title compound as a brown solid that melted partially at 165°–168° C. and completely at 200°–202° C. (melting point of the dihydrochloride salt was above 300° C.).

EXAMPLE 11

2-[2'-(dimethylamino)ethyl]-1,2-dihydro-6-ethyl-3H-dibenz-(deh)isoquinoline-1,3-dione (15)

A solution of 500 mg of 2-[2'-(dimethylamino)ethyl]-1,2-dihydro-3H-dibenz(deh)isoquinoline-1,3-dione in 30 ml of dry tetrahydrofuran was treated with 4 ml of a 2M solution of ethyl magnesium bromide in tetrahydrofuran. The mixture was stirred overnight and then poured into saturated ammonium chloride solution. The two layers were separated and the aqueous layer was extracted with chloroform. The combined organic layers were dried over sodium sulfate and then evaporated to give an oily residue that was separated into its components by preparative thin-layer chromatography on silica gel with acetone-toluene (2:8) as solvent to give starting material (94 mg), a polar brown oil containing 3 components (268 mg), and the title compound (least polar) (118 mg, 27% based on converted starting material) as a yellow solid. The title compound gave upon recrystallization from hexane-toluene (3:1) yellow needles having a melting point of 148°–150° C. and providing the following analysis:

$^1$H NMR (CDCl$_3$, TS), δ values in ppm

δ1.37–1.43 (t,3,CH$_3$), 2.42 (s,6,N—CH$_3$), 2.69–2.75 (t,2,N—CH$_2$), 3.44–3.53 (q,2,CH$_2$), 4.39–4.44 (t,2,CON—CH$_2$), 7.46–7.49 (d,1,H-5), 7.53–7.59 (t,1,H-9), 7.72–7.79 (t,1,H-10), 7.98–8.02 (d,1,H-8), 8.10–8.13 (d,1,H-4), 8.61 (s,1,H-7), 9.93–9.97 (d,1,H-11).

EXAMPLE 12

11-Amino-2-[2'-(dimethylamino)ethyl]-1,2-dihydro-3H-dibenz(deh)isoquinoline-1,3-dione (3)

A solution of 100 mg of 2-[2'-(dimethylamino)ethyl]-11-nitro-1,2-dihydro-3H-dibenz(deh)isoquinoline-1,3-dione in 100 ml of absolute ethanol was treated with 12 mg of palladium-on-carbon and shaken with hydrogen at 42 p.s.i. for 5 hours. The mixture was filtered and the filtrate was concentrated to give 91 mg (99%) of the title compound as a brown solid having a melting point of 150°–152° C. (melting point of dihydrochloride salt was above 300° C.) and providing the following analysis:

$^1$H NMR ($d_6$DMSO, TS), δ values in ppm.

δ2.94 (s,6,N—CH$_3$), 3.30–3.60 (broad,2,NH$_2$), 3.63–3.70 (t,2,N—CH$_2$), 4.50–4.54 (t,2,CON—CH$_2$), 7.81–7.87 (t,1, H-9), 7.93–8.02 (q<<d over t>>,2,H-5+H-10), 8.37–8.41 (d,1,H-8), 8.68–8.75 (t<<d over d>>,2,H-4+H-6), 9.41 (s,1, H-7).

EXAMPLE 13

Preparation of 7-Chloroanthracene-1,9-Dicarboxylic Acid Anhydride

A suspension of 2.0 g of 7-chloro-1,9-oxalylanthracene [Liebermann and Butescu, *Chem. Ber.*, 45, 1213 (1912)] in 40 ml of p-dioxan was treated with 15 ml of 2N NaOH solution and 12 ml of 30% hydrogen peroxide. The ensuing exothermic reaction was controlled by cooling in an ice-water bath. After 40 minutes standing at room temperature, the resulting solution was acidified with dilute $H_2SO_4$ and the yellow precipitate that formed was collected by filtration, washed with water, and dried in air to give 2.14 g (95%) of the dicarboxylic acid. After recrystallization from p-dioxan and dimethylsulfoxide (4:1), it melted at 325°–327° C. (anhydride formed on heating).

A suspension of 2.0 g of the dicarboxylic acid in 50 ml of acetic anhydride was heated under reflux for 48 hours and then cooled to room temperature. The resulting orange solid, after being washed with ethanol and dried, afforded 1.84 g (97%) of the title compound. Recrystallization from p-dioxan and dimethylsulfoxide (4:1) gave orange crystals with melting point 325°–327° C.

EXAMPLE 14

10-Chloro-2-[2'-(dimethylamino)ethyl]-1,2-dihydro-3H-dibenz(deh)isoquinoline-1,3-dione (16)

A mixture of 1 g (3.6 mmol) of 7-chloroanthracene-1,9-dicarboxylic acid anhydride and 0.36 g (4 mmol) of N,N-dimethylethylenediamine in 70 ml of dry toluene was heated under reflux for 8 hours. The resulting solution was evaporated under reduced pressure and the orange residue was purified by column chromatography on silica gel with toluene-methanol (9:1) as solvent. This procedure gave 1.23 g (99%) of the title compound, crystallized from toluene, m.p. 165°–167° C. and providing the following analysis.

$^1$H NMR ($d_6$DMSO,TS), δ values in ppm.

δ2.4(s,6,N—$CH_3$), 2.56–2.80 (t,2,N—$CH_2$), 4.3–4.46(t,2, CON—$CH_2$), 7.45–7.60 (t,1,H-5), 7.68–7.78 (d,1,H-9), 7.87–7.97 (d,1,H-8), 8.19–8.29 (d,1,H-4), 8.62 (s over d,1, H-7), 8.62–8.72 (d over s,1,H-6), 9.93 (s,1,H-11).

Alternatively, 7-chloroanthracene-1,9-dicarboxylic acid was prepared in an ultimate yield of 63% from 2-chloroanthracene following the procedure described in Example 47. It crystallized from a mixture of 1,4-dioxane and methyl sulfoxide (4:1) into yellow plates of m.p. 325°–327° C. A suspension of 1.06 g (3.53 mmole) of this diacid in 70 ml of toluene was refluxed with 360 mg (4.1 mmole) of N,N-dimethylethylenediamine for 8 hours. The toluene was removed under reduced pressure and the residue was purified by column chromatography on silica gel with toluene-methanol (9:1) as the solvent to give 1.23 g (99%) of the title compound, which was crystallized from toluene into orange crystals having a melting point of 165°–167° C. The title compound provided the following analysis:

$^1$H NMR (CDCl$_3$,TS), δ values in ppm.

δ2.43 (s,6a,NCH$_3$), 2.65–2.80(t,2,CH$_2$—N), 4.32–4.47 (t,2,CONCH$_2$), 7.43–7.60 (t,1,H-5), 7.70–7.77 (d,1,H-9), 7.90–7.98 (d,1,H-8), 8.19–8.30 (d,1,H-4) 8.64 (s,1,H-7), 8.64–8.72 (d,1,H-6), 9.93 (s,1,H-11).

EXAMPLE 15

Preparation of 10-Chloroanthracene-1,9-Dicarboxylic Acid Anhydride

To a cold (0° C.) stirred mixture of 5.0 g (23.5 mmol) of 9-Chloroanthracene and 6.5 ml of oxalyl chloride in 35 ml of carbon disulfide was added 4 g of anhydrous aluminum chloride. After two hours additional carbon disulfide (15 ml) and aluminum chloride (4 g) were added. The mixture was stirred 2 more hours at 0° C. and then overnight at room temperature. Dilute HCl was added and the orange precipitate that formed was collected by filtration, washed with water, and then digested well with 100 ml of 5% NaOH solution. The insoluble solids were collected, washed with water and dried in air to give 4.16 g (66%) of 10-chloro-1, 9-oxalyl-anthracene, m.p. 255°–258° C., after crystallization from methanol containing a little p-dioxan. Acidification of the filtrate gave 1.83 g of 10-chloro-9-anthroic acid.

A suspension of 2 g (7.5 mmol) of 10-chloro-1,9-oxalylanthracene in 14 ml of 2N NaOH and 120 ml of p-dioxan at 15° C. was treated portionwise with 14 ml of 30% hydrogen peroxide solution with shaking. After this addition was complete, the mixture was stirred at room temperature for 1 hour, and then diluted with 100 ml of water. Acidification with dilute $H_2SO_4$ resulted in the precipitation of 1.95 g (86%), after drying in air, of 10-chloroanthracene-1,9-dicarboxylic acid. It had a of 269°–271° C. (anhydride formed on heating) after crystallization from p-dioxan.

A suspension of 1.45 g (4.8 mmol) of 10-chloranthracene-1,9-dicarboxylic acid in 50 ml of acetic anhydride was heated under reflux for 4 hours and then cooled to room temperature. The yellow precipitate that formed was collected by filtration, washed with cold methanol and dried to give 0.83 g (61%) of the title compound, m.p. 269°–271° C.

EXAMPLE 16

7-Chloro-2-[2'-(dimethylamino)ethyl]-1,2-dihydro-3H-dibenz(deh)isoquinoline-1,3-dione (17) and 2-[2'-(Dimethylamino)ethyl]-7-[2'-(dimethylamino) ethylamino]-1,2-dihydro-3H-dibenz(deh) isoquinoline-1,3-dione(62)

10-chloroanthracene-1,9-dicarboxylic acid was prepared in an overall yield of 44% from 9-chloroanthracene following the procedure described in Example 47. It crystallized from 1,4-dioxane into yellow needles of melting point 269°–271° C. A suspension of 875 mg (2.91 mmol) of the diacid in 50 ml of dry toluene was refluxed for 8 hours with 295 mg (3.35 mmol) of N,N-dimethylethylenediamine. The solvent was removed under reduced pressure and the residue was chromatographed by column chromatography on silica gel with toluene-methanol (8:2) as solvent to give two fractions. Concentration of the first fraction (yellow) gave a product which was rechromatographed by preparative thin layer chromatography on silica gel with toluene-methanol (9:1) as solvent to give 713 mg (69.46%) of 7-chloro-2-[2'-(dimethylamino)ethyl]-1,2-dihydro-3H-dibenz(deh) isoquinoline-1,3-dione, crystallized from a mixture of hexane-toluene (4:1) into yellow needles of melting point 169°–171° C. and providing the following analysis:

$^1$H NMR(CDCl$_3$, TS), δ values in ppm. δ2.4 (s,6,NCH$_3$), 2.65–2.80 (t,2,CH$_2$N), 4.34–4.5 (t,2,CONCH$_2$), 7.55–7.88 (m,3,H-5+H-9+H-10), 8.50–8.62 (d, 1, H-S), 8.70–8.75 (d,1H-4), 8.75–8.80 (d,1,H-6), 8.90–10.00 (d,1,H-11).

Concentration of the second fraction (pink) gave 100 mg (8.5% of 2-[2'-(dimethylamino)ethyl]-7-[2'-

(dimethylamino)ethylamino]-1,2-dihydro-3H-dibenz(deh) isoquinoline-1,3-dione, crystallized from toluene, providing the following analysis:

$^1$H NMR (d$_6$DMSO,TS), δ values in ppm. δ2.16 (s,6, NH—C—C—NCH$_3$), 2.24 (S,6,CON-C-C-NCH$_3$), 2.50–2.55 (t,2,CON-C-CH$_2$N), 2.59–2.64 (t,2,NHCCH$_2$N), 3.89–3.94 (t,2,NHCH$_2$C—N), 4.16–4.22 (t,2,CONCH$_2$), 7.46–7.52 (t,1,H-9), 7.52–7.58 (t,1,H-5), 7.71–7.76 (t,2H-10+NH), 8.37–8.40 (d,1,H-S), 8.52–8.55 (d,1,H-4), 8.70–8.74 (d,1,H-6), 9.82–9.86 (d,1,H-11).

EXAMPLE 16A

Alternatively, 7-Chloro-2-[2'-(dimethylamino) ethyl]-1,2-dihydro-3H-dibenz(deh)-isoquinoline-1,3-dione was prepared as follows:

A mixture of 0.823 g (2.9 mmol) of 10-chloroanthracene-1,9-dicarboxylic acid anhydride and 0.256 g (3.0 mmol) of N,N-dimethylethylenediamine in 50 ml of dry toluene was heated under reflux for 48 hours. The resulting solution was evaporated to dryness and the residue was purified by column chromatography on silica gel with toluene-methanol (8:2) as solvent, affording a yellow solid that was purified further by preparative thin-layer chromatography on silica gel with toluene-methanol (9:1) as solvent. This procedure gave 0.71 g (69%) of the title compound, which had m.p. 169°–171° C. (decomposition) after recrystallization from hexane and toluene (4:1) and providing the following analysis.

$^1$H NMR (CDCl$_3$,TS) δ values in ppm. δ2.4 (s,6,N—CH$_3$), 2.65–2.78 (t,2,N—CH$_2$), 4.3–4.46 (t,2,CON—CH$_2$), 7.5–7.82 (m,3,H-5+H-9+H-10), 8.44–8.54 (d,1,H-8), 8.65–8.7 (d,2,H-4+H-6), 9.88–9.98 (d,1,H-11).

EXAMPLE 17

2,[2'-(dimethylamino)ethyl]-7-hydroxy-1,2-dihydro-3H-dibenz(deh)isoquinoline-1,3-dione (21).

A solution of 50 mg (0.142 mmol) of 7-chloro-2-[2'-(dimethylamino)ethyl]-1,2-dihydro-3H-dibenz(deh) isoquinoline-1,3-dione in 50 ml of methanol was stirred at room temperature for 6 hours with a solution of 12 mg (0.3 mmol) of sodium hydroxide in 2 ml of water. The reaction-mixture was treated with a few drops of glacial acetic acid, then the solvent was removed under reduced pressure. The residue was chromatographed by preparative thin layer chromatography on silica gel with a mixture of toluene-methanol (9:1) as solvent to give 30 mg (63.3%) of the title compound crystallized from a mixture of hexane-toluene (1:1) containing a little methanol, melting point 162°–165° C. (decomp.) and providing the following analysis:

$^1$H NMR (CDCl$_3$,TS), δ values in ppm. δ2.40 (s,6,NCH$_3$), 2.70–2.73 (t,2,CH$_2$N), 4.40–4.43 (t,1,CONCH$_2$), 7.62–7.65 (t,1,H-9), 7.71–7.74 (t,1,H-5), 7.80–7.83 (t,1,H-10), 8.42–8.44 (d,1,H-8), 8.63–8.65 (d,1,H-4), 8.74–8.76 (d,1,H-6), 10.03–10.05 (d,1,H-11).

IR (KBr disc) 3300–3400cm$^{-1}$(OH stretching).

EXAMPLE 18

2-[2-(dimethylamino)ethyl]-7-methoxy-1,2-dihydro-3-H-dibenz(deh)isoquinoline-1,3-dione (20).

A mixture of 50 mg (0.142 mmol) of 7-chloro-2-[2'-(dimethylamino)ethyl]-1,2-dihydro-3H-dibenz(deh) isoquinoline-1,3-dione and 16.2 mg (0.3 mmol) of freshly prepared sodium methoxide in 25 ml of absolute methanol was stirred at room temperature for 24 hours. The reaction mixture was treated with a few drops of glacial acetic acid and the solvent was evaporated to dryness at 40°–50° C. to a residue which was chromatographed by preparative thin-layer chromatography on silica gel with a mixture of toluene-methanol (9:1) as solvent to give 43 mg (87%) of the title compound, crystallized from a mixture of toluene-hexane (1:5), after cooling in the refrigerator overnight, into red needles of melting point 147°–149° C.(decomposition), and providing the following analysis.

$^1$H NMR(CDCl$_3$,TS) δ values in ppm. δ2.40 (s,6,NCH$_3$), 2.62–2.78 (t,2,CH$_2$N), 4.22 (s,3,OCH$_3$), 4.33–4.48 (t,2, CONCH$_2$), 7.50–8.85 (m,3,H-5+H-9+H-10), 8.36–8.44 (d,1,H-8), 8.56–8.65 (d,1,H-4), 8.65–8.74 (d,1,H-6), 9.95–10.05 (d,1,H-11).

EXAMPLE 19

Preparation of 10-methylanthracene-1,9-Dicarboxylic Acid Anhydride

To a cold (0° C.) stirred mixture of 5 g (26 mmol) of 9-methylanthracene and 6.5 ml of oxalyl chloride in 35 ml of carbon disulfide was added 4 g of anhydrous aluminum chloride. After two hours another 4 g of anhydrous aluminum chloride and 35 ml of carbon disulfide were added and stirring at 0° C. was continued for two hours. The mixture was kept at room temperature overnight, treated with dilute HCl, and the orange precipitate that formed was collected by filtration, washed with water and then digested well with 100 ml of 5% NaOH solution. The insoluble solids were collected by filtration, washed with water and dried to give 3.17 g (50%) of 10-methyl-1,9-oxalylanthracene, m.p. 266°–268° C., after crystallization from p-dioxan. Acidification of the filtrate with concentrated HCl gave 2.06 g of 10-methyl-9-anthroic acid.

A cold (10° C.) suspension of 2.0 g (8.12 mmol) of 10-methyl-1,9-oxalylanthracene in 80 ml of p-dioxan and 15 mL of 2N NaOH was treated portionwise with 13 ml of 30% hydrogen peroxide with shaking. An exothermic reaction ensued and the solids dissolved gradually. After the addition was complete, the mixture was stirred for 40 minutes, and then acidified with dilute H$_2$SO$_4$. The resulting orange precipitate was collected by filtration, washed with water and dried to give 1.97 g (87%) of 10-methyl-1,9-anthracene dicarboxylic acid, which formed yellow crystals, m.p. 275°–280° C. (anhydride formed on heating) after recrystallization from chloroform-p-dioxan (2:1).

A suspension of 1.82 g (6.5 mmol) of the dicarboxylic acid in 25 ml of acetic anhydride was heated under reflux for 4 hours and then cooled to room temperature. The yellow solid was washed with ether and dried to afford 1.04 g of the title compound, m.p. 275°–280° C. A further 0.27 g (total yield 77%) of this compound was obtained by evaporating the filtrate and digesting the residue twice with n-hexane.

EXAMPLE 20

2-[2'-(dimethylamino)ethyl]-7-methyl-1,2-dihydro-3H-dibenz(deh) isoquinoline-1,3-dione (19).

10-methylanthracene-1,9-dicarboxylic acid anhydride was prepared as follows:

10-methylanthracene-1,9-dicarboxylic acid was prepared in an ultimate yield of 43% from 9-methylanthracene following the procedure described in Example 47. The diacid had a melting point of 275°–280° C. after crystallization from a mixture of chloroform-1,4-dioxane-(2:1). When 1.820 g of the diacid was refluxed with 25 ml of acetic anhydride for 4 hours and then the reaction mixture was cooled to room temperature, a crystalline yellow solid (1.044 g) of 10-methyl-anthracene-1,9-dicarboxylic acid anhydride was obtained. The acetic anhydride filtrate, upon evaporation to dryness, then treatment of the residue with hexanes, gave an additional amount of 270 mg of the anhydride. The total yield of the anhydride is 1.314 g (77%), crystallized from a mixture of chloroform-dioxane (3:1) into red needles of melting point 278°–280° C.

A mixture of 500 mg (1.9 mmol) of 10-methyl-anthracene-1,9-dicarboxylic acid anhydride and 176 mg (2.00 mmol) of N,N-dimethylethylenediamine in 50 ml of dry toluene was heated under reflux for 5 hours. The solvent was evaporated to dryness and the residue was chromatographed on a silica gel column, using a mixture of chloroform-methanol (9:1) as a solvent system, to give 605 mg (95%) of the title compound, crystallized from hexane-toluene (3:1) into golden needles of melting point 155°–157° C. and providing the following analysis:

$^1$H NMR (CDCl$_3$,TS), δ values in ppm. δ2.41 (s,6,NCH$_3$), 2.63–2.80 (t,2,CH$_2$N), 3.06 (s,3,CH$_3$), 4.30–4.44 (t,2, CONCH$_2$), 7.45–7.80 (m,3,H-5+H-9+H-10), 8.20–8.28 (d,1,H-8), 8.45–8.53 (d,1,H-4), 8.59–9.65 (d,1,H-6), 9.89–9.99 (d,1,H-11).

Alternatively, the above-identified compound was prepared as follows:

A mixture of 500 mg (1.91 mmol) of 10-methyl-anthracene-1,9-dicarboxylic acid anhydride and 2.0 mmol N,N-dimethylethylenediamine in 50 ml of dry toluene was heated under reflux for 5 hours. The solvent was evaporated and the residual solid was purified by column chromatography on silica gel with chloroform-methanol (9:1) as solvent. This procedure gave 605 mg (95%) of the title compound, crystallized from hexane-toluene (3:1), golden needles with m.p. 155°–157° C. and providing the following analysis:

$^1$H NMR (CDCl$_3$,TS), δ values in ppm δ2.4 (s,6,N—CH$_3$), 2.63–2.80 (t,2,NCH$_2$), 3.08 (s,3,CH$_3$), 4.29–4.46 (t,2, CON—CH$_2$), 7.47–7.82 (m,3,H-5+H-9+H-10), 8.20–8.30 (d,1,H-8), 8.48–8.58 (d,1,H-4), 8.59–8.69 (d,1,H-6), 9.90–10.00 (d,1,H-11).

EXAMPLE 21

1,2-Dihydro-2-[2'-(methylamino)ethyl]-3H-dibenz (deh)-isoquinoline-1,3-dione (22)

A mixture of 477 mg (1.5 mmol) of 2-[2'-(dimethylamino) ethyl]-1,2-dihydro-3H-dibenz(deh) isoquinoline-1,3-dione, 240 mg (1.5 mmol) of bromine, and 25 ml of glacial acetic acid was heated under reflux for 24 hours, cooled to room temperature, and diluted with ether. The solid that separated was dissolved in methanol and this solution was treated with methanolic KOH until it became slightly alkaline. It was then concentrated and the residue was separated into its components by column chromatography on silica gel with chloroform-methanol (19:1, then 9:1) as solvent. The first fraction (orange) gave 400 mg of unreacted starting material. The second fraction (green) gave a solid that was purified by preparative TLC on silica gel with chloroform-methanol (9:1) as solvent. This procedure gave 39 mg of the title compound, which formed a hydrochloride salt of m.p. 238°–235° C. (decomposition). The title compound provided the following analysis.

$^1$H NMR (CDCl$_3$,TS), δ values in ppm. δ1.22 (s,1,HN), 2.55 (s,3NCH$_3$), 3.06–3.11 (t,2,NCH$_2$,), 4.39–4.44 (t,2, CON—CH$_2$), 7.52–7.66 (m,2,H-5+H-9), 7.72–7.79 (t,1,H-10), 7.98–8.01 (d,1,H-8), 8.21–8.24 (d,1,H-4), 8.62–8.65 (d,1,H-6), 8.66 (s,1,H-7), 9.84–9.88 (d,1,H-11).

Alternatively, the title compound was prepared in 30% yield by the procedure described in Example 34, except that 1.5 equivalents of N-methylethylenediamine were used and the chromatography solvent was toluene-methanol (8.5:1.5). Crystallization from hexanestoluene (7:1) gave yellow crystals with m.p. 165°–166° C. and providing the following analysis.

$^1$H NMR (CDCl$_3$,TS), δ values in ppm. δ1.22 (s,1,NH), 2.55 (s,3,CH$_3$), 3.06–3.11 (t,2,NCH$_2$), 4.39–4.44 (t,2, CONCH$_2$), 7.52–7.66 (t over t, 2, H-5+H-9), 7.72–7.78 (t,1,H-10), 7.98–8.01 (d,1,H-8), 8.21–8.24 (d,2,H-4), 8.62–8.65 (d,1,H-6), 8.66 (s,1,H-7), 9.84–9.88 (d,1,H-11).

EXAMPLE 22

1,2-dihydro-2-[2'-(dimethylamino)ethyl]-1,2-dihydro-3H-dibenz-(deh)-isoquinoline-1,3-dione-8-sulfonamide The product of Example 1 is reacted with chlorosulfonic acid, followed by ammonia, and then dimethylethylenediamine in accordance with the procedure described in Example 2, to form the above-identified product.

EXAMPLE 23

Preparation of a Mixture of 2-,6-, and 7-Acetamido-anthracene-1,9-dicarboxylic Acids 2-Acetamidoanthracene was prepared in 97% yield by stirring a solution of 1 equivalent of 2-aminoanthracene and 1.5 equivalents of acetic anhydride in dry tetrahydrofuran for 3 hours at room temperature. This product (2.9 g) was dissolved in 35 ml of carbon disulfide and 4 ml of oxalyl chloride was added. The stirred mixture was cooled to 0° C. and treated with 2.5 g of anhydrous aluminum chloride. Another 35 ml of carbon disulfide and 2.5 g of aluminum chloride were added after 2 hours. The mixture was stirred 2 hours at 0° C. and overnight at room temperature and then treated with dilute HCl. The brown precipitate that formed was washed with water and then digested well with 5% NaOH solution. After collection, the insoluble solids were washed with water and dried in air to give 1.25 g (35%) of a mixture of 2-,6-, and 7-acetamido-1,9-oxalylanthracenes.

A suspension of the acetamtdooxalylanthracenes (1.24 g, 4.27 mmol) in 25 ml of p-dioxane and 8 ml of 5% NaOH was treated at 15° C. with 8 ml of 30% hydrogen peroxide. The mixture was stirred 45 minutes at room temperature, diluted with 50 ml of water, and filtered. The clear brown filtrate was acidified with dilute H$_2$SO$_4$ and the brick-red solid that formed was collected, washed well with water and dried in air to give 1.1 g (80%) of a mixture of the title compounds. This mixture was used directly in Example 24.

EXAMPLE 24

4-,9-, and 10-Acetylamino-2-[2'-(dimethylamino) ethyl]-1,2-dihydro-3H-dibenz(deh)isoquinoline-1,3-diones (32, 28, 27).

A mixture of 2-, 6-, and 7-acetylaminoanthracene-1,9-dicarboxylic acids was prepared as follows:

To a cold (0° C.) stirred mixture of 2.9 g (12.33 mmol) of 2-acetylaminoanthracene, 35 ml of dry carbon disulfide and 7 ml of oxalyl chloride (80.2 mmole), was added at once 2.5 g (18.75 mmol) of anhydrous aluminum chloride. After stirring at 0° C. for two hours, another 35 ml of carbon disulfide and 2.5 g of aluminum chloride were added at once to the reaction mixture and stirring was continued at 0° C. for another two hours, then at room temperature overnight. The mixture was decomposed with cold dilute hydrochloric acid and the brown precipitate was filtered. It was digested well with 100 ml of 5% sodium hydroxide solution and the insoluble solid mixture (1.25 g, 35%) of 2-, 6-, and 7-acetylamino-1,9-oxalylanthracenes was filtered. To a cold stirred suspension of 1.244 (=4.3 mmol) of the latter in 25 ml of dioxane and 8 ml of 2N aqueous sodium hydroxide solution, was added 8 ml of 30% hydrogen peroxide solution. After stirring at room temperature for 45 minutes, 50 ml of water was added and the mixture was filtered from insoluble material. Acidification of the filtrate with dilute sulfuric acid gave a solid mixture (1.1 g, 80% from the oxalylanthracenes) of 2-, 6- and 7- acetylaminoanthracene-1,9-dicarboxylic acids as a brick red solid.

A suspension of 500 mg (1.55 mmol) of a mixture of 2-, 6-, and 7-acetylaminoanthracene-1,9-dicarboxylic acids in 50 ml toluene was refluxed for 7 hours with a solution of 160 mg (1.82 mmol) of N, N-dimethylethylenediamine in 10 ml of ethanol. The solvent was evaporated to dryness and the residue was fractionated by column chromatography with toluenemethanol (8:2), then chloroform-methanol (8:2), and finally chloroform-methanol (1:1) as solvent systems to give three fractions. The solid from the first fraction was rechromatographed by preparative thin layer chromatography on silica gel with toluene-methanol (9:1) to give 14 mg (2.4%) of 4-acetylamino-2-[2'-(dimethylamino)ethyl]-1,2-dihydro-3H-dibenz(deh)isoquinoline-1,3-dione as a yellow solid, providing the following analysis:

$^1$H NMR (CDCl$_3$, TS), δ values in ppm. δ2.40 (s,3, CH$_3$CO), 2.42 (s,6,NCH$_3$), 2.68–2.74 (t,2,CH$_2$N), 4.37–4.42 (t,2,CONCH$_2$), 7.53–7.59 (t,1,H-9), 7.74–7.81 (t,1,H-10), 7.96–7.99 (d,1,H-8), 8.08–8.12 (d,1,H-5), 8.51 (s,1,H-7), 8.99–9.03 (d,1,H-6), 9.91–9.94 (d,1,H-11) 13,32 (s,1,NH).

The second fraction gave 118 mg (20.3%) of 9-acetylamino-2-[2'-(dimethylamino)ethyl]-1,2-dihydro-3H-dibenz(deh)isoquinoline-1,3-dione with melting point 249°–252° C.

The third fraction gave 367 mg of a two component mixture. The solid from this fraction was digested well with chloroform and the insoluble component (51 mg, 8.8%) of the silicic acid salt of the 10-acetylamino-2-[2'-(dimethylamino)ethyl]1,2-dihydro-3H-dibenz(deh) isoquinoline-1,3-dione was filtered and crystallized from toluene into red crystals with melting point above 360° C. and providing the following analysis:

$^1$H(d$_6$DMSO,TS), δ values in ppm. δ2.23 (s,3,COCH$_3$), 2.78 (s,6,NCH$_3$), 3.27–3.29 (T,2,CH$_2$N), 4.44–4.48 (t,2, CONCH$_2$), 7.78–7.84 (t,1,H-5), 8.06–8.11 (d,1,H-9), 8.20–8.24 (d,1,H-8), 8.55–8.58 (d,1,H-8.61–8.63 (d,1,H-6), 9.08 (s,1,H-7), 10.12 (s,1,H-11), 10.84 (s,1,NH).

Evaporation of the chloroform filtrate gave 320 mg (55.1%) of 10-acetylamino-2-[2'-(dimethylamino) ethyl]-1,3-dihydro-3H-dibenz(deh)isoquinoline-1,3-dione, crystallized from toluene as orange crystals with melting point 197°–199° C. and providing the following analysis:

$^1$H NMR (CDCl$_3$, TS), δ values in ppm. δ2.28, (s,3, COCH$_3$), 2.59 (s,6,NCH$_3$), 3.06–3.11 (t,2,CH$_2$N), 4.35–4.40 (t,2,CONCH$_2$), 7.08–7.12 (d,1,H-10), 7.50–7.54 (t,1,H-5), 7.60–7.76 (d,1,H-11), 7.91–7.93 (s over d,2,H-4+H-8), 8.46–8.49 (d,1,H-6), 8.79 (s,1,H-7), 9.23 (s,1,NH).

Alternatively, the title compounds were prepared as follows:

A suspension of a mixture of 2-,3-,6-, and 7-acetamido-1,9-dicarboxylic acids (1 g, 3.09 mmol) in 50 ml of dry toluene was heated under reflux with 310 mg (3.52 mmol) of N,N-dimethylethylenediamine for 15 hours. Anhydrous ethanol (10 ml) was added and reflux was continued another 5 hours. The mixture was concentrated under reduced pressure and the oily residue was chromatographed on silica gel with toluene-methanol as solvent. (8:2). Three fractions were obtained. The first fraction was purified further by preparative TLC on silica gel to give 27 mg (2%) of 4-acetamido-2-[2'-(dimethylamino)ethyl]-1,2-dihydro-3H-dibenz(deh)isoquinoline-1,3-dione as yellow solid. The second fraction gave 244 mg. of the corresponding 9-acetamide derivative, melting point 249°–252° C. An orange solid (714 mg) obtained from the third fraction was extracted with chloroform. The insoluble solid was washed with chloroform and dried in air to give 79 mg (7%) of the silicic acid salt of 10-acetamido-2-[2'-(dimethylamino) ethyl]-1,2-dihydro-3H-dibenz(deh)isoquinoline-1,3-dione, which did not melt below 360° C. Concentration of the chloroform extract gave 632 mg (55%) of 10-acetamido-2-[2'-(dimethylamino)ethyl]-1,2-dihydro-3H-dibenz(deh) isoquinoline-1,3-dione, melting point 197°–199° C. after crystallization from toluene.

EXAMPLE 25

10-Amino-2-[2'-(dimethylamino)ethyl]-1,2-dihydro-3H-dibenz(deh) isoquinoline-1,3-dione (27)

The title compound was prepared in 76% yield from 10-acetylamino-2-[2'-(dimethylamino)ethyl]-1,2-dihydro-3H-dibenz(deh)isoquinoline-1,3-dione following the procedure described in Example 24. It crystallized from toluene, melting point 193°–195° C. and provided the following analysis:

$^1$H NMR (CDCl$_3$, TS) δ values in ppm. δ2.44 (s,6,NCH$_3$), 2.75–2.80 (t,2,CH$_2$N), 4.41–4.47 (t,2,CONCH$_2$), 4.72 (s,2, NH$_2$), 6.92–6.97 (dd,1,H-10,J$_m$=2.29), 7.55–7.61 (t,1,H-5), 7.77–7.81 (d,1,H-11), 8.20–8.23 (d,1,H-4), 8.49 (s,1,H-7), 8.68–8.71 (d,1,H-6), 9.096–9.104 (d,1,H-8,J$_m$=2.014).

Alternatively, the compound can be prepared as follows:

B. A mixture of 210.3 mg of 10-acetamido-2-[2'-(dimethylamino)ethyl)ethyl]-1,2-dihydro-3H dibenz(deh) isoquinoline-1,3-dione, 50 ml of ethanol, and 5 ml of 37% HCl was heated under reflux for 2 hours and then concentrated to dryness. The residue was dissolved in methanol and this solution was made alkaline with methanolic KOH. It was then concentrated to a residue that was purified by preparative TLC on silica gel with toluene-methanol (9:1) as solvent. This procedure gave 162 mg (76%) of the title compound as a brick-red solid that had a melting point of 143°–145° C. after crystallization from toluene.

EXAMPLE 26

10-Amino-2-[2'-(dimethylamino)ethyl]-1,2-dihydro-3H-dibenz(deh)isoquinoline-1,3-dione (31)

The title compound was prepared in 10.4% yield from 10-acetylamino-2-[2'-(dimethylamino)ethyl]-1,2-dihydro-3H-dibenz(deh)isoquinoline-1,3-dione following the procedure described in Example 27, except that the ratio of ethanol to 38% hydrochloric acid was 3:1. It provided the following analysis:

$^1$H NMR (CDCl$_3$, TS), δ values in ppm. δ2.46 (s,6, NCH$_3$), 2.79–2.84 (t,2,CH$_2$N), 4.42–4.47 (t,2,CONCH$_2$), 4.79 (s broad,2,NH$_2$), 6.87–6.90 (dd,1,H-9,J$_{ortho}$ 8.982,J$_m$ 2.148), 7.53–7.59 (t,1,H-5,J$_{ortho}$ 7.416 and 7.338), 7.70–7.74 (d,1,H-8, J$_{ortho}$ 9.034), 8.16–8.20 (dd,1,H-4,J$_{ortho}$ 8–224,J$_m$ 1.091), 8.43 (S,1,H-7), 8.66–8.69 (dd,1,H-6,J$_{ortho}$ 7.181,J$_m$ 1.255), 9.04–9.05 (d,1,H-11,J$_m$=1.986).

The title compound was also prepared by the procedure of Example 25B. From 54 mg of 10-Acetamido-2-[2'-(dimethylamino) ethyl]-1,2-dihydro-3H-dibenz(deh) isoquinoline-1,3-dione was obtained 5 mg (10%) of the title compound.

EXAMPLE 27

4-Amino-2-[2'-(dimethylamino)ethyl]-1,2-dihydro-3H-dibenz(deh) isoquinoline-1,3-dione (33)

A mixture of 15 mg (0.04 mmole) of 4-acetylamino-2-[2'-(dimethylamino)-ethyl]-1,2-dihydro-3H-dibenz(deh) isoquinoline-1,3-dione, 25 ml of ethanol and 2.5 ml of 38% hydrochloric acid was heated under reflux for 3 hours. After removal of the solvent the residue was dissolved in methanol and the solution was made slightly alkaline with methanolic potassium hydroxide. The solution was concentrated under reduced pressure at 25° C. and the residue was purified by preparative thin layer chromatography on silica gel with toluene-methanol (8:2) to give 7 mg (53%) of the title compounds, providing the following analysis:

$^1$H NMR (d$_6$ DMSO, TS), δ values in ppm. δ2.49 (s,6, NCH$_3$), 2.78–2.84 (t,2,CH$_2$N), 4.33–4.38 (t,2,CONCH$_2$), 7.06–7.09 (d,1,H-5), 7.43–7.47 (t,H-9), 7.61–7.68 (t,1,H-10), 7.75–7.79 (d,1,H-6), 7.88–7.91 (d,1,H-8), 8.14 (s broad, 1,NH), 8.31 (s,1,H-7), 9.76 (s broad,1,OH), 9.84–9.87 (d,1, H-11).

The title compound was also prepared by the procedure of Example 25B. From 15 mg of 4-acetamido-2-[2'-(dimethylamino) ethyl]-1,2-dihydro-3H-dibenz(deh) isoquinoline-1,3-dione was obtained 7 mg (53%) of the title compound.

EXAMPLE 28

2-[2'-(dimethylamino)ethyl]-7-methylthio-1,2-dihydro-3H-dibenz(deh)isoquinoline-1,3-dione (25).

A mixture of 50 mg (0.142 mmol of 7-chloro-2-[2'-(dimethyl-amino)ethyl]-1,2-dihydro-3H-dibenz(deh) isoquinoline-1,3-dione and 12 mg (0.171 mmol) of sodium thiomethoxide in 30 ml of anhydrous methanol was stirred at room temperature overnight. After removal of the solvent the residue was chromatographed by preparative thin layer chromatography on silica gel with a mixture of toluene-methanol (9:1) as a solvent to give 34 mg (66%) of the title compound providing the following analysis:

$^1$H NMR (CDCl$_3$, TS), δ values in ppm. δ2.28 (s,6, NCH$_3$), 2.35 (s,3,SCH$_3$), 2.56–2.73 (t,2,CH$_2$N), 4.24–4.42 (t,2,CONCH$_2$), 7.53–7.81 (m,3,H-5+H-9+H-10), 8.63–8.71 (d,1,H-8), 8.93–9.03 (d,1,H-4), 9.17–9.27 (d,1,H-6), 9.89–9.99 (d,1,H-11).

EXAMPLE 29

2-[2'-Imidazolinyl)methyl]-1,2-dihydro-3H-dibenz (deh) isoquinoline-1,3-dione

By treating the compound prepared in Example 1 with amino acetonitrile followed by ethylene diamine dihydrochloride in accordance with the procedure described in Example 2, the above-identified compound can be prepared.

EXAMPLE 30

Using anthracene-1,9-dicarboxylic acid anhydride prepared in Example 1 and the appropriate amine, the following compounds can be prepared in accordance with the procedure described in Example 2: 2-[2'-(1-piperazinyl)ethyl]-1,2-dihydro-3H-dibenz-(deh) isoquinoline-1,3-dione; 2-[2'-(N-morpholinyl)ethyl]-1,2-dihydro-3H-dibenz-(deh) isoquinoline-1,3-dione; 2-[(1'-ethyl-2-pyrrolidinyl)methyl]-1,2-dihydro-3H-dibenz(deh) isoquinoline-1,3-dione; 2-[2'-(1-methyl)-2-pyrrolidinyl) ethyl]-1,2-dihydro-3H-dibenz (deh)isoquinoline-1,3-dione; 2-[(3'-piperidinyl)methyl]-1,2-dihydro-3H-dibenz(deh) isoquinoline-1,3-dione; 2-(3'-pyridyl)-1,2-dihydro-3H-dibenz(deh)isoquinoline-i,3-dione; 2-[2'-(2-pyridyl) ethyl]-1,2-dihydro-3H-dibenz(deh) isoquinoline-1,3-dione; 2-[(1'-aziridinyl)ethyl]-1,2-dihydro-3H-dibenz(deh) isoquinoline-1,3-dione.

EXAMPLE 31

Similarly, using the procedures described herein, the following derivatives of 2-(2'-(dimethylamino)ethyl)-1,2-dihydro-3H-dibenz(deh)isoquinoline-1,3-dione can be prepared:

4-OH, OCH$_3$, NO$_2$, Cl, Br or CF$_3$;
5-OH, or OCH$_3$, Cl or Br;
6-NHCOCH$_3$, NH$_2$, OH, OCH$_3$, Cl, Br, CF$_3$, NO$_2$ or CH$_3$;
7-NHCOCH$_3$', NH$_2$, Cl, Br or CF$_3$;
8-NHCOCH$_3$, OH, OCH$_3$, Cl, Br or CF$_3$;
9-OH, OCH$_3$, Cl, Br, CF$_3$ or NO$_2$;
10-OH, OCH$_3$, CF$_3$, Cl, Br or NO$_2$;
11-NHCOCH$_3$, Cl, OH or OCH$_3$.

The CF$_3$ derivative is prepared from its corresponding bromo or chloro substituent by treatment with CF$_3$CO$_2$Na and CuI, according to established techniques known in the art.

EXAMPLE 32

5-Amino-2-[2'-(dimethylamino)ethyl]-1,2-dihydro-3H-dibenz(deh)isoquinoline-1,3-dione (87), 2-[2,-(Dimethylamino)ethyl]-4-trimethylacetylamino-1,2-dihydro-3H-dibenz(deh)isoquinoline-1,3-dione (86) and 2-[2,-(Dimethylamino)ethyl]-5-trimethylacetylamino-1,2-dihydro-3H-dibenz(deh) isoquinoline-1,3-dione (85) 3-trimethylacetylaminoanthracene-1,9-dicarboxylic acid was prepared as follows:

A mixture of 4 mg (17.62 mmol) of 1,2,3,4-tetrahydro-7-nitroanthracene (John D. Scribner and James A. Miller; J. Chem. Soc., 5377 (1965)) and 0.5 g of palladium-on-carbon catalyst in 200 ml of methanol was shaken with hydrogen at 50 p.s.i. for 5 hours. The catalyst was removed by filtration and the filtrate was concentrated to give 3.4 g (97%) of 7-amino-1,2,3,4-tetrahydroanthracene. To a solution of 3.2 g (16.24 mmol) of the latter in 50 ml of dry tetrahydrofuran was added 2.7 g (26.7 mmol) of triethylamine followed by 3 g (24.9 mmol) of trimethylacetylchloride. After stirring at room temperature overnight, the solvent was removed and the residue was triturated with warm water to give 4.52 g (99%) of 7-trimethylacetylamino-1,2,3,4-tetrahydroanthracene, crystallized from methanol into colorless crystals of melting point 202°–204° C. and providing the following analysis:

$^1$H NMR (CDCl$_3$, TS), δ values in ppm. δ1.35 (s,9,CH$_3$), 1.81–1.87 (m,4,H-2+H-3), 2.9–2.97 (m,4,H-1+H-4), 7.31–7.35 (dd,1,H-6,J$_{ortho}$=8.780, J$_{meta}$=2.196), 7.45 (s broad,3,H-9+H-10+NH), 7.62–7.65 (d,1,H-5,J$_{ortho}$=8.777), 8.090–8.098 (d,1,H-8, J$_{meta}$=2.176).

To a cold (−5° C.) vigorously stirred solution of 4.52 g (16.08 mmole) of 7-trimethylacetylamino-1,2,3,4- tetrahydroanthracene in 220 ml of carbon disulfide was added 15 ml (170.76 mmol) of oxalyl chloride followed by 6 g (45 mmol) of aluminum chloride. The mixture was stirred vigorously at −5° C. to 0° C. for 6 hours then at room temperature overnight. It was then decomposed with 250 ml of cold dilute hydrochloric acid and the yellowish brown precipitate was collected by filtration. Removal of carbon disulfide from the filtrate by evaporation gave a solid residue that was combined with the precipitate. The combined solid was stirred for half an hour with 100 ml of 5% sodium hydroxide solution. The insoluble solid (2.1 g) was collected and chromatographed on a silica gel column with chloroform as solvent to give two fractions. Concentration of the first fraction gave 232 mg (4.3%) of 8,9-oxalyl-7-trimethylacetylamino-1,2,3,4-tetrahydroanthracene, crystallized from ethanol-dioxane (3:1), melting point 276°–278° C. and providing the following analysis:

$^1$H NMR (CDCl$_3$, TS), δ values in ppm. δ1.42 (s,9,CH$_3$), 1.88–1.93 (m,4,H-2+H-3), 3.03–3.10 (m,2,H-4), 3.40–3.47 (m,2,H-1), 7.75 (s,1,H-10), 7.97–8.00 (d,1,H-6), 8.75–8.79 (d,1,H-5), 9.92 (s,1,NH).

Concentration of the second fraction gave 525 mg (9.7%) of 8,9-oxalyl-6-trimethylacetylamino-1,2,3,4-tetrahydroanthracene, crystallized from ethanol-dioxane (3:1), melting point 337°–339° C., and providing the following analysis:

$^1$H NMR (d$_6$ DMSO, TS), δ values in ppm. δ1.30 (s,9, CH$_3$), 1.81–1.83 (m,4,H-2+H-3), 3.01–3.07 (m,2,H-4), 3.24–3.29 (m,2,H-1), 7.92 (s,1,H-10), 8.152–8.158 (d,1,H-7), J$_{meta}$=1.59), 8.507–8.514 (d,1,H-5, J$_{meta}$=1.164).

A mixture of 405 mg (1.21 mmol) of 8, 9-oxalyl-6-trimethylacetylamino-1,2,3,4-tetrahydroanthracene and 1 g (4.40 mmol) of 2,3-dichloro-5,6-dicyano-1,4-benzoquinone in 50 ml dry 1,4-dioxane was heated under reflux for 108 hours. The mixture was cooled to room temperature and the insoluble material was filtered. The filtrate was concentrated to dryness and the residue (400 mg, 99.9%) containing 3-trimethylacetyl-1,9-oxalyl anthracene, was dissolved in 10 ml of 1,4-dioxane. The solution was cooled to 15° C. and then treated while stirring with 4 ml of 1N sodium hydroxide and 3 ml of 30% hydrogen peroxide. After stirring at room temperature for one hour, the mixture was diluted with 30 ml of water. Acidification of the yellow solution with dilute sulfuric acid gave 220 mg (50%) of 3-trimethylacetylaminoanthracene-1,9-dicarboxylic acid which was used directly in the next step.

A suspension of 220 mg (0.6 mmol) of 3-trimethylacetylaminoanthracene-1,9-dicarboxylic acid in 50 ml of toluene was treated with a solution of 84 mg (0.95 mmol) of N,N-dimethylethylenediamine in 20 ml of absolute ethanol. The mixture was heated at reflux overnight. After evaporation of the solvent, the solid residue was chromatographed by column chromatography on silica gel with chloroform-methanol (9.5:0.5) as solvent to give two fractions. Concentration of the first fraction gave 15 mg (6%) of 2-[2'-(dimethylamino)ethyl]-4trimethylacetylamino-1,2-dihydro-3H-dibenz(deh) isoquinoline-1,3-dione, providing the following analysis:

$^1$H NMR (CDCl$_3$, TS), δ values in ppm. δ1.46 (s,9,CH$_3$), 2.41 (s,6,NCH$_3$), 2.69–2.75 (t,2,CH$_2$N), 4.43–4.49 (t,2, CONCH$_2$), 7.57–7.63 (t,1,H-9), 7.79–7.85 (t,1,H-10), 8.04–8.08 (d,1,H-5), 8.20–8.24 (d,1,H-8), 8.65 (S,1,H-7), 9.15–9.19 (d,1,H-6), 10.00–10.04 (d,1, H-11), 13.65 (s,1, NH).

Concentration of the second fraction gave 107 mg (43%) of 2-[2'-(dimethylamino)ethyl]-5-trimethylacetyl-amino-1, 2-dihydro-3H-dibenz(deh)isoquinoline-1,3-dione providing the following analysis:

$^1$H NMR (CDCl$_3$, TS), δ values in ppm. δ1.43 (s,9,CH$_3$), 2.40 (s,6,NCH$_3$), 2.68–2.73 (t,2,CH$_2$N), 4.36–4.41 (t,2, CONCH$_2$), 7.54–7.60 (t,1,H-9), 7.69–7.76 (t,1,H-10), 7.85 (s,1,NH), 7.97–8.00 (d,1,H-8), 8.28–8.29 (d,1,H-4,J$_m$= 2.298), 8.58 (s,1,H-7), 8.98–8.99 (d,1,H-6,J$_m$=2.250), 9.79, 9.83 (d,1,H-11).

A mixture of 25 mg (0.06 mmole) of 2-[2'-(dimethylamino)ethyl]-5-trimethylacetylamino-1,2-dihydro-3H-dibenz(deh)isoquinoline-1,3-dione, 50 ml of ethanol and 3 ml of 38% hydrochloric acid was heated at reflux for 24 hours. After removal of the solvent the residue was dissolved in methanol and the solution was made slightly alkaline with methanolic sodium hydroxide. The solution was concentrated under reduced pressure at 25° C. and the residue was chromatographed by preparative thin layer chromatography on silica gel with chloroform-methanol (9.5:0.5) as solvent to give 10.5 mg of unreacted starting material and 11 mg (95%, based on reacting material) of 5-amino-2-[2'-(dimethylamino) ethyl]-1,2-dihydro-3H-dibenz(deh)isoquinoline-1,3-dione, providing the following analysis:

$^1$H NMR (CDCl$_3$+d$_6$ DMSO, TS), δ values in ppm. δ2.36 (s,6,NCH$_3$), 2.63–2.69 (t,2,CH$_2$N), 4.31–4.37 (t,2, CONCH$_2$), 5.38 (s,2,NH$_2$), 7.36–7.37 (d,1,H-4,J$_m$=2.376), 7.48–7.55 (t,1,H-9), 7.60–7.67 (t,1,H-10), 7.96–7.99 (d, 1,H-8), 8.30–8.31 (d,1,H-6,J$_m$=2.447), 8.48 (s,1,H-7), 9.78–9.82 (d,1,H-11).

EXAMPLE 33

5-Acetamido-2-[2'-(dimethylamino)ethyl]-1,2-dihydro-3H-dibenz(deh)isoquinoline-1,3-dione (105).

The title compound is prepared by treating the corresponding 5-amino derivative prepared in Example 32 with acetic anhydride in pyridine.

EXAMPLE 34

2-(3'-Pyridylmethyl)-1,2-dihydro-3H-dibenz(deh) isoquinoline-1,3-dione (38).

A suspension of one equivalent of anthracene-1,9-dicarboxylic acid in a toluene-ethanol mixture (4:1) was treated with 1.1 equivalents of 3-aminomethylpyridine. The mixture was refluxed under nitrogen until TLC (chloroform-methanol) showed no remaining starting material. The mixture was filtered and concentrated under reduced pressure to a yellow residue which was purified by preparative thin-layer chromatography on silica gel with chloroform as solvent: This procedure gave the title compound (48%) crystallized from toluene, m.p. 211°–213° C. and providing the following analysis:

$^1$H NMR (CDCl$_3$, TS), δ values in ppm. δ6.45 (s,2,CH$_2$), 7.23–7.28 (t,1,H-5'), 7.49–7.56 (t,1,H-9), 7.56–7.75 (t,1,H-5), 7.69–7.75 (t,1,H-10), 7.94–8.20 (d,1,H-4' over d,1,H-8), 8.14–817 (d,1,H-4), 8.51–8.53 (d,1,H-6'), 8.57 (s,1,H-7), 8.57–8.60 (d,1,H-6), 8.93 (s,1,H-2'), 9.6–9.8 (d,1,H-11).

EXAMPLE 35

2-(2'-Pyridylmethyl)-1,2-dihydro-3H-dibenz(deh) isoquinoline-1,3-dione(39).

This compound was prepared in 95% yield by the procedure described in Example 34. Crystallization from toluene gave yellow solid with m.p. 230°–232° C. and providing the following analysis:

$^1$H NMR (CDCl$_3$, TS), δ values in ppm. δ5.65 (s,2,CH$_2$), 7.13–7.18 (t,1,H-5'), 7.36–7.40 (d,1,H-3'), 7.49–7.56 (t,1,H-9), 7.56–7.62 (t,1,H-5), 7.57–7.63 (t,1,H-4'), 7.69–7.75 (t,1,H-10), 7.92–7.95 (d,1,H-8), 8.14–8.17 (d,1,H-4), 8.52–8.55 (d,1,H-6'), 8.57 (s,1,H-8.57–8.60 (d,1,H-6), 9.80–9.83 (d,1,H-11).

EXAMPLE 36

2'-[2-(N-Morpholinyl)ethyl]-1,2-dihydro-3H-dibenz(deh) isoquinoline-1,3-dione (40).

This compound was prepared in 65% yield from anthracen-1,9-dicarboxylic acid and 4-(2-aminoethyl) morpholine following the procedures described in Example 34, except that the chromatography solvent was 1.5% triethylamine in chloroform. Crystallization from toluene or methanol-acetic acid mixture (3:1) gave yellow solid with no definite m.p. (decomposition on heating). It provided the following analysis:

$^1$H NMR (D$_6$DMSO, TS), δ values in ppm. δ3.27–3.37 (m,6,CH$_2$N), 3.53–3.63 (t,4,CH$_2$O), 4.28–4.34 (t,2,CONCH$_2$), 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7) 8.57–8.60 (d,1,H-6), 9.80–9.83 (d,1,H-11).

EXAMPLE 37

2-[(N-Ethyl-2-pyrrolidinyl)methyl]-1,2-dihydro-3H-dibenz(deh)isoquinoline-1,3-dione (41).

This compound was prepared in 99% yield by the procedure described in Example 34 using 2-(2-aminomethyl)-1-ethylpyrrolidine as the amine. The crude product was purified by crystallization from hexanes to give yellow solid with m.p. 128°–130° C. and providing the following analysis:

$^1$H NMR (CDCl$_3$+d$_6$ DMSO, TS), δ values in ppm. δ1.45–1.55 (t,3,CH$_3$), 2.00–2.40 (m,4,CCH$_2$C), 3.10–3.28 (m,2,NCH$_2$ exocyclic), 3.70–3.95 (m,3,NCH$_2$ endocyclic+NCH), 4.70–4.75 (t,2,CONH$_2$), 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7), 8.57–8.60 (d,1,H-6), 9.80–9.83 (d,1,H-11).

EXAMPLE 38

2-[2'-(N-Methyl-2-pyrrolidinyl)ethyl]-1,2-dihydro-3H-dibenz(deh)isoquinoline-1,3-dione (42).

This compound was prepared in 86% yield by the procedure described in Example 34 using 2-(2-aminoethyl)-1-methylpyrrolidine as the amine and a mixture of chloroform-methanol (9:1) as chromatography solvent. Crystallization from hexanes gave yellow solid with m.p. 119°–122° C. and providing the following analysis:

$^1$H NMR (CDCl$_3$, TS), δ values in ppm. δ1.8–2.15 (m,4,CCH$_2$C), 2.2–2.4 (m,2,C-CH$_2$-C exocyclic), 2.4–2.75 (s over m,5,NCH$_3$+NCH$_2$), 3.35–3.53 (m,1,NCH), 4.27–4.35 (t,2,CONCH$_2$), 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7), 8.57–8.60 (d,1,H-6), 9.80–9.83 (d,1,H-11).

EXAMPLE 39

2-[2'-(2"-(Pyridyl)ethyl)]-1,2-dihydro-3H-dibenz(deh)isoquinoline-1,3-dione (43).

The title compound was prepared in 80% yield from anthracene-1,9-dicarboxylic acid and 2-(2'-aminoethyl) pyridine following the procedure described in Example 34, except that it was purified by column chromatography on silica gel using toluene-methanol (8:2) as solvent then by preparative thin-layer chromatography on silica gel with chloroform. The compound crystallizes from a mixture of toluene-hexane 1:2 in yellow crystals of m.p. 167°–169° C. and providing the following analysis:

$^1$H NMR (CDCl$_3$, TS), δ values in ppm. δ3.27–3.34 (t,2,CCH$_2$), 4.63–4.69 (t,2,CONCH$_2$), 7.14–7.17 (t,1,H-5'), 7.30–7.33 (d,1,H-3'), 7.49–7.56 (t,1,H-9), 7.57–7.65 (t over t,2,H-4'+H-5), 7.69–7.75 (t,1,H-10), 7.92–7.95 (d,1,H-8), 8.14–8.17 (d,1,H-4), 8.57 (s,1,H-7), 8.57–8.59 (d,1,H-6'), 8.57–8.60 (d,1,H-6), 9.80–9.3 (d,1,H-11).

EXAMPLE 40

2-(3'-Pyridyl)-1,2-dihydro-3H-dibenz(deh) isoquinoline-1,3-dione (44).

A mixture of 100 mg (0.4 mmole) of anthracene-1,9-dicarboxylic acid anhydride and 350 mg (3.72 mmole) of 3-aminopyridine in 25 ml of N,N-dimethylformamide was heated under reflux for 48 hours. The solvent was evaporated to dryness and the residue was purified by preparative thin-layer chromatography on silica gel with toluene-methanol (8:2) as solvent. The procedure gave the title compound (19%) as yellow solid, crystallized from hexanes-toluene (1:1), m.p. 290°–291° C. and providing the following analysis:

$^1$H NMR (d$_6$ DMSO, TS), δ values in ppm. δ7.35–7.55 (t,1,H-5'), 7.49–7.56 (t,1,H-9), 7.56–7.62 (t,1,H-5), 7.69–7.75 (t,1,H-10), 7.76–7.78 (d,1,H-4') 7.92–7.95 (d,1,H-8), 8.14–8.17 (d,1,H-4), 8.57 (s,1,H-7), 8.57–8.60 (d,1,H-6), 8.678–8.683 (1,d,H-2'), 8.74–8.76 (d,1,H-6'), 9.80–9.83 (d,1,H-11).

EXAMPLE 41

2-[2'-(piperazinyl)ethyl]-1,2-dihydro-3H-dibenz(deh)-isoquinoline-1,3-dione (48)

A suspension of 248 mg (1 mmol) of anthracene-1,9-dicarboxylic acid anhydride, 30 ml of toluene was treated with a solution of 155 mg (1.2 mmol) of N-(2-aminoethyl) piperazine in 5 ml of absolute ethanol. The mixture was refluxed for 16 hours, cooled, and concentrated under reduced pressure. The residue (286 mg) was chromatographed on a silica gel column with chloroform-methanol (7:3) as solvent, then rechromatographed on a silica gel plate with chloroform-methanol-triethylamine (9:1:0.2) as solvent to give a yellow solid that was extracted with boiling toluene. The extract was evaporated to give the title compound (38%) as yellow solid, crystallized from hexanes-toluene (1:1), m.p. 181°–183° C. and providing the following analysis:

$^1$H NMR (CDCl$_3$, TS), δ values in ppm. δ1.94 (s,1,NH), 2.75–2.83 (m,6,axial H-NCH$_2$ exocyclic), 3.01–3.07 (m,4, equatorial H), 4.40–4.42 (t,2,CONCH$_2$), 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7), 8.57–8.60 (d,1,H-6), 9.80–9.83 (d,1,H-11).

EXAMPLE 42

2-[2'-(β-hydroxyethylamino)ethyl]-1,2-dihydro-3H-dibenz(deh)isoquinoline-1,3-dione (66)

This compound was prepared in 16% yield by the procedure described in Example 35, except that the amine was replaced by 2-(2-aminoethylamino)ethanol and the chromatography solvent was chloroform-methanol (8.5:1.5). Crystallization from toluene gave a yellow solid with m.p. of 160°–162° C. and providing the following analysis:

$^1$H NMR (CDCl$_3$, TS), δ values in ppm. δ2.57 (s,1,NH), 2.77–2.81 (t,2,N—CH$_2$—C—O), 2.96–3.02 (t,2,N-C-CH$_2$-N), 3.18–3.33 (br s,1,OH), 3.55–3.6 (t,2,CH$_2$O), 4.31–4.37 (t,2,CONCH$_2$), 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7), 8.57–8.60 (d,1,H-6), 9.80–9.83 (d,1,H-11).

EXAMPLE 43

2-(2'-aminoethyl)-1,2-dihydro-3H-dibenz(deh) isoquinoline-1,3-dione (67)

This compound was prepared in 9% yield by the procedure described in Example 34, except that 2.2 equivalents of ethylenediamine were used and the chromatography solvent was toluene-methanol (8.5:1.5). Crystallization from ether containing the least amount of methanol gave a yellow solid providing the following analysis:

$^1$H NMR (CDCl$_3$, TS), δ values in ppm. δ1.71–1.94 (br s,2,NH$_2$), 3.11–3.16 (t,2,NCH$_2$), 4.32–4.37 (t,2,CONCH$_2$), 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7), 8.57–8.60 (d,1,H-6), 9.80–9.83 (d,1,H-11).

EXAMPLE 44

2-[2-(1-Aziridinyl)ethyl]-1,2-dihydro-3H-dibenz (deh) isoquinoline-1,3-dione (68)

A suspension of one equivalent of anthracene-1,9-dicarboxylic acid anhydride in toluene was treated with 1.5 equivalents of 1-(aminoethyl)aziridine. The mixture was refluxed under nitrogen until TLC showed no remaining starting material. It was filtered and concentrated under reduced pressure to a yellow solid that was purified by preparative thin layer chromatography on neutral alumina with chloroform as solvent. The procedure gave the title compound in 10% yield, crystallized from hexanes-toluene (1:1), m.p. 139°–141° C. and providing the following analysis.

$^1$H NMR (CDCl$_3$, TS), δ values in ppm. δ1.26–1.28 (d,2,H above aziridine ring), 1.78–1.80 (d,2,H below aziridine ring), 2.58–2.63 (t,2,NCH$_2$), 4.35–4.55 (t,2,CONCH$_2$) 7.49–7.56 (t,1,H-9), 7.56–7.62 (t,1,H-5), 7.69–7.75 (t,1,H-10), 7.92–7.95 (d,1,H-8), 8.14–8.17 (d,1,H-4), 8.57 (s,1,H-7), 8.57–8.60 (d,1,H-6), 9.80–9.83 (d,1,H-11).

EXAMPLE 45

6-Acetylamino-2-[2'-(dimethylamino)ethyl]-1,2-dihydro-3H-dibenz(deh)isoquinoline-1,3-dione (82) and 8-Acetylamino-2-[2'-(dimethylamino)ethyl]-1,2-dihydro-3H-dibenz(deh)isoquinoline-1,3-dione (61).

A mixture of 4- and 5-acetylaminoanthracene-1,9-dicarboxylic acids was prepared in an overall yield of 41% from 1-acetylaminoanthracene following the procedure described in Example 24. A suspension of 2.27 g (7 mmol) of this mixture in 100 ml of toluene was refluxed overnight with a solution of 0.741 g of N,N-dimethylethylenediamine in 10 ml of ethanol. Evaporation of the solvent gave 2.6 g (98%) of a reddish brown solid. A sample (120 mg) of this solid was isolated by preparative thin layer chromatography on silica gel with a mixture of chloroform-acetonetriethylamine (50, 50:1.5) as solvent to give two bands. The first band (higher Rf value) gave 18 mg (15%) of 6-acetylamino-2-[2'[dimethylamino)ethyl]-1,2-dihydro-3H-dibenz(deh)isoquinoline-1,3-dione, crystallized from methanol-ether, melting point 253°–255° C. and providing the following analysis:

$^1$H NMR (d$_6$ DMSO, TS), δ values in ppm. δ2.32 (s,3, CH$_3$CO), 2.82 (s,6,NCH$_3$), 3.34–3.44 (t,2,CH$_2$N), 4.43–4.48 (t,2,CONCH$_2$), 7.86–7.92 (m,3,H-5+H-9+H-10), 8.66–8.69 (d,2,H-4+H-8), 9.46 (s,1,H-7), 9.71–9.75 (dd,1,H-11), 10.45 (S,1,NH).

The second band gave 52 mg (43%) of 8-acetylamino-2-[2'(dimethylamino)ethyl]-1,2-dihydro-3 H-dibenz(deh) isoquinoline-1,3-dione, which crystallized from methanol-ether to give melting point 245°–250° C. and providing the following analysis and chemical properties:

$^1$H NMR (d$_6$ DMSO, TS), δ values in ppm. δ2.32 (s,3, CH$_3$CO), 2.43 (s,6,CH$_3$N), 2.80–2.84 (t,2,CH$_2$N), 4.29–4.34 (t,2,CONCH$_2$), 7.84–7.90 (m,3,H-5+H-9+H-10), 8.61–8.66 (m,2,H-4+H-6), 9.39 (s,1,H-7), 9.70–9.74 (t,1,H-11), 10.40 (s,1,NH).

Chemical properties:

When heated a refluxing mixture of ethanol-37% hydrochloric acid (10:1) for 4 hours, it gave 8-amino-2-[2'-dimethylamino)ethyl]-1,2-dihydro-3H-dibenz(deh)isoquinoline-1,3-dione (Example 10) in 88% yield.

EXAMPLE 46

11-Acetylamino-2-[2'-(dimethylamino)ethyl]-1,2-dihydro-3H-dibenz(deh)isoquinoline-1,3-dione (52).

A solution of 66 mg (2 mmol) of 11-amino-2-[2'-(dimethylamino)ethyl]-1,2-dihydro-3H-dibenz(deh) isoquinoline-1,3-dione in 5 ml of dry tetrahydrofuran was treated with 45.4 mg (4.45 mmol) of acetic anhydride and four drops of triethylamine. After stirring at room temperature for 15 hours, 90 mg of acetic anhydride and 12 drops of triethylamine were added and the mixture was refluxed for 24 hours. The solvent was evaporated and the residue was treated with 20 ml of warm water and allowed to stand for a few hours. The water was removed under reduced pressure and the residue was isolated by preparative thin-layer chromatography on silica gel with chloroform-methanol (9:1) as solvent to give 18 mg of unreacted starting amine and 30 mg (55.5% based on reacted material) of the title compound, crystallized from ether, melting point 156°–158° C. and providing the following analysis:

$^1$H NMR (CDCl$_3$, TS), δ values in ppm. δ2.24 (s,3, COCH$_3$), 2.47 (s,6,NCH$_3$), 2.82–2.87 (t,2,CH$_2$N), 4.46–4.51 (t,2,CONCH$_2$), 7.67–7.75 (m,2,H-5+H-9), 7.97–8.00 (d,1, H-10), 8.15–8.18 (d,1,H-8), 8.32–8.35 (d,1,H-4), 8.74–8.76 (d,1,H-6), 8.85 (s,1,H-7), 10.13 (s,1,NH).

EXAMPLE 47

7-Acetylamino-2-[2'-(dimethylamino)ethyl]-1,2-dihydro-3H-dibenz(deh)isoquinoline-1,3-dione (34).
10-acetylaminoanthracene-1,9-dicarboxylic acid was prepared as follows:

To a cold (0° C.) stirred suspension of 1.665 g (7.08 mmol) of 9-acetylaminoanthracene in 15 ml of anhydrous carbon disulfide was added 4 ml (44.3 mmole) of oxalyl chloride followed by 2 g (15.33 mmol) of anhydrous aluminum chloride. After stirring at 0° C. for 2 hours another 2 g of aluminum chloride and 20 ml of carbon disulfide were added to the reaction mixture and stirring was continued at 0° C. for an additional 2 hours, then at room temperature for overnight. The mixture was decomposed with cold dilute hydrochloric acid and the yellow precipitate was collected and digested well with 70 ml of 5% aqueous sodium hydroxide solution. The insoluble solid (0.587 g, 29%) was filtered and suspended in a mixture of 50 ml 1,4-dioxane and 4 ml of 2N aqueous sodium hydroxide solution. The cold stirred suspension was treated with 4 ml of 30% hydrogen peroxide solution and the mixture was stirred at room temperature for 45 minutes. It was then diluted with 100 ml of water and acidified with dilute sulfuric acid to give 0.319 g (49%) of 10-acetylaminoanthracene-1,9dicarboxylic acid which was used directly in the next step without purification.

A suspension of 319 mg (0.99 mmol) of 10-acetylaminoanthracene-1,9-dicarboxylic acid in 25 ml of toluene was refluxed for 18 hours with a solution of 132 mg (1.5 mmol) of N,N-dimethylethylenediamine in 10 ml of ethanol. The mixture was cooled to room temperature and the insoluble material was filtered. The filtrate was evaporated to dryness and the residue was purified by column chromatography on silica gel with toluene-methanol (8:2) as solvent to give 130 mg (35%) of the title compound, crystallized from toluene, melting point 267°–269° C. and providing the following analysis:

$^1$H NMR (CDCl$_3$+d$_6$ DMSO, TS), δ values in ppm. δ2.38 (s,6,NCH$_3$), 2.45 (s,3,COCH$_3$), 2.66–2.72 (t,2,CH$_2$N), 4.36–4.41 (t,2,CONCH$_2$), 7.53–7.59 (t,1,H-9), 7.62–7.68 (t,1,H-5), 7.71–7.78 (t,1,H-10), 8.15–8.19 (d,1,H-8), 8.34–8.38 (d,1,H-4), 8.63–8.65 (d,1,H-6), 9.93–9.97 (d,1,H-11), 10.34 (s,1, NH).

EXAMPLE 48

6-Chloro-2-[2'-(dimethylamino)ethyl]-1,2,-dihydro-3H-dibenz(deh)isoquinoline-1,3-dione (36)

4-chloroanthracene-1,9-dicarboxylic acid was prepared in an ultimate yield of 57.8% from 1-chloroanthracene following the procedure described in Example 47. A suspension of 500 mg (1.66 mmol) of this diacid in 30 ml of toluene was refluxed for 4 hours with a solution of 150 mg (1.7 mmole) of N,N-dimethylethylenediamine in 5 ml of ethanol. The solvent was removed under reduced pressure and the residue was purified by column chromatography on silica gel with chloroform-methanol (9:1) as solvent to give 503 mg (85.8%) of the title compound, crystallized from hexane containing the least amount of methanol, melting point 160°–162° C. and providing the following analysis:

$^1$H NMR (CDCl$_3$, TS), δ values in ppm. δ2.39 (s,6, NCH$_3$), 2.70–2.73 (t,2,CH$_2$N), 4.40–4.43 (t,2, CONCH$_2$), 7.66–7.69 (t,1,H-9), 7.79–7.81 (d,1,H-5), 7.85–7.88 (t,1,H-10), 8.16–8.18 (d,1,H-8), 8.61–8.63 (d,1,H-4), 9.21 (s,1,H-7), 9.98–10.00 (d,1,H-11).

EXAMPLE 49

2-[2'-(Dimethylamino)ethyl]-10-Iodo-1,2-dihydro-3H-dibenz(deh)isoquinoline-1,3-dione (83)

7-Iodoanthracene-1,9-dicarboxylic acid was prepared in an overall yield of 57% from 2-Iodoanthracene following the procedure described in Example 47.

A suspension of 500 mg (1.28 mmol) of the diacid in 30 ml of toluene was refluxed for 4 hours with a solution of 124 mg (1.41 mmole) of N,N-dimethylethylenediamine in 7 ml of ethanol. The solvent was removed under reduced pressure and the residue was purified by column chromatography on silica gel with chloroform-methanol (9.5:0.5) as solvent to give 485 mg (86%) of the title compound, crystallized from toluene, melting point 190°–192° C. and providing the following analysis:

$^1$H NMR (CDCl$_3$, TS), δ values in ppm. δ2.41 (s,6, NCH$_3$), 2.68–2.74 (t,2,CH$_2$N), 4.35–4.40 (t,2,CONCH$_2$), 7.65–7.72 (dd over t,2,H-5+H-9), 7.76–7.80 (dd,1,H-8), 8.21–8.25 (dd,1,H-4), 8.61 (s,1,H-7), 8.65–8.68 (dd,1,H-6), 10.34–10.35 (t, 1, H-11).

EXAMPLE 50

6,8-Dichloro-2-[2'-(dimethylamino)ethyl]-1,2-dihydro-3H-dibenz(deh)isoquinoline-1,3-dione (75) and 8-Chloro-2-[2'-(dimethylamino)ethyl]-6-[2'-(dimethylamino)ethylamino]-1,2-dihydro-3H-dibenz(deh)isoquinoline-1,3-dione (76)

4,5-dichloroanthracene-1,9-dicarboxylic acid was prepared in an overall yield of 65% from 1,8-dichloroanthracene following the procedure described in Example 47. A suspension of 1.866 g (5.57 mmol) of the diacid in 70 ml of toluene was refluxed for 18 hours with a solution of 510 mg (5.8 mmole) of N,N-dimethylethylenediamine in 10 ml of ethanol. The solvent was removed under reduced pressure and the residue was separated by column chromatography on silica gel with chloroform-methanol (9:1) as solvent. Concentration of the first yellow fraction gave 1.55 g (71%) of 6,8-dichloro-2-[2'-(dimethylamino)ethyl]-1,2-dihydro-3H-dibenz(deh) isoquinoline-1,3-dione, crystallized from toluene, melting point 209°–211° C., and providing the following analysis:

$^1$H NMR (CDCl$_3$, TS), δ values in ppm. δ2.39 (s,6, NCH$_3$), 2.69–2.72 (t,2,CH$_2$N), 4.37–4.40 (t,2,CONCH$_2$), 7.67–7.73 (m,2,H-9+H-10), 7.80–7.82 (d,1,H-5), 8.58–8.60 (d,1,H-4), 9.58.(s,1,H-7), 9.88–9.90 (d,1,H-11).

Concentration of the second pink fraction gave a solid which was rechromatographed by preparative thin layer chromatography on silica gel with chloroform-methanol (8:2) to give 17 mg (0.7%) of 8-chloro-2-[2'-dimethylamino)ethyl]-6-[2'(dimethylamino)ethylamino]-1,2-dihydro-3H-dibenz(deh)isoquinoline-1,3-dione having a melting point of 200°–202° C. and providing the following analysis:

$^1$H NMR (CDCl$_3$, TS), δ values in ppm. δ2.40 (s,6,NH—C—C—NCH$_3$), 2.41 (s,6,CO-N-C-C-NCH$_3$), 2.68–2.71 (t,2,CON-C-CH$_2$-N), 2.78–2.81 (t,2,NH-C-CH$_2$-N), 3.39–3.43 (q,2,NHCH$_2$), 4.37–4.40 (t,2,CONCH$_2$), 6.52–6.54 (d,1,H-5), 6.73–6.75 (t,1,NH), 7.58–7.60 (m,2,H-9+H-10), 8.55–8.57 (d,1,H-4), 9.03 (s,1,H-7), 9.91–9.93 (t,1,H-11), J$_m$=5.07).

EXAMPLE 51

2-[2'-(Dimethylamino)ethyl]-11-hydroxy-1,2-dihydro-3H-dibenz(deh)isoquinoline-1,3-dione (57)

A mixture of 2-[2'-(dimethylamino)ethyl]-8-nitro-1,2-dihydro-3H-dibenz(deh)isoquinoline-1,3-dione and 2-[2'-(dimethylamino)ethyl]-1-nitro-1,2-dihydro-3H-dibenz(deh)isoquinoline-1,3-dione was prepared according to the procedure described in Example 9. Catalytic hydrogenation of this mixture following the procedure described in Example 10 or Example 12 gave a mixture of the corresponding amino derivative which was used directly in the next step.

To a cold (−5°–0° C.) stirred solution of 1 g (3 mmol) of the amino derivatives mixture in 5 ml of 32% sulfuric acid was added a cold (0° C.) solution of 215 mg (3.11 mmol) of sodium nitrite in 1 ml of water. Stirring was continued at −5° C.–0° C. for 45 minutes then at room temperature overnight. After warming to about 50° C. for 20 minutes the mixture was cooled to room temperature, neutralized with solid sodium carbonate and extracted with chloroform and then with tetrahydrofuran. The combined extracts were evaporated under reduced pressure and the residue was chromatographed by preparative thin layer chromatography on silica gel with chloroform-acetone (1:1) as solvent. The first reddish brown band gave 112 mg (21.4%) of the title compound, crystallized from hexane containing the least amount of toluene, having a melting point of 132°–133° C. and providing the following analysis:

$^1$H NMR (CDCl$_3$, TS), δ values in ppm. δ2.38 (s,6, NCH$_3$), 2.69–2.75 (t,2,CH$_2$N), 4.42–4.47 (t,2,CONCH$_2$), 7.32–7.36 (d,1,H-10), 7.52–7.71 (m,3,H-5+H-8+H-9), 8.24–8.28 (d,1,H-4), 8.71–8.74 (d,1,H-6), 8.77 (s,1,H-7), 12.07 (s,1,OH).

The second band is yellow and gave 30 mg of 2-[2'-(dimethylamino)ethyl]-1,2-dihydro-3H-dibenz(deh) isoquinoline-1,3-dione (1).

EXAMPLE 52

11-Chloro-2-[2'-(dimethylamino)ethyl]-1,2-dihydro-3H-dibenz(deh)isoquinoline-1,3-dione (58) and 8-Chloro-2-[2'(dimethylamino)ethyl]-1,2-dihydro-3H-dibenz(deh)isoquinoline-1,3-dione A mixture of 2-[2'-(dimethylamino)ethyl]-1-nitro-1,2-dihydro-3H-dibenz(deh)isoquinoline-1,3-dione and 2-[2'-(dimethylamino)ethyl]-8-nitro-1,2-dihydro-3H-dibenz(deh) isoquinoline-1,3-dione was prepared according to the procedure described in Example 9. Catalytic hydrogenation of this mixture following the procedure described in Example 10 or Example 12 gave a mixture of the corresponding 8- and 11-amino derivatives which was used directly in the next step.

To a cold (0° C.) stirred solution of 957 mg (2.57 mmol) of the amino derivatives mixture in 28 ml of 4% hydrochloric acid was added in portions a cold (0° C.) solution of 260 mg (3.77 mmol) of sodium nitrite in 2 ml of water. After complete addition the mixture was stirred at 0° C. for 2 hours. The resulting diazonium salt solution was added at room temperature to a solution of 2.97 g (30 mmol) of freshly prepared cuprous chloride in 27 ml of 11% hydrochloric acid. After stirring at room temperature overnight then at 70° C. for one hour, the mixture was neutralized with sodium bicarbonate and then extracted with chloroform. The extract was concentrated under reduced pressure and the residue was chromatographed by preparative thin layer chromatography on silica gel with chloroform-acetone (1:1) as solvent. The first band was yellow and gave 200 mg (42.3%) of 11-chloro-2-[2'-(dimethylamino)ethyl-1,2-dihydro-3H-dibenz(deh)isoquinoline-1,3-dione, crystallized from a mixture of hexane-toluene (1:1), melting point 214°–216° C. and providing the following analysis:

$^1$H NMR (CDCl$_3$, TS), δ values of ppm. δ2.39 (s,6, NCH$_3$), 2.75–2.81 (t,2,CH$_2$N), 4.40–4.45 (t,2,CONCH$_2$), 7.52–7.58 (t,1,H-9), 7.71–7.77 (t,1,H-5), 7.84–7.88 (d,1,H-10), 8.02–8.05 (d,1,H-8), 8.29–8.32 (d,1,H-4), 8.67–8.70 (d,1,H-6), 8.75 (s,1,H-7).

The second band is reddish brown and gave 12 mg of 2-[2'-(dimethylamino)ethyl]-1-hydroxy-1,2-dihydro-3H-dibenz(deh)isoquinoline-1,3-dione.

The third band is yellow and gave a product which was rechromatographed by preparative thin layer chromatography on silica gel in toluene-methanol (9:1) to give 31 mg (8.7%) of 8-chloro-2-(dimethylamino) ethyl-1,2-dihydro-3H-dibenz(deh)isoquinoline-1,3-dione providing the following analysis:

$^1$HNMR (CDCl$_3$, TS), δ values in ppm. δ2.45 (s,6,NCH$_3$), 2.73–2.81 (t,2,CH$_2$N), 4.38–4.46 (t,2,CONCH$_2$), 7.56–7.71 (m,3,H-5+H-9+H-10), 8.24–8.27 (d,1,H-4), 8.64–8.66 (d,1, H-6), 9.07 (s,1,H-7), 9.80–9.83 (d,1,H-11).

The fourth band gave 33 mg of a reddish purple compound of unreacted 8-amino-2-[2'-(dimethylamino) ethyl]-1,2-dihydro-3H-dibenz(deh)isoquinoline-1,3-dione (Example 10).

EXAMPLE 53

6-Amino-2-[2'-(dimethylamino)ethyl]-1,2-dihydro-3H-dibenz(deh)isoquinoline-1,3-dione (37)

Method A

A mixture of 50 mg (0.14 mmol) of 6-chloro-2-[2'-(dimethylamino)ethyl]-1,2-dihydro-3H-dibenz(deh) isoquinoline-1,3-dione and 10 mg (0.15 mmole) of sodium azide in 15 ml of absolute ethanol was heated at reflux for 48 hours. The solvent was removed under reduced pressure and the residue was chromatographed by preparative thin layer chromatography on silica gel with chloroform-methanol (8:2) as solvent to give 16.1 mg of unreacted starting material and 23 mg (72% based on reacted material) of the title compound, crystallized from toluene, melting point of 225°–227° C., and providing the following analysis:

$^1$H NMR (CDCl$_3$+d$_6$DMSO, TS), δ values in ppm. δ2.27 (S,6,NCH$_3$), 2.52–2.58 (t,2,CH$_2$N), 4.22–4.27 (t,2, CONCH$_2$), 6.77–6.81 (d,1,H-5), 7.55–7.81 (t,1,H-9), 7.75–7.82 (t,1,H-10), 8.08–8.11 (d,1,H-8), 8.22 (s,2,NH$_2$), 8.35–8.38 (d,1,H-4), 9.34 (s,1,H-7), 9.91–9.94 (d,1,H-11).

When dimethylformamide was used as a solvent and the refluxing time was 20 minutes, the title compound was obtained in 76% yield (based on reacted material).

Method B

The title compound was obtained in almost quantitative yield by hydrolysis of 6-acetamido-2-[2'-(dimethylamino) ethyl]-1,2-dihydro-3H-dibenz(deh) isoquinoline-1,3-dione following the procedure described in Example 27.

EXAMPLE 54

2-[2'-(Dimethylamino)ethyl]-6-[2'-(dimethylamino) ethylamino]-1,2-dihydro-3H-dibenz(deh) isoquinoline-1,3-dione (47)

A mixture of 50 mg (0.14 mmole) of 6-chloro-2-[2'-(dimethylamino)ethyl]-1,2-dihydro-3H-dibenz(deh) isoquinoline-1,3-dione and 78 mg (0.89 mmol) of N,N-dimethylethylenediamine in 15 ml of absolute ethanol was heated at reflux for 24 hours. The solvent was evaporated and the residue was chromatographed by thin layer chromatography on silica gel with chloroform-methanol (9:1) as solvent to give 15 mg of unreacted material and 38.5 mg (96% based on reacted material) of the title compound, crystallized from toluene, melting point 191°–193° C., and providing the following analysis:

$^1$H NMR (CDCl$_3$, TS), δ value in ppm. δ2.37 (s,6,NH—C—C—NCH$_3$), 2.42 (s,6,CON-C-C-NCH$_3$), 2.68–2.78 (m,4,CH$_2$N), 3.33–3.39 (q,2,CH$_2$NH), 4.35–4.41 (t,2, CONCH$_2$), 6.40–6.43 (d,1,H-5), 6.50–6.52 (t,1,NH), 7.47–7.53 (t,1,H-9), 7.67–7.74 (t,1,H-10), 7.94–7.97 (d,1, H-8), 8.45–8.48 (s over d,2,H-4+H-7), 9.86–9.89 (d,1,H-11).

EXAMPLE 55

2-[2'-(Dimethylamino)ethyl]-6-(2'-hydroxyethylamino)1,2-dihydro-3H-dibenz(deh)isoquinoline-1,3-dione (89)

A mixture of 50 mg (0.14 mmol) of 6-chloro-2-[2'-(dimethylamino)ethyl]-1,2-dihydro-3H-dibenz(deh)isoquinoline-1,3-dione and 13 mg (0.21 mmol) of ethanolamine in 25 ml of 2-propanol was heated at reflux for 120 hours. After evaporation of the solvent the residue was chromatographed by column chromatography on neutral alumina using chloroform-methanol (9.5:0.5) then (8:2) as solvents to give 26 mg (49%) of the title compound, providing the following analysis:

$^1$H NMR (CDCl$_3$+d$_6$ DMSO, TS), δ values in ppm. δ2.43 (s,6,NCH$_3$), 2.70–2.76 (t,2,CH$_2$N), 3.53–3.63 (q,3,NH-CH$_2$+OH), 3.97–4.01 (t,2,CH$_2$OH), 4.33–4.39 (t,2,CONCH$_2$), 6.51–6.54 (d,1,H-5), 7.40–7.50 (t,1,NH), 7.52–7.55 (t,1,H-9), 7.71–7.76 (t,1,H-10), 8.00–8.03 (d,1,H-8), 8.41–8.45 (d,1,H-4), 9.12 (s,1,H-7), 9.87–9.91 (d,1,H-11).

EXAMPLE 56

2-[2'-(Dimethylamino)ethyl]-6-hydrazino-1,2-dihydro-3H-dibenz(deh)isoquinoline-1,3-dione (88)

A mixture of 100 mg (0.28 mmol) of 6-chloro-2-[2'-(dimethylamino)ethyl-1,2-dihydro-3H-dibenz(deh)isoquinoline-1,3-dione and 14 mg (0.43 mmol) of hydrazine in 25 ml of absolute ethanol was heated at reflux for 36 hours. After evaporation of the solvent, the residue was chromatographed by column chromatography on neutral alumina using chloroform-methanol (9:1) then (8:2) as solvents to give 37 mg (37%) of the title compound, providing the following analysis:

$^1$H NMR (d$_6$DMSO, TS), δ values in ppm. δ2.66 (s,6, NCH$_3$), 3.06–3.11 (t,2,CH$_2$N), 4.33–4.38 (t,2,CONCH$_2$), 4.90 (s broad,2,NH$_2$), 7.16–7.20 (d,1,H-5), 7.63–7.69 (t,1, H-9), 7.82–7.89 (t,1,H-10), 8.03–8.11 (d,1,H-8), 8.44–8.48 (d,1,H-4), 9.43 (s,1,H-7), 9.70 (s broad,1,NH), 9.88–9.92 (d,1,H-11).

EXAMPLE 57

7-Amino-2-[2'-(dimethylamino)ethyl]-1,2-dihydro-3H-dibenz(deh)isoquinoline-1,3-dione (35)

The title compound was prepared in 36% yield (after crystallization) from 7-acetylamino-2-[2'-(dimethylamino)ethyl]-1,2-dihydro-3H-dibenz(deh) isoquinoline-1,3-dione following the procedure described in Example 27, except that the ratio of ethanol to 38% hydrochloric acid was 5:1. The compound crystallized from toluene containing the least amount of methanol into dark pink crystals of melting point 266°–268° C., and providing the following analysis:

$^1$H NMR (d$_6$DMSO, TS), δ values in ppm. δ2.25 (s,6, NCH$_3$), 2.49–2.57 (t,2,CH$_2$N), 4.22–4.27 (t,2,CONCH$_2$), 7.48–7.53 (t,1,H-9), 7.58–7.63 (t,1,H-5), 7.76–7.82 (t,1,H-10), 8.57–8.63 (t,2,H-4+H-8), 8.70 (s,2,NH$_2$), 8.93–8.97 (d,1,H-6), 9.94–9.99 (d,1,H-11).

EXAMPLE 58

7-[2'-(N-ethyleneimino)ethylamino]-2-[2'-(dimethylamino) ethyl]-1,2-dihydro-3H-dibenz(deh)isoquinoline-1,3-dione (63)

A solution of 100 mg (0.28 mmol) of 7-chloro-2-[2'-dimethylamino)ethyl]-1,2-dihydro-3H-dibenz(deh) isoquinoline-1,3-dione in a mixture of 20 ml absolute methanol and 10 ml of dry tetrahydrofuran was treated with 120 mg (1.4 mmol) of N-(2-aminoethyl)ethyleneimine. The mixture was stirred under a nitrogen atmosphere for 240 hours. After removal of the solvent the residue was chromatographed by preparative thin layer chromatography on silica gel with chloroform-methanol (9:1) as solvent to give 23 mg (20%) of the title compound, melting point 116°–118° C. and providing the following analysis:

$^1$H NMR (CDCl$_3$ TS), δ values in ppm. δ1.29–1.31 (t,2,α-CH$_2$ aziridine), 1.91–1.93 (t,2,β-CH$_2$ aziridine), 2.40 (s,6,CH$_3$), 2.48–2.52 (t,2,CH$_2$-N aziridine), 2.68–2.74 (t,2, CH$_2$N), 3.89–3.95 (q,2,NH-CH$_2$), 4.40–4.45 (t,2,CONCH$_2$), 6.72–6.76 (t,1,NH), 7.48–7.58 (m,2,H-5+H-9), 7.73–7.80 (t,1,H-10), 8.27–8.30 (d,1,H-8), 8.56–8.60 (d,1,H-4), 8.72–8.75 (d,1,H-6), 10.02–10.06 (d,1,H-11).

EXAMPLE 59

10-chloro-2-[2'-(dimethylamino)ethyl]-1,2-dihydro-3H-dibenz(deh)isoquinoline-1,3-dione (60)

To a cold (0° C.) stirred solution of 100 mg (0.3 mmol) of 10-amino-2-[2'-(dimethylamino)ethyl]-1,2-dihydro-3H-dibenz(deh)isoquinoline-1,3-dione in 4 ml of 21% hydrochloric acid was added a cold (0° C.) solution of 25 mg (0.36 mmol) of sodium nitrite in 1 ml of water. The mixture was stirred at 0° C. for one hour. The resulting diazonium chloride solution was added at room temperature to a solution of 197 mg (2 mmol) of freshly prepared cuprous chloride in 3 ml of 14% hydrochloric acid. The mixture was stirred at room temperature for 30 minutes, then at ≅50° C. for another 30 minutes. It was then cooled to room temperature, neutralized with sodium carbonate solution and extracted with chloroform. The extract, after drying over anhydrous sodium sulfate, was concentrated under reduced pressure into a residue which was chromatographed by preparative thin layer chromatography on silica gel with a mixture of chloroform-acetone (1:1) as a solvent to give 47 mg (45%) of the title compound, crystallized from a mixture of hexane-toluene (1:1), melting point 215°–216° C. and providing the following analysis:

$^1$H NMR (CDCl$_3$, TS), δ values in ppm. δ2.41 (s,6, NCH$_3$), 2.69–2.75 (t,2,CH$_2$N), 4.37–4.43 (t,2,CONCH$_2$), 7.50–7.55 (d,1,H-10), 7.68–7.75 (t,1,H-5), 7.97–8.00 (d,1, H-11), 8.28–8.31 (d,1,H-4), 8.70–8.75 (s over d,2,H-6+H-8), 10.06 (s,1,H-7).

EXAMPLE 60

2-[2'-(dimethylamino)ethyl]-4-hydroxy-1,2-dihydro-3H-dibenz(deh)isoquinoline-1,3-dione (59), 2-[2'-(dimethylamino)ethyl]-4-methoxy-1,2-dihydro-3H-dibenz(deh) isoquinoline-1,3-dione (71) and 2-[2'-(dimethylamino) ethyl-4-[2'-(dimethylamino) ethylamino]-1,2-dihydro-3H-dibenz(deh) isoquinoline-1,3-dione (72)

2-methoxyanthracene-1,9-dicarboxylic acid was prepared as follows:

To a cold (–10° C.) stirred solution of 500 mg (2.24 mmol) of 2'-methoxyanthracene in 50 ml of 1,2-dichloroethane was added 2 ml (22.2 mmol) of oxalyl chloride followed by 500 mg (3.75 mmol) of anhydrous aluminum chloride. After stirring at –10° C. for 8.5 hours, the mixture was decomposed with 50 ml of dilute hydrochloric acid. The organic layer was separated and the aqueous layer was extracted with chloroform. The extract was combined with the organic layer and the solvent was evaporated to dryness. The residue was separated on a silica gel column to give 226 mg of unreacted 2-methoxyanthracene and 305 mg (88.4% based on reacted material) of 2-methoxy-1,9-oxalylanthracene, crystallized from 1,4-dioxane into red-orange crystals of melting point 243°–245° C. and providing the following analysis:

$^1$H NMR (d$_6$DMSO, TS), δ values in ppm. δ4.15 (s,3, OCH$_3$), 7.59–7.62 (m,2,H-3+H-6), 7.75–7.81 (t,1,H-7), 8.15–8.19 (d,1,H-5), 8.37–8.40 (d,1,H-4), 8.71–8.75 (d,1,H-8), 8.86 (s,1,H-10).

To a cold (15° C.) stirred suspension of 482 mg (1.84 mmol) of 2-methoxy-1,9-oxalylanthracene in 25 ml of dioxane and 6 ml of 2N aqueous sodium hydroxide solution was added 6 ml of 30% hydrogen peroxide solution. After stirring at room temperature for 45 minutes, 50 ml of water was added. The clear yellow solution was acidified with dilute sulfuric acid to give 485 mg (89.1%) of 2-methoxyanthracene-1,9-dicarboxylic acid as orange solid which was used directly in the next step.

A suspension of 485 mg (1.64 mmol) of 2-methoxyanthracene-1,9-dicarboxylic acid in 50 ml of toluene was refluxed for 18 hours with a solution of 241 mg (2.7 mmol) of N,N-dimethylethylenediamine in 30 ml of absolute ethanol. The solvent was evaporated to dryness and the residue was chromatographed by preparative thin layer chromatography on silica gel with toluene-methanol (8:2) as solvent to give three bands. The first band gave 244 mg (45%) of 2-[2'-(dimethylethylamino)ethyl]-4-hydroxy-1,2-dihydro-3H-dibenz(deh)isoquinoline-1,3dione, crystallized from methanol, melting point 197°–199° C., and providing the following analysis:

$^1$H NMR (CDCl$_3$, TS), δ values in ppm. δ2.36 (s,6, NCH$_3$), 2.66–2.71 (t,2,CH$_2$N), 3.52–3.59 (q,2,CONCH$_2$), 7.06–7.10 (d,1,H-5), 7.49–7.55 (t,1,H-9), 7.73–7.79 (t,1,H-10) 7.88–7.92 (d,2,H-6+H-8), 8.30 (s,1,H-7), 9.59–9.62 (d,1,H-11), 9.99–10.03 (t,1,0H,J for long range coupling with CONCH$_2$=2.00).

The second band gave 10 mg (2%) of 2-[2'-(dimethylamino)ethyl]-4-methoxy-1,2-dihydro-3 H-dibenz(deh)isoquinoline-1,3-dione, providing the following analysis:

$^1$H NMR CDCl$_3$, TS), δ values in ppm. δ2.43 (s,6,NCH$_3$), 2.71–2.77 (t,2,CH$_2$N), 4.25 (s,3,OCH$_3$), 4.42–4.48 (t,2, CONCH$_2$), 7.47–7.51 (d,1,H-5), 7.57–7.60 (t,1,H-9), 7.77–7.81 (t,1,H-10), 8.00–8.04 (d,1,H-8), 8.26–8.29 (d,1, H-6), 8.64 (s,1,H-7), 10.02–10.06 (d,1,H-11).

The third band gave 33 mg (5%) of 2-[2'-(dimethylamino) ethyl]-4-[2'-(dimethylamino)ethylamino]-1,2-dihydro-3H-dibenz(deh)isoquinoline-1,3-dione, providing the following analysis:

$^1$H NMR (CDCl$_3$, TS), δ values in ppm. δ2.36 (s,6,NH-C-C-NCH$_3$), 2.44 (s,6,CON-C-C-NCH$_3$), 2.65–2.75 (m,4, CH$_2$N), 3.48–3.55 (q,2,NHCH$_2$), 4.40–4.46 (t,2,CONCH$_2$), 6.96–7.00 (d,1,H-5), 7.44–7.05 (t,1,H-9), 7.69–7.76 (t,1,H-10), 7.76–7.80 (d,1,H-8), 7.85–7.89 (d,1,H-6), 8.23 (s,1,H-7), 9.99–10.03 (d,1,H-11), 10.97–10.99 (t,1,NH,J$_{NH-CH2}$=5.091).

EXAMPLE 61

2-[2'-(dimethylamino)ethyl]-6-hydroxy-1,2-dihydro-3H-dibenz(deh)isoquinoline-1,3-dione (53)

A solution of 100 mg (0.284 mmol) of 6-chloro-2-[2'-(dimethylamino)ethyl]-1,2-dihydro-3H-dibenz(deh) isoquinoline-1,3-dione in 10 ml of ethanol was heated under reflux for 30 minutes with a solution of 30 mg (0.74 mmol) of sodium hydroxide in 1 ml of water. After removal of the solvent the residue was dissolved in methanol and the pH of the solution was adjusted to 7 by methanolic hydrogen chloride. The methanol was evaporated and the residue was chromatographed by preparative thin layer chromatography on silica gel with toluene-methanol (9:1) as solvent to give 13.6 mg of unreacted 6-chloro-2-[2'-(dimethylamino)ethyl] -1,2-dihydro-3H-dibenz(deh)isoquinoline-1,3-dione and 43 mg (52.5% based on reacted material) of the title compound, crystallized from a mixture of toluene-hexane (1:4), melting point 137°–139° C., and providing the following analysis:

$^1$H NMR (CDCl$_3$, TS), δ values in ppm. δ2.41 (s,6, NCH$_3$), 2.69–2.75 (t,2,CH$_2$N), 4.38–4.44 (t,2,CONCH$_2$), 6.87–6.90 (d,1,H-5), 7.57–7.63 (t,1,H-9), 7.78–7.84 (t,1,H-10), 8.08–8.11 (d,1,H-8), 8.62–8.65 (d,1,H-4), 9.13 (s,1,H-7), 9.96–9.99 (d,1,H-11).

EXAMPLE 62

2-[2'-(dimethylamino)ethyl]10-hydroxy-1,2-dihydro-3H-dibenz(deh)isoquinoline-1,3-dione (74)

To a cold (0° C.) stirred solution of 400 mg (1.2 mmol) of 10-amino-2-[2'-(dimethylamino)ethyl]-1,2-dihydro-3H-dibenz(deh)isoquinoline-1,3-dione in a mixture of 4 ml of concentrated hydrochloric acid and 100 ml of water was added a cold (0° C.) solution of 100 mg (1.45 mmol) of sodium nitrite in 2 ml of water. The mixture was stirred at 0° C. for 2 hours, then at room temperature overnight and finally at 50° C. for 20 minutes. The reaction mixture was neutralized with sodium bicarbonate, then extracted with chloroform containing a little methanol. The extract after drying over anhydrous sodium sulphate was concentrated under reduced pressure into a residue which was chromatographed by preparative thin layer chromatography on silica gel with a mixture of chloroform-acetone (4:6), then chloroform-methanol (9.5.0.5) as solvent systems to give 30 mg of yellow solid of 9-chloro-2-[2'-(dimethylamino)ethyl] -1,2-dihydro-3H-dibenz(deh) isoquinoline-1,3-dione and 265 mg (66%) of the title compound, providing the following analysis:

$^1$H NMR (CDCl$_3$+d$_6$DMSO), δ values in ppm. δ2.32 (s,6,NCH$_3$), 2.60–2.63 (t,2,CH$_2$N), 4.24–4.26 (t,2, CONCH$_2$), 6.91–6.93 (d,1,H-10), 7.56–7.59 (t,1,H-5), 7.72–7.72 (d,1,H-4), 7.86 (s,1,H-8), 8.22–8.24 (d,1,H-6), 8.39 (s,1,H-7), 8.50–8.52 (d,1,H-11).

EXAMPLE 63

2-[2'-(dimethylamino)ethyl]-6-methoxy-1,2-dihydro-3H-dibenz(deh)isoquinoline-1,3-dione (54)

A mixture of 100 mg (0.284 mmol) of 6-chloro-2-[2'-(dimethylamino)ethyl]-1,2-dihydro-3H-dibenz(deh) isoquinoline-1,3-dione and 34 mg (0.63 mmol) of freshly prepared sodium methoxide in 15 ml of absolute methanol was heated under reflux for 3 hours. The solvent was evaporated to dryness and the residue was chromatographed by preparative thin-layer chromatography on silica gel with a mixture of toluene-methanol (9:1) as solvent to give 18.2 mg of unreacted starting material and 54 mg (67% based on reacted material) of the title compound crystallized from a mixture of toluene-hexane (1:3), melting point 192°–193° C. and providing the following analysis:

$^1$H NMR (CDCl$_3$, TS), δ values in ppm. δ2.41 (s,6, NCH$_3$), 2.69–2.75 (t,2,CH$_2$N), 4.15 (s,3,OCH$_3$), 4.37–4.43

(t,2,CONCH$_2$), 6.86–6.89 (d,1,H-5), 7.55–7.61 (t,1,H-9), 7.76–7.82 (t,1,H-10), 8.03–8.07 (d,1,H-8), 8.59–8.62 (d,1, H-4), 9.06 (s,1,H-7), 9.92–9.96 (d,1,H-11).

EXAMPLE 64

2-[2'-(dimethylamino)ethyl]-6-ethoxy-1,2-dihydro-3H-dibenz(deh)isoquinoline-1,3-dione (56).

A mixture of 150 mg (0.425 mmol) of 6-chloro-2-[2'-(dimethylamino)ethyl]-1,2-dihydro-3H-dibenz(deh) isoquinoline-1,3-dione and 63 mg (0.926 mmol) of freshly prepared sodium ethoxide in 33 ml of absolute ethanol was heated under reflux for 6 hours. The solvent was evaporated to dryness and the residue was chromatographed by preparative thin-layer chromatography on silica gel with a mixture of toluene-methanol (9:1) as solvent to give 93 mg (60%) of the title compound, crystallized from hexane, melting point 140°–141° C. and providing the following analysis:

$^1$H NMR (CDCl$_3$, TS), δ values in ppm. δ1.64–1.70 (t,3,CH$_3$), 2.41 (s,6,NCH$_3$), 2.68–2.74 (t,2,CH$_2$N), 4.32–4.43 (m,4,CONCH$_2$+OCH$_2$), 6.84–6.87 (d,1,H-5), 7.56–7.62 (t,1,H-9), 7.76–7.83 (t,1,H-10), 8.06–8.09 (d,1, H-8), 8.59–8.62 (d,1,H-4), 9.08 (s,1,H-7), 9.94–9.98 (d,1, H-11).

EXAMPLE 65

2-[2'(dimethylamino)ethyl-10-methoxy-1,2-dihydro-3H-dibenz(deh)isoquinoline-1,3-dione (70)

To a cold (0° C.) solution of 100 mg (0.3 mmol) of a crude sample of 2-[2'-(dimethylamino)ethyl-10-hydroxy-1,2-dihydro-3H-dibenz(deh)isoquinoline-1,3-dione in 100 ml of a mixture of chloroform-methanol (1:1) was added a solution of diazomethane (6.8 mmol) in 20 ml of ether. The mixture was stirred at 0° C. for 2 hours, then kept in the refrigerator at 4° C. for 7 days, after which it was stirred at room temperature in a closed atmosphere for 10 hours. The solvent was evaporated to dryness and the residue was chromatographed by preparative thin-layer chromatography on silica gel with a mixture of toluene-methanol (8.5–1.5) as a solvent to give 8 mg (8%) of the title compound, providing the following analysis:

$^1$H NMR (CDCl$_3$, TS), δ values in ppm. δ2.44 (s,6, NCH$_3$), 2.76–2.78 (t,2,CH$_2$N), 4.11 (s,3,0CH$_3$), 4.43–4.46 (t,2,CONCH$_2$), 7.27–7.29 (d,1,H-10), 7.65–7.68 (t,1,H-5), 7.95–7.97 (d,1,H-11), 8.28–8.30 (d,1,H-4), 8.67 (s,1,H-7), 8.72–8.74 (d,1,H-6), 9.40 (s,1,H-8).

EXAMPLE 66

2-[2'-(dimethylamino)ethyl]-10-methoxy-1,2-dihydro-3H-dibenz(deh)isoquinoline-1,3-dione (55)

A mixture of 50 mg (0.142 mmol) of 10-chloro-2-[2'-(dimethylamino)ethyl]-1,2-dihydro-3H-dibenz(deh) isoquinoline-1,3-dione and 16.2 mg (0.3 mmol) of freshly prepared sodium methoxide in 15 ml of dry N,N-dimethylformamide was heated under reflux in a dry nitrogen atmosphere for 3 hours. The reaction mixture was poured into water and then extracted well with chloroform. The extract was washed twice with water, then with brine and dried over anhydrous sodium sulfate. After evaporation of the chloroform, the residue was chromatographed by preparative thin-layer chromatography on silica gel with a mixture of toluene-methanol (9:1) as solvent to give 9 mg of unreacted starting material and 6.2 mg (15% based on reacted material) of the title compound, providing the following analysis:

$^1$H NMR (CDCl$_3$, TS), δ values in ppm. δ2.25 (s,6, NCH$_3$), 2.78–2.84 (t,2,CH$_2$N), 4.12 (s,3,OCH$_3$), 4.44–4.50 (t,2,CONCH$_2$), 7.28–7.32 (d,1,H-9), 7.68–7.71 (t,1,H-5), 7.97–8.01 (d,1,H-8), 8.31–8.34 (d,1,H-4), 8.72 (s,1,H-7), 8.74–8.77 (d,1,H-6), 9.43 (s,1,H-11).

EXAMPLE 67

2-[2'-(dimethylamino)ethyl]-6-methylthio-1,2-dihydro-3H-dibenz(deh)isoquinoline-1,3-dione (50)

A mixture of 150 mg (0.426 mmol of 6-chloro-2-[2'-(dimethylamino)ethyl]-1,2-dihydro-3H-dibenz(deh) isoquinoline-1,3-dione and 36 mg (0.514 mmol) of sodium thiomethoxide in 50 ml of absolute ethanol was heated under reflux in a dry nitrogen atmosphere for 22 hours. After removal of the solvent the residue was chromatographed by preparative thin layer chromatography on silica gel with a mixture of chloroform-methanol (9.5:0.5) as a solvent to give 110 mg (71%) of the title compound crystallized from a mixture of hexane-toluene (7:1), melting point 130°–132° C. and providing the following analysis:

$^1$H NMR (CDCl$_3$, TS), δ values in ppm. δ2.41 (s,6, NCH$_3$), 2.67–2.73 (s over t,5,CH$_2$N+SCH$_3$), 4.35–4.41 (t,2, CONCH$_2$), 6.79–6.82 (d,1,H-5), 7.53–7.60 (t,1,H-9), 7.74–7.81 (t,1,H-10), 8.02–8.05 (d,1,H-8), 8.54–8.57 (d,1, H-4), 9.00 (s,1,H-7), 9.90–9.94 (d,1,H-11).

EXAMPLE 68

2-[2'-(dimethylamino)ethyl]-6-methylsulfonyl-1,2-dihydro-3H-dibenz(deh)isoquinoline-1,3-dione (51)

A solution of 50 mg (0.137 mmol) of 2-[2' (dimethylamino)ethyl]-6-methylthio-1,2-dihydro-3H-dibenz(deh)isoquinoline-1,3-dione in 5 ml of glacial acetic acid was treated with 0.1 ml of 30% aqueous hydrogen peroxide solution. The mixture was heated on a steam bath for 20 minutes. The solvent was evaporated to dryness and the residue was purified by preparative thin-layer chromatography on silica gel with a mixture of chloroform-methanol (8:2 or 7:3) as solvent to give 38 mg (70%) of the title compound providing the following analysis:

$^1$H NMR (d$_6$DMSO, TS), δ values in ppm. δ3.28 (s,3, SO$_2$CH$_3$), 3.32 (s,6,NCH$_3$), 3.58–3.73 (t,2,CH$_2$N), 4.48–4.49 (t,2,CONCH$_2$), 6.80–6.83 (d,1,H-5), 7.40–7.46 (t,1,H-9), 7.58–7.64 (t,1,H-10), 7.94–7.97 (d,1,H-8), 8.19–8.22 (d,1,H-4), 8.65 (s,1,H-7), 9.47–9.50 (d,1,H-11).

EXAMPLE 69

2-[2'-(dimethylamino)ethyl]-6-methyl-1,2-dihydro-3H-dibenz(deh)isoquinoline-1,3-dione (46)

4-methylanthracene-1,9-dicarboxylic acid was prepared in an overall yield of 14% from 1-methylanthracene following the procedure described in Example 47. A suspension of 500 mg (1.786 mmol) of the diacid in a mixture of toluene (30 ml) and absolute ethanol (20 ml) was refluxed for 5 hours with a solution of 194 mg (2.2 mmol) of N,N-dimethylethylenediamine in 1 ml of absolute ethanol. The solvent was removed under reduced pressure and the residue was purified by column chromatography on silica gel with a mixture of chloroform-methanol (185:15) as a solvent to give 550 mg (93%) of the title compound, crystallized from hexanes, melting point 144°–146° C. and providing the following analysis:

$^1$H NMR (CDCl$_3$, TS), δ values in ppm. δ2.40 (s,6, NCH$_3$), 2.66–2.72 (t,2,CH$_2$N), 2.85 (s,3,CH$_3$), 4.33–4.38 (t,2,CONCH$_2$), 7.41–7.44 (d,1,H-5), 7.52–7.58 (t,1,H-9), 7.70–7.77 (t,1,H-10), 7.80–7.86 (d,1,H-4), 8.70 (s,1,H-7), 9.83–9.87 (d,1,H-11).

EXAMPLE 70

10-chloro-2-[2'-(methylamino)ethyl]-1,2-dihydro-3H-dibenz(deh)isoquinoline-i,3-dione (73)

A mixture of 300 mg (1.062 mmol) of 7-chloroanthracene-1,9-dicarboxylic acid anhydride and 95 mg (1.284 mmol) of N-methylethylenediamine in 50 ml of toluene was heated under reflux for 20 hours. After cooling to room temperature, the insoluble material was filtered and discarded. The filtrate was evaporated to dryness and the residue was chromatographed by preparative thin layer chromatography on silica gel with a mixture of chloroform-methanol (9:1) as a solvent to give 151 mg (42%) of the title compound as an orange solid, crystallized from methanol, melting point 176°–178° C. and providing the following analysis:

$^1$H NMR (CDCl$_3$, TS) δ values in ppm. δ1.45 (s,broad, 1,NH), 2.52 (s,3,CH$_3$), 3.02–3.06 (t,2,CH$_2$N), 4.41–4.44 (t,2,CONCH$_2$), 7.52–7.54 (d,1,H-9), 7.70–7.73 (t,1,H-5), 7.98–8.02 (d,1,H-8), 8.28–8.30 (d,1,H-4), 8.71–8.73 (s over d,2,H-6+H-7), 10.01 (s,1,H-11).

EXAMPLE 71

6-chloro-2-[2'-(methylamino)ethyl]-1,2-dlhydro-3H-dibenz(deh)isoquinoline-1,3-dione (80)

A mixture of 1 g (3.54 mmol) of 4-chloroanthracene-1,9-dicarboxylic acid anhydride and 270 mg (3.649 mmol) of N-methylethylenediamine in 100 ml of absolute ethanol was stirred at room temperature overnight, then heated under reflux for 3 hours. After cooling to room temperature, the insoluble material was filtered and discarded. The filtrate was evaporated to dryness and the residue was chromatographed on a silica gel column with a mixture of chloroform-methanol (8:2) as a solvent system to give a yellowish red semisolid which was rechromatographed by preparative thin layer chromatography on silica gel with a mixture of diethyl ether-methanol (6:4) as solvent to give 270 mg (23%) of the title compound, providing the following analysis:

$^1$H NMR (CDCl$_3$, TS), δ values in ppm. δ1.78 (s,broad, 1,NH), 2.51 (s,3,CH$_3$), 3.02–3.04 (t,2,CH$_2$N), 4.40–4.44 (t,2,CONCH$_2$), 7.64–7.70 (m,2,H-5+H-9), 7.73–7.76 (t,1,H-10), 8.35–8.37 (d,1,H-8), 8.73–8.74 (d,1,H-4), 9.24 (s,1,H-7), 9.91–9.93 (d,1,H-11).

EXAMPLE 72

2-[2'-(methylamino)ethyl]-6-methoxy-1,2-dihydro-3H-dibenz(deh)isoquinoline-1,3-dione (81)

A mixture of 200 mg (0.591 mmol) of 6-chloro-2-[2'-(methylamino)ethyl]-1,2-dihydro-3H-dibenz(deh) isoquinoline-1,3-dione and 70.4 mg (1.304 mmol) of freshly prepared sodium methoxide in 80 ml of absolute methanol was heated under reflux in a dry nitrogen atmosphere for 2 hours. After cooling to room temperature, the insoluble material was filtered and discarded. The filtrate was evaporated to dryness and the residue was chromatographed by preparative thin layer chromatography on silica gel with a mixture of chloroform-methanol (9:1) as a solvent to give 18 mg of unreacted starting material and 40 mg (22.3% based on reacted material) of the title compound, providing the following analysis:

$^1$H NMR (CDCl$_3$, TS), δ values in ppm. δ1.93 (s,broad, 1,NH), 2.52 (s,3,NCH$_3$), 3.01–3.03 (t,2,CH$_2$N), 4.15 (s,3, OCH$_3$), 4.40–4.42 (t,2,CONCH$_2$), 6.86–6.88 (d,1,H-5), 7.57–7.60 (t,1,H-9), 7.77–7.81 (t,1,H-10), 8.04–8.06 (d,1, H-8), 8.60–8.62 (d,1,H-4), 9.07 (s,1,H-7), 9.92–9.94 (d,1, H-11).

EXAMPLE 73

2-(dimethylamino)-1,2-dihydro-3H-dibenz(deh) isoquinoline-1,3-dione (84)

A suspension of 248 mg (1 mmol) of anthracene-1,9-dicarboxylic acid anhydride in 40 ml of dry toluene was refluxed overnight with a solution of 72 mg (1.2 mmol) of N,N-dimethylhydrazine in 10 ml of absolute ethanol. After removal of the solvent the residue was purified by column chromatography on silica gel using chloroform as a solvent to give 215 mg (82%) of the title compound, crystallized from hexane-toluene (1:1), melting point 198°–200° C. and providing the following analysis:

$^1$H NMR (CDCl$_3$, TS), δ values in ppm. δ3.2 (s,6,CH$_3$), 7.60–7.67 (t,1,H-9), 7.70–7.76 (t,1,H-5), 7.80–7.87 (t,1,H-10), 8.09–8.13 (d,1,H-8), 8.32–8.37 (d,1,H-4), 8.76–8.79 (d,1,H-6), 8.81 (s,1,H-7), 9.94–9.98 (d,1,H-11).

EXAMPLE 74

5,8-dinitroazonafide (24), 5,11-dinitroazonafide (18) and 7-hydroxy-11-nitroazonafide (23)

The above compounds were isolated together with 8-nitroazonafide (13) and 11-nitroazonafide (2) when the nitration procedure described in Example 9 was run with two equivalents of nitric acid instead of one equivalent. Chromatography was run as described in Example 9, and the title compounds were separated and collected.

EXAMPLE 75

2-[2'-(dimethyl)ethyl]-10-[(trimethylacetyl)amino]-1,2-dihydro-3H-dibenz(deh)isoquinoline-1,3-dione (96)

The above compound was prepared from 2-[(trimethylacetyl)amino]anthracene by the procedure described in Example 49. Purification by preparative thin layer chromatography on silica gel with toluene-methanol (9:1) as solvent gave a 59% yield of solid with melting point 203°–205° C. after crystallization from hexane containing the least amount of toluene.

EXAMPLE 76

8-chloro-2-[2'-(dimethylamino)ethyl]-1,2-dihydro-3H-dibenz(deh)isoquinoline-1,3-dione (97) and 2-[2'-(dimethylamino)ethyl]-8-hydroxy-1,2-dihydro-3H-dibenz(deh)isoquinoline-1,3-dione (100)

An ice cooled solution of 405 mg (1.22 mmol) of 8-amino-2-[2'-(dimethylamino)ethyl]-1,2-dihydro-3H-dibenz(deh)isoquinoline-1,3-dione in 20 mL of 37% hydrochloric acid was treated with an ice cold solution of 126 mg (1.83 mmol) of sodium nitrite in 3 mL of water. The mixture was stirred at 0° C. for 1.5 hours, then at room temperature overnight, and then at 80° C. for 30 minutes. The mixture was neutralized with sodium bicarbonate and extracted with chloroform. This extract was concentrated under reduced pressure and the residue was separated into its components by preparative thin layer chromatography on silica gel with chloroform-methanol (9:1) as solvent. The first fraction gave 100 mg (23%) of 97 with no definite melting point after crystallization from methanol, and the second fraction gave 54 mg (13%) of 100 with no definite melting point after crystallization from toluene containing the least amount of methanol.

EXAMPLE 77

2-[2'-(dimethylamino)ethyl]-4-methyl-1,2-dihydro-3H-dibenz(deh)isoquinoline-1,3-dione (101) and 2-[2'-(dimethylamino)ethyl]-10-methyl-1,2-dihydro-3H-dibenz(deh)isoquinoline-1,3-dione (102)

The above compounds were prepared from 2-methylanthracene as a mixture by the procedure described in Example 47. Separation of this mixture by chromatography on silica gel using toluene-trimethylamine (250:2) as solvent gave 101 in 34% yield with no definite melting point after crystallization from toluene containing the least amount of methanol, and 102 in 32% yield with melting point 110°–112° C. after crystallization from toluene containing the least amount of methanol.

EXAMPLE 78

6-[2-(dimethylamino)ethoxy]-2-[2'-(dimethylamino) ethyl-1,2-dihydro-3H-dibenz(deh)isoquinoline-1,3-dione (104)

The above compound was prepared from 6-chloro-2-[2'-(dimethylamino)ethyl]-1,2-dihydro-3H-dibenz(deh)isoquinoline-1,3-dione and sodium 2-(dimethylamino) ethoxide in 2-(dimethylamino)ethanol by the procedure described in Example 64. Purification by preparative thin layer chromatography on silica gel with toluenemethanol as solvent gave 104 in 80% yield (based on reacted starting material) with melting point 140°–142° C. after crystallization from hexane.

EXAMPLE 79

2-[2'-(dimethylamino)ethyl]-6-iodo-1,2-dihydro-3H-dibenz(deh)isoquinoline-1,3-dione (106) and 2-[2'-(dimethylamino)ethyl]-8-iodo-1,2-dihydro-3H-dibenz(deh) isoquinoline-1,3-dione (107)

The above compounds were obtained as a mixture from 1-iodoanthracene by the procedure described in Example 49. Separation of this mixture by chromatography on silica gel with chloroform-methanol (9:1) as solvent gave an 89% yield of 106, whose hydrochloride salt had a melting point of 152°–154° C. after crystallization from diethyl ether, and a 2% yield of 107. The mass spectrum of 107 showed a molecular ion at m/e 444 ($C_{20}H_{17}IN_2O_2$).

EXAMPLE 80

2-[2'-(dimethylamino)ethyl]-10-nitro-1,2-dihydro-3H-dibenz(deh)isoquinoline-1,3-dione (112)

Nitrosylsulfuric acid was prepared by dissolving 165 mg (2.4 mmole) of sodium nitrite in 3 mL of 98% sulfuric acid chilled to 10°–15° C. The mixture was stirred until the sodium nitrite dissolved and then it was added to a vigorously stirred solution at 15° C. of 300 mg (0.9 mmol) of 10-amini-2-[2'-(dimethylamino) ethyl]-1,2-dihydro-3H-dibenz(deh)isoquinoline-1,3-dione in 10 ml of glacial acetic acid. Stirring was continued one hour at 5°–10° C. and then the mixture was diluted with excess diethyl ether. The yellow diazonium disulfate salt that separated was collected by filtration, washed with a mixture of ether and methanol (1:1) and quickly dissolved in 10 mL of water at 5° C. This solution was added in portions to a vigorously stirred 10° C. saturated solution of sodium nitrite containing 300 mg of copper powder. The mixture was stirred overnight at room temperature and then diluted with water. The resulting precipitate was collected, dried well, and extracted with dioxane. Evaporation of this extract gave a yellow-brown solid that was purified by column chromatography on silica gel with chloroform-methanol (9.5:0.5) as solvent. This procedure gave 161 mg (49%) of the title compound with a melting point of 240°–242° C. after recrystallization from toluene containing a little hexane.

EXAMPLE 81

10-cyano-2-[2'-(dimethylamino)ethyl]-1,2-dihydro-3H-dibenz(deh)isoquinoline-1,3-dione (113)

10-Amino-2-[2'-(dimethylamino)ethyl]-1,2-dihydro-3H-dibenz(deh)isoquinoline-1,3-dione (200 mg, 0.6 mmol) was converted into its diazonium sulfate as described in Example 80. This salt was dissolved in 10 mL of cold water and the solution was cooled in an ice bath. Cuprous cyanid was prepared by the addition of a solution containing sodium sulfite (2.65 g), sodium bisulfite, and 1.75 g of sodium hydroxide in 20 mL of water to a hot vigorously stirred solution of cupric sulfate pentahydrate and 6.5 g of sodium chloride in 40 mL of water. The cuprous chloride that precipitated was collected by filtration, suspended in 20 mL of cold water, and treated with a solution of 6.5 g of sodium cyanide in 10 mL of water with stirring. The resulting cuprous cyanide solution was cooled to 0° C. and treated with the diazonium sulfate solution described above with vigorous stirring. Stirring was continued at 0° C. for 30 minutes and then at room temperature overnight. The resulting precipitate was collected by filtration, washed with water, and extracted with boiling chloroform. This extract was dried over sodium sulfate, concentrated, and the residue was purified by preparative thin layer chromatography on silica gel with chloroform-methanol (9.5:0.5) as solvent. This procedure gave 13 mg of an unidentified compound in the first fraction and in the second fraction 23 mg (11%) of the title compound with a melting point of 209°–212° C. after crystallization from toluene containing the least amount of methanol.

EXAMPLE 82

2-[2'-(dimethylamino)ethyl]-10-dimethyltriazino-1,2-dihydro-3H-dibenz(deh)isoquinoline-1,3-dione (114)

The diazonium salt described in Example 80 was prepared from 200 mg of the amine. It was dissolved in 20 mL of cold water (5° C.) and added in portions to a rapidly stirred solution of 130 mg of 40% aqueous dimethylamine and 500 mg of sodium carbonate in 15 mL of water. After stirring at 0° C. for 20 minutes and then at room temperature for 15 minutes, the mixture was extracted with chloroform. This extract was concentrated to a solid which was purified by chromatography on a column of neutral alumina with chloroform-triethylamine (300:8) as solvent. This procedure gave a 24% yield of the title compound. A dimeric product also was obtained.

EXAMPLE 83

2-[2'-(dimethylamino)ethyl]-10-fluoro-1,2-dihydro-3H-dibenz(deh)isoquinoline-1,3-dione (117)

The title compound was prepared from 2-fluoroanthracene by the procedure described in Example 49. An 81% yield of solid with a melting point of 173°–175° C. was obtained after purification by preparative thin layer chromatography on silica gel with chloroformmethanol (9.5:0.5) as solvent and crystallization from hexane containing the least amount of toluene.

EXAMPLE 84

7-Bromo-2-[2'-(dimethylamino)ethyl]-1,2-dihydro-3H-dibenz(deh)isoquinoline-1,3-dione (119)

The title compound was prepared from 9-bromoanthracene by the procedure described in Example 47. A 35% yield of solid with melting point 147°–150° C. was obtained after purification by chromatography on a silica gel column with chloroform as solvent, followed by crystallization from ether.

EXAMPLE 85

2-[2'-(dimethylamino)ethyl]-8-methoxy-1,2-dihydro-3H-dibenz(deh)isoquinoline-1,3-dione (103)

The above-identified compound was prepared by treating 2-[2'-(dimethylamino)ethyl]-8-hydroxy-1,2-dihydro-3H-dibenz(deh)isoquinoline-1,3-dione, which was prepared in Example 76, with diazomethane.

The compounds of the present invention are useful as anti-tumor agents. For example, compounds of the present invention are effective against malignant tumors, especially solid tumors and leukemia. They are also effective against hematological tumors. The compounds of the present invention are effective against breast cancer, ovarian cancer, melanomas, colon cancer, lung cancer, carcinomas, sarcomas, and other solid and hematological cancers.

Representative compounds of the present invention were tested for anti-tumor activity in various model systems.

These models included the following:

1) In vitro tumor colony forming assays in soft agar with murine and human tumor cell lines and with fresh human tumors.

2) In vitro tumor cell viability assays using, MTT dye.

3) In vitro tumor cell viability assays using SBS dye.

4) In vivo survival studies in mice bearing solid flank tumors or hematologic malignancies in the peritoneum.

For example, the compounds of the present invention were evaluated for cytotoxic activities in cloned human colon carcinomas. The clonogenic assays were conducted in accordance with the procedure described hereinbelow:

1) Colony Forming Assays in Soft Agar: Fresh human or murine tumors are disaggregated into single cell suspensions using mechanical, hypoosmotic and/or enzymatic (trypsin) methods. The single cells (about $5 \times 10^{4-105}$) are plated in 35 mm plastic petri dishes onto a 1 ml "feeder layer" of 0.3% agar dissolved in growth medium containing 5–10% vol/vol of heat-inactivated fetal bovine serum, molten 0.3% agar and the drug (100 ug/mL). Drug exposures can be performed for one hour or continuously (drugs added to final plating medium). Tumor cell colonies>60 uM in size are counted by automated image analysis after 10–20 days of incubation in a humidified, 5–10% $CO_2$-gassed environment maintained at 37° C. Inhibition of colony formation is calculated based on comparisons to control (untreated) plates wherein the growth of hundreds of colonies/plate is typical. (Salmon S. E., et al., N Engl J Med 298(24): 1321–1327, 1978).

The results are indicated in the following tables.

TABLE 1

Activity of Compounds Against Tumor Cells
Concentration (μ molar) for 50% inhibition of colony formation for human colon tumors

| compd | LOVOp32 | 205p14 | SW80p105 | HT29p30 |
|---|---|---|---|---|
| 1 | 0.3 | 0.4 | 0.15 | 0.34 |
| 2 | 3.0 | 3.0 | 2.5 | 1.75 |
| 3 | 4.0 | 2.6 | 3.1 | 3.6 |
| 7 | 0.75 | 10.0 | 1.0 | 4.4 |
| 8 | 1.0 | 11.7 | 0.9 | 2.6 |
| 9 | 5.6 | 17.5 | 3.0 | 11.25 |
| 10 | NA | NA | 0.75 | 0.25 |
| 11 | 1.6 | 13.5 | 1.3 | 8.3 |
| 12 | 0.8 | 11.5 | 1.3 | 8.3 |
| Amonafide (control) | 0.6 | 0.16 | 0.57 | 0.96 |

MTT assay with cells plated 24 hr. prior to drug addition. 3 day drug exposure.
NA = not active at concentration tested

TABLE 1a

Activities of Compounds Against Sensitive and Multidrug Resistant L1210 Leukemia Cells
Concentration (pg/ml) for 50% inhibition of tumor cells

| Compound # | Sensitive L1210 | Resistant L1210 |
|---|---|---|
| 1 | 0.0025 | 0.0025 |
| 13 | 0.0027 | 0.003 |
| 14 | 5.0 | — |
| 15 | 0.0031 | 0.0031 |
| 16 | 0.0025 | 0.002 |
| 17 | 0.028 | 0.03 |
| 19 | 0.003 | 0.003 |
| 20 | 0.0032 | 0.0028 |
| 21 | 0.0032 | 0.0032 |
| 22 | 0.0032 | 0.0027 |

Six day MTT assay, continuous drug exposure

Compounds of the present invention were tested for their in vitro activity in tumor cells sensitive and resistant to standard anti-cancer agents. The tumor cell lines used in this protocol are 8226 Human Myeloma[1]; 8226/Dox-40[2], L-1210/Murine Leukemia,

[1] 1. Matsuoka, Y, et al. Proc Soc Exptl. Biol. Med., 125, 1246–1250 (1967).
[2] Dalton, W. S., et al. Cancer Research, 46, 5125–5130 (1986). multidrug resistant L-210/[3], 2780 Human Ovarian Cancer and 2780/AD[4].
[3] Dorr, et al., Biochem. Pharmacol., 36, 3115–3120 (1980).
[4] Rogan, A. M., et al., Science, 224, 994–996 (1984).

Each of these resistant cell lines is known as a multidrug resistant or "MDR" cell line. These cell lines produce a 170,00 molecular weight membrane protein termed the P-glycoprotein which acts as an active drug efflux pump. Thus, once a cell produces the P-glycoprotein, it has the capability of pumping out of the cell a large variety of unrelated natural products. These include some of our most active standard antitumor agents such as doxorubicin (adriamycin), vinca alkaloids (such as vincristine and vinblastine) and other DNA binders such as actinomycin D and daunomycin. The protocol for measuring the effectiveness of compounds of the present invention is as follows:

2) In Vitro Tumor Cell Viability Assays Using MTT-Dye: The assay is conducted in accordance with the procedure described by Heo, et al. in Cancer Research, 1990, 50, 3681–3690. Tumors are processed into a single cell suspension as described above. The cells are plated at a concentration of 3–5×10⁴/1 mL well into plastic 96-well plates. Growth medium containing 5–10% (vol/vol) heat-inactivated fetal bovine serum and drug (100 ug/mL) is added prior to incubation at 37° C. for six days. Afterwards the medium containing the drug is removed, the cells are "washed" by centrifugation in fresh medium or phosphate-buffered saline (pH 7.4). A tetrazolium dye is then added (3,4,5-dimethylthiazol-2-yl)-2,5-diphenyl tetrazolium bromide (MTT). This dye forms a colored formazan product upon activation by mitochondrial reductases in viable cells. Typically, the formazan product is solubilized in acid-propanol or DMSO. The intensity of the color is proportional to viable cell numbers and this is quantitated by spectrophotometric absorbance (570 nM) on a micro ELISA plate reader. Test results are calibrated in % control absorbance from untreated tumor cells (Mossman T: *J Immunol Meth* 65: 55–63, 1983).

Using the above procedure, Compound 1 was tested for its cytotoxic activity with respect to various tumor cell lines. The results are indicated hereinbelow in Table 2.

TABLE 2

In Vitro Cytotoxic Activity Insensitive and Multidrug Resistant Tumor*

| Tumor Cell Line | Resistance Spectrum | CMPD Activity (IC50¹ In ug/mL) | CMPD Cross¹ Resistance |
|---|---|---|---|
| 8226 Human Myeloma | Multidrug resistant, P-glycoprotein positive | .011 | 3-fold |
| 8226/DOX-40 | 40-fold resistant to Doxorubicin | .036 | |
| L-1210/Murine Leukemia | | .003 | |
| L-1210/ | MDR, P-glycoprotein (+) 10-fold resistance to Mitomycin C | .003 | None |
| 2780 Human Ovarian Cancer | | 4.0 | None |
| 2780/AD | MDR, P-glycoprotein (+) 10-fold resistance to Doxorubicin | 2.7 | |

*4-day drug exposure in multiwell plastic plates; cell viability measured MTT dye reduction.

Table 2 shows that Compound 1 maintained anti-tumor activity against these multidrug resistant tumors in vitro. The only instance in which Compound 1 did not appear to completely maintain its activity was with the DOX 40 cell line where a possible three-fold cross resistance was evident. However, this is a highly artificial level of resistance (i.e., 40-fold resistance is not seen commonly in the clinic). Thus, in the lower level resistant cell lines, such as the ten-fold mitomycin C resistant L1210 and the tenfold adriamycin resistant 2780 ovarian cancer, Compound 1 maintained its complete activity as shown in Table II.

Using this assay, additional compounds of the present invention were tested for their cytotoxic activity with respect to various tumor cell lines. The results are indicated below.

COMPOUND IC50 DATA RL1210/.1

| COMPOUND # | RL1210 (ng/ml) IC50 | RL1210 (nM) IC50 |
|---|---|---|
| 2 | 20.0 | 50.0 |
| 3 | 250.0 | 678.0 |
| 7 | 20.0 | 51.0 |
| 8 | 4.5 | 11.8 |
| 9 | 240.0 | 609.0 |
| 10 | 720.0 | 1791.0 |
| 11 | 30.0 | 82.0 |
| 12 | 65.0 | 142.0 |
| 13 | 8.0 | 20.0 |
| 14 | 2500.0 | 6755.0 |
| 15 | 90.0 | 235.0 |
| 16 | 10.0 | 26.0 |
| 17 | 80.0 | 206.0 |
| 19 | 25.0 | 70.0 |
| 20 | 42.0 | 109.0 |
| 21 | 50.0 | 135.0 |
| 22 | 7.0 | 20.6 |
| 23 | 8000.0 | 19277.0 |
| 24 | 650.0 | 1463.0 |
| 25 | 490.0 | 1225.0 |
| 27 | 90.0 | 219.0 |
| 28 | 7.0 | 17.0 |
| 30 | 1.1 | 2.7 |
| 31 | 5.8 | 16.0 |
| 32 | 230.0 | 560.0 |
| 33 | 2.9 | 7.9 |
| 34 | 200.0 | 487.0 |
| 35 | 2.5 | 6.8 |
| 36 | 25.0 | 64.0 |
| 37 | 10.0 | 27.0 |
| 38 | 1000.0 | 2674.0 |
| 39 | 10000.0 | 26740.0 |
| 40 | 200.0 | 512.0 |
| 41 | 23.0 | 55.0 |
| 42 | 22.0 | 56.0 |
| 43 | 6000.0 | 15464.0 |
| 44 | 200.0 | 554.0 |
| 45 | 50.0 | 148.0 |
| 46 | 10.0 | 27.0 |
| 47 | .0 | .0 |
| 48 | 200.0 | 463.0 |
| 50 | 8.0 | 20.0 |
| 51 | 240.0 | 555.0 |
| 52 | 1000.0 | 2433.0 |
| 53 | 2.5 | 6.7 |
| 54 | 1.5 | 3.9 |
| 55 | 60.0 | 156.0 |
| 56 | 27.0 | 68.0 |
| 57 | 70.0 | 189.0 |
| 58 | 240.0 | 617.0 |
| 59 | 2000.0 | 5391.0 |
| 60 | 23.0 | 59.0 |
| 61 | 210.0 | 510.0 |
| 62 | 250.0 | 524.0 |
| 63 | 500.0 | 1244.0 |
| 66 | 15.0 | 41.0 |
| 67 | 55.0 | 168.0 |
| 68 | 250.0 | 791.0 |
| 70 | 20.0 | 52.0 |
| 71 | 65.0 | 169.0 |
| 72 | 70.0 | 147.0 |
| 73 | 5.0 | 14.6 |
| 74 | 200.0 | 540.0 |
| 75 | 250.0 | 590.0 |
| 76 | 3.5 | 6.8 |
| 80 | 20.0 | 53.0 |
| 81 | 10.0 | 27.0 |
| 82 | 300.0 | 729.0 |
| 83 | 25.0 | 52.0 |
| 84 | 2500.0 | 7657.0 |
| 85 | 7.0 | 15.4 |
| 86 | 70.0 | 154.0 |
| 87 | 6.0 | |
| 88 | 20.0 | |
| 89 | 20.0 | |

-continued

| | |
|---|---|
| mitonafide | 20.0 |
| amonafide | 200.0 |

COMPOUND IC50 DATA L1210/.1

| COMPOUND # | L1210 (ng/ml) IC50 | L1210 (nM) IC50 |
|---|---|---|
| 2 | 9.0 | 23.0 |
| 3 | 250.0 | 678.0 |
| 7 | 20.0 | 51.0 |
| 8 | 5.5 | 14.5 |
| 9 | 250.0 | 635.0 |
| 10 | 75.0 | 187.0 |
| 11 | 20.0 | 54.0 |
| 12 | 35.0 | 76.0 |
| 13 | 20.0 | 50.0 |
| 14 | 2500.0 | 6755.0 |
| 15 | 70.0 | 183.0 |
| 16 | 3.0 | 8.0 |
| 17 | 60.0 | 154.0 |
| 19 | 12.0 | 34.0 |
| 20 | 45.0 | 117.0 |
| 21 | 20.0 | 54.0 |
| 22 | 3.5 | 10.0 |
| 23 | 8000.0 | 19277.0 |
| 24 | 300.0 | 676.0 |
| 25 | 2500.0 | 6250.0 |
| 27 | 20.0 | 49.0 |
| 28 | 2.0 | 4.9 |
| 30 | 1.0 | 2.5 |
| 31 | 2.0 | 5.0 |
| 32 | 250.0 | 608.0 |
| 33 | 2.0 | 5.4 |
| 34 | 200.0 | 487.0 |
| 35 | 2.0 | 5.4 |
| 36 | 30.0 | 77.0 |
| 37 | 2.0 | 5.4 |
| 38 | 700.0 | 1872.0 |
| 39 | 10000.0 | 26738.0 |
| 40 | 200.0 | 512.0 |
| 41 | 15.0 | 36.0 |
| 42 | 20.0 | 51.0 |
| 43 | 2500.0 | 6443.0 |
| 44 | 200.0 | 554.0 |
| 45 | 70.0 | 207.0 |
| 46 | 2.5 | 6.8 |
| 47 | .0 | .0 |
| 48 | 75.0 | 174.0 |
| 50 | 2.0 | 5.0 |
| 51 | 200.0 | 462.0 |
| 52 | 100.0 | 243.0 |
| 53 | 3.0 | 8.0 |
| 54 | 1.0 | 2.6 |
| 55 | 35.0 | 91.0 |
| 56 | 20.0 | 50.0 |
| 57 | 70.0 | 189.0 |
| 58 | 700.0 | 1799.0 |
| 59 | 2500.0 | 6739.0 |
| 60 | 22.0 | 57.0 |
| 61 | 200.0 | 485.0 |
| 62 | 250.0 | 524.0 |
| 63 | 200.0 | 498.0 |
| 66 | 6.5 | 18.0 |
| 67 | 20.0 | 61.0 |
| 68 | 250.0 | 791.0 |
| 70 | 8.0 | 20.8 |
| 71 | 20.0 | 52.0 |
| 72 | 60.0 | 126.0 |
| 73 | 2.0 | 5.8 |
| 74 | 70.0 | 169.0 |
| 75 | 200.0 | 472.0 |
| 76 | 1.5 | 2.9 |
| 80 | 20.0 | 53.0 |
| 81 | 15.0 | 40.0 |
| 82 | 200.0 | 486.0 |
| 83 | 150.0 | 312.0 |
| 84 | 2500.0 | 7657.0 |
| 85 | 20.0 | 44.0 |
| 86 | 200.0 | 441.0 |

-continued

| | |
|---|---|
| 87 | 2.5 |
| 88 | 20.0 |
| 89 | 2.5 |
| mitonafide | 20.0 |
| amonafide | 200.0 |

COMPOUNDS WiDr/R IC 50 DATA

| COMPOUND # | MOL WT | WiDr/R (nM) |
|---|---|---|
| 1 | 353 | 100,12,15,60 |
| 2 | 399 | |
| 3 | 369 | |
| 7 | 394 | N.A. |
| 8 | 380 | 9.0 |
| 9 | 394 | 580 |
| 10 | 402 | |
| 11 | 368 | 700 |
| 12 | 460 | 450 |
| 13 | 400 | N.A. |
| 14 | 369 | 27000 |
| 15 | 383 | 1000 |
| 16 | 389 | 100 |
| 17 | 389 | 1200 |
| 19 | 356 | 6 |
| 20 | 384 | 400 |
| 21 | 370 | 280 |
| 22 | 340 | 120,11.5 |
| 23 | 415 | N.A. |
| 24 | 444 | 5000 |
| 25 | 400 | 1100 |
| 27 | 411 | 50 |
| 28 | 411 | 8 |
| 30 | 403 | 18 |

COMPOUND WiDr/S IC 50 DATA

| COMPOUND # | WiDr/S (nM) |
|---|---|
| 1 | 3.5,1.2,10,7 |
| 7 | 700 |
| 8 | 1.8 |
| 9 | 75 |
| 11 | 100 |
| 12 | 800 |
| 13 | N.A. |
| 14 | 9000 |
| 15 | 800 |
| 16 | 4 |
| 17 | 420 |
| 19 | 18 |
| 20 | 80 |
| 21 | 90 |
| 22 | 12,10.5 |
| 23 | 8000 |
| 24 | 900 |
| 25 | 900 |
| 27 | 9 |
| 28 | 600 |
| 30 | 5.5 |

COMPOUNDS 2780/S IC 50 DATA

| COMPOUND # | 2780/S (nM) |
|---|---|
| 1 | 07,.3,.006,30 |
| 2 | 40 |
| 7 | 350 |
| 8 | .01 |
| 9 | 210 |
| 10 | 200 |
| 11 | 2.2 |
| 12 | 0.8 |
| 13 | 0.05 |
| 14 | 35 |
| 15 | 200 |
| 17 | 8 |
| 19 | .017 |
| 20 | 3.5 |

| | |
|---|---|
| 22 | 90 |
| 23 | 1500,1000 |
| 24 | 350,250 |
| 25 | 18,700 |
| 28 | 350 |
| 30 | 150 |
| 53 | 65 |
| 61 | 1800 |

COMPOUND 2780/ADO IC 50 DATA

| COMPOUND # | 2780/ADO (nM) |
|---|---|
| 1 | 17,9,1.6,250 |
| 2 | 250 |
| 7 | 2000 |
| 8 | .035 |
| 9 | 400 |
| 10 | 280 |
| 11 | 35 |
| 12 | 20 |
| 13 | .6 |
| 14 | 180 |
| 17 | 350 |
| 19 | 2 |
| 20 | 2.5 |
| 22 | 300 |
| 23 | 7000,5000 |
| 24 | 2000,600 |
| 25 | 1800,900 |
| 30 | 120 |
| 31 | 300,.35 |
| 53 | 350 |
| 54 | 29 |

COMPOUND IC50 DATA MELANOMA CELLS

| COMPOUND # | UACC375 (ng/ml) IC50 | UACC375 (nM) IC50 |
|---|---|---|
| 1 | 25.0 | 71.0 |
| 2 | 30.0 | 75.0 |
| 3 | 350.0 | 949.0 |
| 7 | 70.0 | 178.0 |
| 8 | 15.0 | 39.0 |
| 9 | 650.0 | 1650.0 |
| 10 | 2000.0 | 4975.0 |
| 11 | 90.0 | 245.0 |
| 12 | 100.0 | 217.0 |
| 13 | 15.0 | 38.0 |
| 14 | 7500.0 | 20325.0 |
| 15 | 200.0 | 522.0 |
| 16 | 7.0 | 18.0 |
| 17 | 200.0 | 514.0 |
| 19 | 15.0 | 42.0 |
| 20 | 60.0 | 156.0 |
| 21 | 60.0 | 162.0 |
| 22 | 20.0 | 59.0 |
| 23 | 7000.0 | 16827.0 |
| 24 | 550.0 | 1239.0 |
| 25 | 550.0 | 1375.0 |
| 27 | 40.0 | 97.0 |
| 28 | 35.0 | 85.0 |
| 30 | 25.0 | 62.0 |
| 31 | 25.0 | 68.0 |
| 32 | 400.0 | 973.0 |
| 33 | 3.5 | 9.5 |
| 34 | 300.0 | 730.0 |
| 35 | 5.5 | 15.0 |
| 36 | 15.0 | 39.0 |
| 37 | 55.0 | 149.0 |
| 38 | 4250.0 | 11363.0 |
| 39 | 4500.0 | 12032.0 |
| 40 | 200.0 | 511.0 |
| 41 | 50.0 | 119.0 |
| 42 | 75.0 | 190.0 |
| 43 | 2500.0 | 6443.0 |
| 44 | 900.0 | 2493.0 |
| 45 | 550.0 | 1622.0 |
| 46 | 52.0 | 141.0 |
| 47 | 5.0 | 10.5 |
| 48 | 200.0 | 463.0 |
| 50 | 50.0 | 125.0 |
| 51 | 5000.0 | 11560.0 |
| 52 | 1000.0 | 2433.0 |
| 53 | 7.0 | 19.0 |
| 54 | 3.0 | 7.8 |
| 55 | 70.0 | 182.0 |
| 56 | 150.0 | 376.0 |
| 57 | 200.0 | 540.0 |
| 58 | 800.0 | 2056.0 |
| 59 | 2800.0 | 7547.0 |
| 60 | 150.0 | 386.0 |
| 61 | 500.0 | 1214.0 |
| 62 | 400.0 | 839.0 |
| 63 | 400.0 | 995.0 |
| 66 | 25.0 | 67.0 |
| 67 | 200.0 | 617.0 |
| 68 | 800.0 | 2532.0 |
| 70 | 20.0 | 52.0 |
| 71 | 70.0 | 182.0 |
| 72 | 150.0 | 314.0 |
| 73 | 15.0 | 44.0 |
| 74 | 450.0 | 1215.0 |
| 75 | 200.0 | 472.0 |
| 76 | 15.0 | 29.0 |
| 80 | 2000.0 | 5333.0 |
| 81 | 800.0 | 2159.0 |
| 82 | 3000.0 | 7290.0 |
| 83 | 300.0 | 624.0 |
| 84 | 6000.0 | 18377.0 |
| 85 | 60.0 | 132.0 |
| 86 | 650.0 | 1433.0 |
| 87 | 10.0 | |
| 88 | 100.0 | |
| 89 | 20.0 | |
| mitonafide | 400.0 | |
| amonafide | 650.0 | |

3) In vitro Tumor Cell Viability Assays Using Sulforhodamine B (SBS)

This assay was performed in accordance with the procedure described by Skehen, et al. in *J. Natl. Cancer Inst.*, 1990, 82, 1107–1112, the contents of which are incorporated herein by reference. This assay was used for adherent cell lines OVCAR 3 and UA375, i.e., human ovarian carcinoma and human malignant melanoma cell lines, respectively.

The assay was performed as follows:

The tumor cells are processed into a single cell suspension. The cells are plated at a concentration of $5-10\times10^3$/mL well into plastic 96 well plates. Growth medium containing RPMI-1640 medium with glutamine, bicarbonate and 5% fetal calf serum is added prior to incubation at 37° C. After incubation for 8 days, the cells are fixed with TCA before washing. Cells attached to the plastic substratum are fixed by gently layering 50 uL of cold 50% TCA (4° C.) on top of the growth medium in each well to produce a final TCA concentration at 10%. The cultures are incubated at 4° C. for one hour and then washed with water several times to remove TCA, growth medium and low molecular weight metabolite and serum protein.

The TCA-fixed cells are stained for 30 minutes with 0.4% (wt/vol) SRB dissolved in 1% acetic acid. At the conclusion of the staining period, the SRB is removed and the cultures are quickly rinsed four times with 10% acetic acid to remove unbound dye. After being rinsed, the cultures are air-dried until no standing moisture is visible. The bound dye is solubilized with 10 nM unbuffered Tris base (pH 10.5) for five minutes on a shaker.

The intensity of the color is proportional to the viable cell numbers and this is quantitated by spectrophotomeric absorbance at 564 nM or a micro ELISA plate reader.

Representative compounds of the present invention were tested using this assay. The results are tabulated hereinbelow:

| COMPOUND IC50 DATA OVARIAN | | |
| --- | --- | --- |
| COMPOUND # | OVCAR3 (ng/ml) IC50 | OVCAR3 (nM) IC50 |
| 1 | 20.0 | 57.0 |
| 2 | 90.0 | 226.0 |
| 3 | 650.0 | 1762.0 |
| 7 | 35.0 | 89.0 |
| 8 | 25.0 | 66.0 |
| 9 | 467.0 | 1185.0 |
| 10 | 6500.0 | 16169.0 |
| 11 | 170.0 | 462.0 |
| 12 | 75.0 | 163.0 |
| 13 | 20.0 | 50.0 |
| 14 | 3500.0 | 9485.0 |
| 15 | 200.0 | 522.0 |
| 16 | 3.5 | 9.0 |
| 17 | 150.0 | 386.0 |
| 19 | 10.0 | 28.0 |
| 20 | 50.0 | 130.0 |
| 21 | 35.0 | 95.0 |
| 22 | 15.0 | 44.0 |
| 23 | 2750.0 | 6627.0 |
| 24 | 2000.0 | 4504.0 |
| 25 | 300.0 | 750.0 |
| 27 | 20.0 | 49.0 |
| 28 | 20.0 | 49.0 |
| 30 | 8.0 | 20.0 |
| 31 | 11.0 | 30.0 |
| 32 | 250.0 | 608.0 |
| 33 | 4.5 | 12.0 |
| 34 | 300.0 | 730.0 |
| 35 | 4.5 | 12.0 |
| 36 | 45.0 | 116.0 |
| 37 | 25.0 | 68.0 |
| 38 | 3000.0 | 8021.0 |
| 39 | 6500.0 | 17380.0 |
| 40 | 250.0 | 639.0 |
| 41 | 90.0 | 214.0 |
| 42 | 80.0 | 203.0 |
| 43 | 1500.0 | 3866.0 |
| 44 | 700.0 | 1939.0 |
| 45 | 825.0 | 2434.0 |
| 46 | 80.0 | 217.0 |
| 47 | 30.0 | 63.0 |
| 48 | 850.0 | 1968.0 |
| 50 | 55.0 | 138.0 |
| 51 | 5000.0 | 11560.0 |
| 52 | 1000.0 | 2433.0 |
| 53 | 0.3 | .8 |
| 54 | 0.5 | 1.3 |
| 55 | 35.0 | 91.0 |
| 56 | 700.0 | 1756.0 |
| 57 | 700.0 | 1887.0 |
| 58 | 3500.0 | 8997.0 |
| 59 | 5500.0 | 14825.0 |
| 60 | 150.0 | 386.0 |
| 61 | 825.0 | 2002.0 |
| 62 | 1375.0 | 2883.0 |
| 63 | 950.0 | 2363.0 |
| 66 | 30.0 | 81.0 |
| 67 | 350.0 | 1070.0 |
| 68 | 2500.0 | 7911.0 |
| 70 | 30.0 | 78.0 |
| 71 | 195.0 | 507.0 |
| 72 | 275.0 | 577.0 |
| 73 | 35.0 | 102.0 |
| 74 | 700.0 | 1889.0 |
| 75 | 400.0 | 945.0 |
| 76 | 90.0 | 176.0 |
| 80 | 100.0 | 267.0 |
| 81 | 200.0 | 540.0 |
| 82 | 2500.0 | 6075.0 |
| 83 | 85.0 | 177.0 |
| 84 | 3000.0 | 9188.0 |
| 85 | 15.0 | 33.0 |
| 86 | 200.0 | 441.0 |
| 87 | 8.0 | |
| 88 | 60.0 | |
| 89 | 8.0 | |
| mitonafide | 2000.0 | |
| amonafide | 700.0 | |

The anti-tumor activity of compounds of the present invention in in vivo mouse murine models were studied.

4) Survival Studies In Tumor-Bearing Mice: 3.1 P-388 Leukemia Models: One million P-388 leukemia cells originally obtained from American Type Culture Collection (Rockville, Md.) are implanted into the peritoneum of adult DBA-2J male mice (Jackson Laboratories, Bar Harbor, Me.). Twenty four hours later, drugs diluted in physiological saline are injected intraperitoneally at a volume of 0.1 mL/10 g body weight. The mice (10/group) are then followed for survival daily and compared to untreated tumor bearing mice. Survival results are converted to a percent increased lifespan over untreated controls (Geran R. I., et al., Cancer Chemo Rep., 3, 1–10, 1972). P-388/Adriamycin Resistant Cells: The same protocol as above was used for these studies with a multidrug resistant P-388 cell line developed in vivo by and supplied by Dr. Randall Johnson (Johnson R. K., et al., Cancer Treat Rep 62, 1535–1547, 1978). Colon-38: Freshly-harvested 20–30 mg pieces of viable colon-38 adenocarcinoma are injected into the right front flank of C57/B1 adult mice. These tumors are allowed to grow for three days. Drugs are injected intraperitoneally on days three and six after inoculation at a volume of 0.1 mL/10 g body weight. The perpendicular widths of the tumors are measured by caliper thrice weekly and converted to an estimated tumor mass according to the formula:

$$\frac{1 \times W^2}{2} = \text{grams of tumor.}$$

wherein

W=width of tumor l=length of tumor

Tumor growth delay is calculated as the difference in days for tumors in treated mice to reach an estimated mass 750 mg or 1.5 g compared to that in untreated controls:

Days to reach 750 mg (Treated−Control)=Days of Tumor Growth Delay

Corbett, T. H., et al., Cancer Chemo Rep., 5 (1975). Mammary 16-C Adenocarcinoma and M5–76 Sarcoma: Chunks of tumor (20–50 mg) are subcutaneously implanted into the flank of B6C3F1 female mice. Drugs (10–45 mg/kg) are dissolved in saline and injected intraperitoneally every four days for three times starting one day after tumor implantation. Tumors are measured bidimensionally as described above and tumor growth delay is calculated at times to reach 1.5 and 3.0 g of tumor mass.

Using the various in vivo mouse models and the procedures described hereinabove, the anti-tumor activity of compound 1 was tested. The results are shown in Table 3 hereinbelow.

TABLE 3

| | | | | Comparative Activity From the Literature | | |
|---|---|---|---|---|---|---|
| Tumor Cell Line | Model | Drug Regimen (mg/kg × 15 days) | Experimental Activity | Amonafide | Doxorubicin | T-AMSA |
| P-388 lymphocytic leukemia | $10^6$ cells in DBA mice | 1,5,9 | 79 ILS* | 99 ILS | 164 ILS | 124 ILS |
| P-388/ADR (adriamycin-resistant) | $10^6$ cells in DBA mice | 1,5,9 | 33 ILS | 35 ILS | 18 ILS | unk.** |
| B16 melanocytic melanoma | $10^6$ $C_{57}/B1$ mice | 1,5,9 | 67 TGI*** | 23 | | |
| Colon-38 Adenocarcinoma | 20 mg implants in $C_{57}B$/mice | 3,6 | 6 days TT | <7 days | 10 days | 2 days |
| 16-C Mammary Adenocarcinoma | (Southern Research Institute) | 1,5,9 | 7 days TT | 7 days | unk. | unk. |
| M5-76 Sarcoma | (Southern Research Institute) | 1,5,9 | 7 days | 7 days | unk. | unk. |

*ILS = Percentage Increased Lifespan
TT = Days of Tumor Growth Delay
**Unknown
***TGI = % Tumor Growth Inhibition based on tumor size $(L \times W^2)/2$ Evaluation of Tumor Growth The appearance of tumors of a threshold size, and the growth in these tumors in groups of 10 mice (B6C3F0, 18–22 g) implanted with $5 \times 10^6$ M5076 carcinoma cells compared to the tumor appearance and growth in samples treated with NSC308847 and Compound 1 are shown in sensitivity indicates tumor cell survival of less than 50% of control colony-forming cells. Each tumor sample is analyzed in three different petri dishes (i.e., n=3 for each sample).

TABLE 4

CYTOTOXIC ACTIVITY FOR COMPOUND 1 IN FRESH HUMAN TUMORS[1]

| | Compound 1 Sensitive | | | | Doxorubicin Sensitive[2] | | | |
|---|---|---|---|---|---|---|---|---|
| Human Tumor Type | No. of Samples | <30–50% Control | <30% of Control | Overall Response | No. of Samples | <30–50% Control | <30% of Control | Overall Response |
| Breast | 11 | 3 | 4 | 64% | 58 | 6 | 5 | 19% |
| Colon/Rectum | 7 | 8 | 1 | 14% | 17 | 3 | 2 | 29% |
| Lung | 6 | 2 | 1 | 50% | 12 | 1 | 1 | 17% |
| Melanoma | 11 | 4 | 3 | 64% | 10 | 0 | 0 | 0 |
| Ovary | 8 | 3 | 1 | 50% | 36 | 2 | 7 | 25% |
| Total | 43 | 12 | 10 | 51% | 133 | 12 | 15 | 20% |

[1]Fresh human tumor specimens disaggregated to single cell suspensions and exposed to .001 ug/mL of drug continuously. Percent survival represents the fraction of tumor colonies (>60 uM size) obtained after drug treatment compared to untreated cells of the same tumor. Overall sensitivity indicates tumor cell survival of less than 50% of control colony-forming cells. Each tumor sample is analyzed in three different petri dishes (i.e., n = 3 for each sample).
[2]Doxorubicin tumors were from different patients.

Table 3. The values are median values for the samples, and show the weight of the tumor with time.

These studies confirm that the compound of this invention delays the appearance of tumors at the threshold level significantly over the control and similarly to the comparative drug (amonafide) at the same dose level, and significantly reduces the tumor growth at lower dose rates.

The cytotoxic activity of compounds of the present invention in fresh human tumors was also tested. The protocol is as follows:

Fresh human tumor specimens disaggregated to single cell suspensions and exposed to 0.001 ug/mL of drug continuously. Percent survival represents the fraction of tumor colonies (>60 uM size) obtained after drug treatment compared to untreated cells of the same tumor. Overall The data in Table 4 results from testing on a group of human tumors, totalling 43 separate human cancers. The overall response rate in these 43 samples was 51% using a continuous drug concentration of 0.001 ug/mL). These data represent a very high level of in vitro activity; some of the highest levels of activity were seen in typically adriamycin-responsive tumors such as breast cancer and ovarian cancer. Unexpected was the level of activity of compound 1 against melanomas (64%). Melanoma is widely known to be an extremely chemoresistant disease with most standard agents.[5] The data shows that compared to doxorubicin (overall response rate of 20%), compound 1 was significantly superior.

[5] Luce, J. K., *Seminar Oncol*, 2, 179–185 (1975).

Other compounds were tested for the in vitro cytotoxic activity in accordance with the procedure described hereinabove with respect to Table 2. The results are indicated hereinbelow in Table 5.

TABLE 5

IN VITRO CYTOTOXIC ACTIVITY
IC$_{50}$ VALUES (ng/ML CONTINUOUS EXPOSURE)*

| Compound # | 8226 Myeloma Sensitive | Cells Resistant | L1210 Sensitive | Leukemia Cells Resistant |
|---|---|---|---|---|
| 1 | 10 | 30 | 2.8 | 2.5 |
| 13 | 5 | 10 | 2.5 | 2.9 |
| 14 | >100 | >100 | 5,000 | >5,000 |

*Measured by MTT dye assay (N.C.I. Method).

As indicated hereinabove, one of the goals of the present inventors was to find low relative cytotoxic effects in normal heart cells. The cardiotoxicity of compounds of the present invention was evaluated using the following assay.

In Vitro Cardiotoxicity Methods

This assay is conducted in accordance with Dorr, et al. in *Cancer Research*, 1988, 48, 5222–5227. Hearts from 1–2 days old Sprague-Dawley rats are minced into 1 mm$^2$ fragments. Cell suspensions were made therefrom by serial digestion with 0.24% trypsin. The digestions were collected, pooled, washed twice in Liebovitz's M3 medium, and plated at 3–4×10$^7$ cells/150 cm$^2$ culture flask for rapid fibroblast attachment. After two hours, the resultant myocyte enriched supernatant was poured off and plated in 24 well Primaria plates at a density of about 1×10$^6$ cells/well. Three days after plating, drugs in the M3 medium were added to the myocyte cultures for six hours at concentrations of 0.1 to 10 ug/mL (0.18 to 18 um). At the end of that time, the cells were rinsed three times with M3 media to remove free drug. Fresh media was added to the cells which are incubated for three days at 37° C. in a 5% CO$_2$ incubator.

The myocytes were then harvested. Cells were rinsed with phosphate-buffered saline and 5% trichloracetic acid was added to each well to lyse the cells and extract the ATP. Precipitated protein was solubilized with 0.1% Triton X-100 in 0.5N NaOH. The ATP levels were measured photometrically using a standard firefly luciferein-luciferase bioluminescent assay.

Protein content was determined using the Bio-Rad method with bovine serum albumin dissolved in cell solubilization solution as a standard.

The ATP/protein ratio following drug treatment was calculated and compared with values of untreated (control) plates. The myocyte cytotoxicity (Cardiotoxicity) is defined as $$\frac{ATP/\text{protein (treated)}}{ATP/\text{protein (control)}} \times 100\%$$

The results are summarized hereinbelow:

| COMPOUND CARDIOTOXICITY | |
|---|---|
| COMPOUND # | IC$_{50}$ (ug/mL) |
| Amonafide | 15.5 |
| 1 | 0.7 |
| 2 | 3.45 |
| 3 | 10 |
| 7 | 4.0 |
| 8 | 0.35 |
| 9 | 3.45 |
| 10 | 15 |
| 11 | 4.2 |
| 12 | 4.1 |
| 13 | 0.26 |
| 14 | >>30 |
| 15 | 30 |
| 16 | 0.51 |
| 17 | 4.2 |
| 18 | 0.5 |
| 19 | 0.6 |
| 20 | 10 |
| 21 | 0.75 |
| 22 | 2.4 |
| 23 | >>20 |
| 24 | >10 |
| 25 | >>20 |
| 28 | 2.4 |
| 29 | 0.3 |
| 30 | 0.38 |
| 33 | 0.16 |
| 35 | 0.72 |
| 37 | 0.55 |
| 38 | >10 |
| 40 | 22 |
| 41 | 6.4 |
| 42 | 2.8 |
| 43 | >10 |
| 44 | >10 |
| 45 | >10 |
| 46 | 0.35 |
| 47 | 3.0 |
| 48 | 2.9 |
| 50 | 0.37 |
| 51 | 15.0 |
| 52 | >>10 |
| 53 | 0.66 |
| 54 | 0.3 |
| 55 | 1.5 |
| 56 | 2.2 |
| 57 | 6.0 |
| 58 | 3.2 |
| 59 | >>50 |
| 61 | 5 |
| 62 | 100 |
| 63 | >>10 |
| 66 | 0.35 |
| 67 | 2.0 |
| 68 | 30 |
| 70 | 3.5 |
| 72 | 0.35 |
| 73 | 0.53 |
| 74 | >>10 |
| 75 | >>10 |
| 76 | 1.65 |
| 80 | 2.85 |
| 81 | 3.0 |
| 82 | 5.3 |
| 83 | 2.3 |
| 84 | >>10 |
| 85 | 0.3 |
| 86 | >>10 |
| 87 | 0.7 |
| 88 | 0.04 |

The cytotoxicity results of the various assays are summarized hereinbelow.

| | | | | CYTOTOXICITY RESULTS | | | | |
|---|---|---|---|---|---|---|---|---|
| # | MOL WT | UACC375 (ng/ml) IC50 | OVCAR3 (ng/ml) IC50 | L1210 (ng/ml) IC50 | AVEIC50 | STD DEV | RL1210 (ng/ml) IC50 | RATIO (R/S) | HEART CELL IC50 (ug/ml × hr) |
| 1 | 353 | 25 | 20 | 2.5 | 15.83 | 9.65 | 2.5 | 1 | 0.7 |
| 2 | 399 | 30 | 90 | 9 | 43 | 34.32 | 20 | 2.22 | 3.45 |
| 3 | 369 | 350 | 650 | 250 | 416.67 | 169.97 | 250 | 1 | 10 |
| 7 | 394 | 70 | 35 | 20 | 41.67 | 20.95 | 20 | 1 | 4 |
| 8 | 380 | 15 | 25 | 5.5 | 15.17 | 7.96 | 4.5 | 0.82 | 0.35 |
| 9 | 394 | 650 | 467 | 250 | 455.67 | 163.5 | 240 | 0.96 | 3.45 |
| 10 | 402 | 2000 | 6500 | 75 | 2850.33 | 2692.3 | 720 | 9.6 | 15 |
| 11 | 368 | 90 | 170 | 20 | 93.33 | 61.28 | 30 | 1.5 | 4.2 |
| 12 | 460 | 100 | 75 | 35 | 70 | 26.77 | 65 | 1.86 | 4.1 |
| 13 | 400 | 15 | 20 | 20 | 18.33 | 2.36 | 8 | 0.4 | 0.26 |
| 14 | 369 | 7500 | 3500 | 2500 | 4500 | 2160.25 | 2500 | 1 | >30 |
| 15 | 383 | 200 | 200 | 70 | 156.67 | 61.28 | 90 | 1.29 | 30 |
| 16 | 389 | 7 | 3.5 | 3 | 4.5 | 1.78 | 10 | 3.33 | 0.55 |
| 17 | 389 | 200 | 150 | 60 | 136.67 | 57.93 | 80 | 1.33 | 4.2 |
| 18 | 447 | | | 200 | 200 | 0 | | 0 | |
| 19 | 356 | 15 | 10 | 12 | 12.33 | 2.05 | 25 | 2.08 | 0.6 |
| 20 | 384 | 60 | 50 | 45 | 51.67 | 6.24 | 42 | 0.91 | 10 |
| 21 | 370 | 60 | 35 | 20 | 38.33 | 16.5 | 50 | 2.5 | 0.75 |
| 22 | 340 | 20 | 15 | 35 | 12.83 | 6.91 | 7 | 2 | 24 |
| 23 | 415 | 7000 | 2750 | 8000 | 5916.67 | 2276.08 | 8000 | 1 | >20 |
| 24 | 444 | 550 | 2000 | 300 | 950 | 749.44 | 650 | 2.17 | >10 |
| 25 | 400 | 550 | 300 | 2500 | 1116.67 | 983.47 | 490 | 0.2 | >20 |
| 27 | 411 | 40 | 20 | 20 | 26.67 | 9.43 | 90 | 4.5 | 0.020 |
| 28 | 411 | 35 | 20 | 2 | 19 | 13.49 | 7 | 3.5 | 2.4 |
| 30 | 403 | 25 | 8 | 1 | 11.33 | 10.08 | 1.1 | 1.1 | 0.38 |
| 31 | 369 | 25 | 11 | 2 | 12.67 | 9.46 | 5.8 | 2.9 | 1.2 |
| 32 | 411 | 400 | 250 | 250 | 300 | 70.71 | 230 | 0.92 | >10 |
| 33 | 369 | 3.5 | 4.5 | 2 | 3.33 | 1.03 | 2.9 | 1.45 | 0.16 |
| 34 | 411 | 300 | 300 | 200 | 266.67 | 47.14 | 200 | 1 | >10 |
| 35 | 369 | 5.5 | 4.5 | 2 | 4 | 1.47 | 2.5 | 1.25 | 0.72 |
| 36 | 389 | 15 | 45 | 30 | 30 | 12.25 | 25 | 0.83 | 32.22 |
| 37 | 369 | 55 | 25 | 2 | 27.33 | 21.7 | 10 | 5 | 0.55 |
| 38 | 374 | 4250 | 3000 | 700 | 2650 | 1470.26 | 1000 | 1.43 | >10 |
| 39 | 374 | 4500 | 6500 | 10000 | 7000 | 2273.03 | 10000 | 1 | >10 |
| 40 | 391 | 200 | 250 | 200 | 216.67 | 23.57 | 200 | 1 | 22 |
| 41 | 420 | 50 | 90 | 15 | 51.67 | 30.64 | 23 | 1.53 | 6.4 |
| 42 | 395 | 75 | 80 | 20 | 58.33 | 27.18 | 22 | 1.1 | 2.8 |
| 43 | 386 | 2500 | 1500 | 2500 | 2166.67 | 471.4 | 6000 | 2.4 | >10 |
| 44 | 361 | 900 | 700 | 200 | 600 | 294.39 | 200 | 1 | >10 |
| 45 | 339 | 550 | 825 | 70 | 481.67 | 311.99 | 50 | 0.71 | >10 |
| 46 | 369 | 52 | 80 | 2.5 | 44.83 | 32.04 | 10 | 4 | 0.35 |
| 47 | 477 | 5 | 30 | 0.02 | 11.67 | 13.12 | 0.02 | 1 | 3 |
| 48 | 432 | 200 | 850 | 75 | 375 | 339.73 | 200 | 2.67 | 2.9 |
| 50 | 400 | 50 | 55 | 2 | 35.67 | 23.89 | 8 | 4 | 0.37 |
| 51 | 433 | 5000 | 5000 | 200 | 3400 | 2262.74 | 240 | 1.2 | 15.1 |
| 52 | 411 | 1000 | 1000 | 1000 | 100 | 700 | 424.26 | 1000 | >10 |
| 53 | 371 | 7 | 0.3 | 3 | 3.43 | 2.75 | 2.5 | 0.83 | 0.66 |
| 54 | 305 | 3 | 0.5 | 1 | 1.5 | 1.00 | 1.5 | 1.5 | 0.3 |
| 55 | 305 | 70 | 35 | 35 | 46.67 | 16.5 | 60 | 1.71 | 1.5 |
| 56 | 399 | 150 | 700 | 20 | 290 | 294.73 | 27 | 1.35 | 2.2 |
| 57 | 371 | 200 | 700 | 70 | 323.33 | 271.58 | 70 | 1 | 6 |
| 58 | 309 | 800 | 3500 | 700 | 1666.67 | 1297.01 | 240 | 0.34 | 3.2 |
| 59 | 371 | 2800 | 5500 | 2500 | 3600 | 1349.07 | 2000 | 0.8 | >50 |
| 60 | 389 | 150 | 150 | 22 | 107.33 | 60.34 | 23 | 1.05 | 0.3 |
| 61 | 412 | 500 | 825 | 200 | 508.33 | 255.22 | 210 | 1.05 | 5 |
| 62 | 477 | 400 | 1375 | 250 | 675 | 498.75 | 250 | 1 | 100 |
| 63 | 402 | 400 | 950 | 200 | 516.67 | 317.1 | 500 | 2.5 | >10 |
| 66 | 371 | 25 | 30 | 6.5 | 20.5 | 10.11 | 15 | 2.31 | 0.35 |
| 67 | 327 | 200 | 350 | 20 | 190 | 134.91 | 55 | 2.75 | 2 |
| 68 | 316 | 800 | 2500 | 250 | 1183.33 | 957.72 | 250 | 1 | 30 |
| 70 | 385 | 20 | 30 | 8 | 19.33 | 8.99 | 20 | 2.5 | 3.5 |
| 71 | 385 | 70 | 195 | 20 | 95 | 73.6 | 65 | 3.25 | 6.3 |
| 72 | 477 | 150 | 275 | 60 | 161.67 | 88.16 | 70 | 1.17 | 0.35 |
| 73 | 343 | 13 | 35 | 2 | 17.33 | 13.57 | 5 | 2.5 | 0.53 |
| 74 | 371 | 450 | 700 | 70 | 406.67 | 259.02 | 200 | 2.86 | >10 |
| 75 | 424 | 200 | 400 | 200 | 266.67 | 94.28 | 250 | 1.25 | >10 |
| 76 | 512 | 15 | 90 | 1.5 | 35.5 | 38.93 | 3.5 | 2.31 | 1.65 |
| 80 | 375 | 2000 | 100 | 20 | 706.67 | 915.11 | 20 | 1 | 2.85 |
| 81 | 371 | 800 | 200 | 15 | 338.33 | 335.07 | 10 | 0.67 | 3.0 |
| 82 | 412 | 3000 | 2500 | 200 | 1900 | 1219.29 | 300 | 1.5 | 5.3 |
| 83 | 481 | 300 | 85 | 150 | 178.33 | 90.03 | 25 | 0.17 | 2.3 |
| 84 | 327 | 6000 | 3000 | 2500 | 833.33 | 1545.6 | 2500 | 1 | >10 |
| 85 | 454 | 60 | 15 | 20 | 31.67 | 20.14 | 7 | 0.35 | 0.3 |
| 86 | 454 | 650 | 200 | 200 | 350 | 212.13 | 70 | 0.35 | >10 |
| 87 | 406 | | | | | | | | 0.7 |

| | | | | | | | |
|---|---|---|---|---|---|---|---|
| mitonafide | 400 | 2000 | 20 | 806.67 | 857.96 | 20 | 1 |
| amonafide | 650 | 700 | 200 | 516.67 | 224.85 | 200 | 1 |

Additional studies of representative compounds of the present invention are indicated in the following three tables. The test systems include growth inhibition studies with human murine tumors (Table 6) as well as a cardiotoxicity assessment in neonatal rat heart myocytes (Table 7). The methodology for the antitumor studies involves the MTT dye assay for the L1210 murine Leukemia cells (parental and multidrug resistant [MDR], subline, RL-1210) (Method Reference: Alley MC, et al.: Cancer Res 48: 589–601, 1988) and the sulforhodamine B protein assay for the human melanoma cell line, UACC 375, and the human ovarian cancer cell line, OVCAR-3 (Method Reference: Skehan P, et al.: J. Natl. Cancer Inst. 82: 1107–1112, 1990), the contents of all of which are incorporated by reference.

In addition to these findings, representative compounds of the present invention also have been screened with respect to additional sensitive and multidrug resistant human tumor cell lines such as A549 lung cancer, MCF-7 and MCF-7 doxorubicin resistant (MCF 7/D40) breast cancer in accordance with the procedures described in Skehan, P. et al. in J. Natl. Cancer Inst 1990, 82(13), 1107–1112; the contents of which are incorporated by reference. Briefly, the assay involves fixing 1–5×10$^6$ cells/well with trichloroacetic acid followed by 30 minutes of staining with 0.4% (wt/vol) of sulforhodamine B in 1% acetic acid. The cells are then washed 4 times in 1% acetic acid to remove unbound dye. Protein-bound dyes are then extracted with 10 mM unbuffered Tris [Tris(hydroxymethyl)amino methane] base and the optical density of protein is measured at 564 nm. The amount of protein following drug treatment is divided by that in untreated control wells and multiplied×100 to generate a % growth inhibition. The results of representative examples of the present application are shown in Table 8.

TABLE 6

ANTI-TUMOR ACTIVITY FOR COMPOUNDS 96 THROUGH 119 IN VITRO (IC$_{50}$ μg · mL)

| | Cell Lines | | | | |
|---|---|---|---|---|---|
| Number | L-1210 | RL-1210 | UACC375 | OVCAR-3 | Mean (SD) |
| 96 | 200 | 200 | 250 | 150 | 200 (40.8) |
| 97 | NA | 7.0 | 30 | 15 | 17.3 (11.6) |
| 100 | 40 | 25 | 100 | 80 | 61.3 (34.7) |
| 101 | 20 | 25 | 65 | 45 | 38.8 (20.6) |
| 102 | 15 | 20 | 30 | 25 | 22.5 (6.5) |
| 103 | 5 | 7 | 20 | 20 | 13 (8.1) |
| 104 | 0.1 | 0.6 | 15 | 15 | 7.7 (8.5) |
| 105 | 8.0 | 30 | 30 | 25 | 23.3 (10.4) |
| 106 | 200 | 200 | 200 | 200 | 200 — |
| 107 | 1,000 | 700 | 400 | 1,000 | 775 (287) |
| 112 | 10 | 10 | 7.0 | 9.0 | 9 (1.4) |
| 113 | 5.5 | 5.0 | 4.0 | 4.5 | 4.75 (.6) |
| 114 | 70 | 70 | 40 | 60 | 60 (14.1) |
| 117 | 3.0 | 3.0 | 6.0 | NA | 4.0 (1.7) |
| 118 | 200 | 200 | 200 | NA | 200 — |
| 119 | 100 | 200 | 90 | NA | 130 (60.8) |

NA = Results not available yet.

TABLE 7

ADDITIONAL CARDIOTOXICITY OF REPRESENTATIVE COMPOUNDS

| Number | Myocyte IC$_{50}$ (ug/mL) | Mean Tumor Cell IC$_{50}$* (ng/mL) | Heart/Tumor IC$_{50}$ Ratio |
|---|---|---|---|
| 96 | 5.0 | 200 | 25 |
| 97 | 0.4 | 17.3 | 23.1 |
| 100 | 0.9 | 61.3 | 14.7 |
| 101 | 0.5 | 38.8 | 12.8 |
| 102 | 0.3 | 22.5 | 13.3 |
| 103 | 0.38 | 13.0 | 29.2 |
| 104 | 2.7 | 7.7 | 350.6 |
| 105 | .065 | 23.3 | 2.79 |
| 117 | 0.18 | 4.0 | 45 |

*OVCAR-3 ovary, UACC375 Melanoma, L-1210 leukemia, L-1210$_{MDR}$ multidrug resistant.

TABLE 8

ANTI-TUMOR ACTIVITY OF COMPOUNDS 96 THROUGH 121 IN HUMAN A549 LUNG AND MCF7 BREAST CANCER CELL LINES IN VITRO (μM)

| Number | A549 | MCF-7 | MCF-7/D40 | Fold-Resistance (MCF$_{D40}$/MCF-7) |
|---|---|---|---|---|
| 96 | 0.6 | — | — | — |
| 97 | 0.22 | — | — | — |
| 101 | .033 | — | — | — |
| 103 | .0036 | — | — | — |
| 104 | 0.00064 | — | — | — |
| 105 | .013 | — | — | — |
| 106 | .001 | 0.1 | 0.11 | 1.1 |
| 107 | 0.9 | 0.89 | 0.88 | 0.98 |
| 112 | — | .013 | .0087 | 0.16 |
| 113 | .002 | .018 | .011 | — |
| 114 | .015 | — | .084 | — |
| 117 | .015 | .0135 | .084 | 6.22 |
| 118 | 0.18 | 0.9 | 1.1 | 1.22 |
| 119 | .075 | 0.31 | 1.05 | 3.38 |
| 121 | .0095 | .71 | 1.0 | 1.41 |

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A compound of the formula:

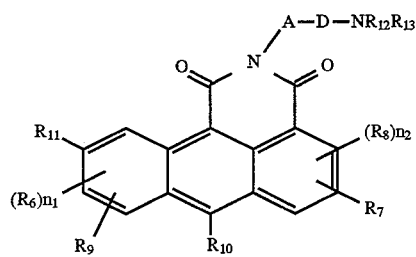

or pharmaceutically acceptable salts thereof wherein
R$_6$ is hydrogen, lower alkyl, aryl, lower alkanoyl, formyl, halo, nitro, NR$_2$R$_3$, heterocyclic lower alkyl, lower alkyl sulfonyl, hydrazine, OR$_1$, lower alkanoylamino, SR$_1$, cyano, CO$_2$H, aminoloweralkyleneoxy, monoloweralkylaminoloweralkyleneoxy, diloweralkylaminoloweralkyleneoxy, SO$_2$NR$_1$R$_2$, amino lower alkanoyl, or CONR$_1$R$_2$;

R$_8$ and R$_{10}$ are independently, hydrogen, lower alkyl, aryl, lower alkanoyl, formyl, halo, NR$_2$R$_3$, heterocyclic lower alkyl, lower alkyl sulfonyl, hydrazino, OR$_1$, SR$_1$, lower alkanoylamino, cyano, CO$_2$H, SO$_2$NR$_1$R$_2$, CONR$_1$R$_2$ or diloweralkylamino lower alkylene amino;

R$_1$ is hydrogen, lower alkyl, aryl lower alkyl, aryl, formyl or lower alkanoyl;

R$_2$ and R$_3$ are independently hydrogen, lower alkyl, aryl, aryl lower alkyl, formyl, lower alkanoyl, monoloweralkyl amino lower alkylene, diloweralkylamino lower alkylene or hydroxy lower alkyl;

R$_9$, R$_{11}$, and R$_7$ are independently hydrogen or loweralkyl;

A is (CR$_4$R$_5$)n$_3$, lower cycloalkylene or arylene or a chemical bond;

each R$_4$ and R$_5$ are independently hydrogen or lower alkyl;

R$_{12}$ and R$_{13}$ are independently hydrogen or lower alkyl which is unsubstituted or substituted with hydroxy, mercapto, lower alkoxy, lower alkylcarbonyloxy, carboxy, or carboloweralkoxy or R$_{12}$ and R$_{13}$ taken together with the nitrogen to which they are attached form a 3–6 membered heterocyclic ring with said ring containing a nitrogen as a ring heteroatom and optionally an O or S heteroring atom;

D is a chemical bond, or taken together with forms a 5 or 6-membered heterocyclic ring, with said ring containing a nitrogen ring heteroatom and optionally an O or S ring heteroatom;

n$_1$ and n$_2$ are independently 0, 1 or 2; and n$_3$ is 0, 1, 2, 3, 4 or 5.

2. The compound according to claim 1 wherein R$_9$, R$_{11}$, R$_{10}$, R$_7$ and R$_8$ are hydrogen.

3. The compound according to claim 1 wherein R$_6$ is hydrogen, amino, nitro, hydroxy, halo, loweralkanoylamino, sulfonamido, amino lower alkanoyl, or lower alkoxy and n$_1$ is 1.

4. The compound according to claim 1 wherein R$_8$ is hydrogen, halo, hydroxy, or lower alkyl.

5. The compound according to claim 1 wherein R$_6$ is hydrogen.

6. The compound according to claim 1 wherein R$_{10}$ is hydrogen or halo.

7. The compound according to claim 1 wherein R$_8$ is hydrogen.

8. The compound according to claim 1 wherein R$_{10}$ is hydrogen.

9. The compound according to claim 1 wherein R$_8$ and R$_{10}$ are hydrogen.

10. The compound according to claim 1 wherein R$_8$ and R$_{10}$ are hydrogen, R$_6$ is hydrogen, nitro, amino, loweralkyl, cyano, hydroxy, halo, sulfonamido, loweralkanoylamino, or lower alkoxy and n$_1$ is 1.

11. The compound according to claim 10 wherein R$_6$ is hydrogen, nitro, amino, hydroxy, methoxy, ethoxy, methyl, aminoacetyl, fluoro, t-butylcarbonylamino, methyl, cyano, chloro or iodo.

12. The compound according to claim 1 wherein R$_8$ and R$_6$ are hydrogen.

13. The compound according to claim 1 wherein R$_{10}$ is hydrogen, lower alkyl, halo, hydroxy, lower alkoxy, lower alkylthio, lower alkanoylamino, diloweralkylamino lower alkylene amino, amino or aziridino lower alkylene.

14. The compound according to claim 1 wherein R$_8$ and R$_6$ are hydrogen and R$_{10}$ is hydrogen, lower alkyl, halo, hydroxy, lower alkoxy, lower alkylthio, lower alkanoyl amino, diloweralkyl amino lower alkylene amino, amino or aziridino lower alkylene.

15. The compound according to claim 14 in which R$_{10}$ is hydrogen, hydroxy, methoxy, methyl, chloro, bromo, methylthio, acetyl amino, aziridino-ethylene, dimethylaminoethyleneamino.

16. The compound according to claim 1 in which R$_8$ is hydrogen, lower alkyl, lower alkanoylamino, nitro, amino, halo, diloweralkylamino lower alkylene amino, or lower alkylsulfonyl, and n$_2$ is 1.

17. The compound according to claim 1 in which R$_6$ and R$_{10}$ are hydrogen.

18. The compound according to claim 1 in which R$_6$ and R$_{10}$ are hydrogen and R$_8$ is hydrogen, lower alkyl, lower alkanoylamino, nitro, amino, halo, diloweralkylamino lower alkylene amino, or lower alkylsulfonyl, and n$_2$ is 1.

19. The compound according to claim i wherein A is (CR$_4$R$_5$)n$_3$ and D is a chemical bond.

20. The compound according to claim 19 wherein n$_3$ is 2–4.

21. The compound according to claim 19 wherein R$_4$ and R$_5$ are independently hydrogen and n$_3$ is 2–4.

22. The compound according to claim 1 wherein R$_{12}$ and R$_{13}$ are hydrogen or lower alkyl unsubstituted or substituted with hydroxy.

23. The compound according to claim 1 wherein R$_{12}$ and R$_{13}$ are the same.

24. The compound according to claim 1 wherein D taken together with NR$_{12}$ form a 5 or 6-membered nitrogen containing ring.

25. The compound according to claim 1 wherein ADNR$_{12}$R$_{13}$ is

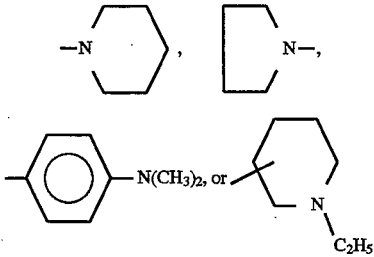

pyridyl, pyridyl lower alkylene, aziridino lower alkylene, piperazino lower alkylene, pyrrolidyl lower alkylene, N-lower alkyl pyrrolidino lower alkylene, or morpholino lower alkylene.

26. The compound according to claim 25 in which alkylene contains 1 or 2 carbon atoms.

27. The compound according to claim 1 in which ADNR$_{12}$R$_{13}$ is CH$_2$CH$_2$N(CH$_3$)$_2$, piperidinoethylene pyrrolidinoethylene, N-ethyl-3-piperidino, 2-pyridylmethylene, 3-pyridylmethylene, N-ethyl-2-pyrrolidino-methylene, N-methyl-2-pyrrolidinoethylene, 2-N-piperazino-ethylene, or aziridinoethylene.

28. The compound according to claim 1 in which ADNR$_{12}$R$_{13}$ is CH$_2$CH$_2$N(CH$_3$)$_2$.

29. The compound according to claim 1 in which n$_1$ and n$_2$ are 1, R$_6$ is hydrogen, R$_8$ is hydrogen, halo, hydroxy, lower alkoxy, loweralkyl, or diloweralkyl amino lower alkylene amino, and R$_{10}$ is hydrogen, lower alkoxy, halo or amino.

30. The compound according to claim 29 in which $R_8$ is hydrogen, chloro, hydroxy, methoxy, or $(CH_3)_2N(CH_2)_2NH$ and $R_{10}$ is hydrogen, methoxy or amino.

31. The compound according to claim 1 in which $R_8$ is substituted on the 5- or 6-position.

32. The compound according to claim 29 in which $R_8$ is 6-halo, 6-hydroxy, 6-lower alkoxy or 6-diloweralkyl amino lower alkylene amino or 5-acetamido.

33. The compound according to claim 32 in which $R_8$ is 6-loweralkoxy.

34. The compound according to claim 33 in which $R_8$ is 6-ethoxy.

35. A compound of the formula:

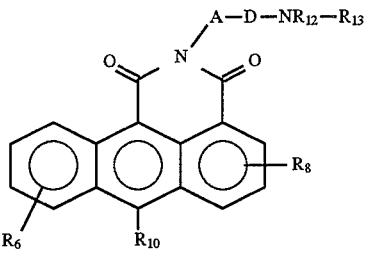

or pharmaceutically acceptable salts thereof wherein $R_8$ is aminoloweralkyleneoxy, monoloweralkylaminoloweralkyleneoxy, diloweralkylaminoloweralkyleneoxy, or

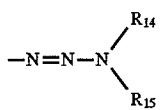

$R_6$ and $R_{10}$ are independently hydrogen, lower alkyl, aryl, lower alkanoyl, formyl, halogen, hydrazino, nitro, $NR_2R_3$, heterocyclic lower alkyl, lower alkyl sulfonyl, $OR_1$, aminoloweralkyleneoxy, monoloweralkylaminoloweralkyleneoxy, diloweralkylaminoloweralkyleneamino, loweralkanoylamino,

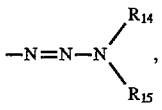

$SR_1$, hydroxy, methoxy, cyano, $CO_2H$, $SO_2NR_1R_2$, or $CONR_1R_2$;

$R_1$ is hydrogen, lower alkyl, aryl lower alkyl, aryl, formyl or lower alkanoyl;

$R_2$ and $R_3$ are independently hydrogen, lower alkyl, aryl, aryl lower alkyl, formyl, lower alkanoyl, monoloweralkyl amino lower alkylene, diloweralkylamino lower alkylene or hydroxy lower alkyl amino;

A is $(CR_4R_5)n_3$, lower cycloalkylene or arylene or a chemical bond;

each $R_4$ and $R_5$ are independently hydrogen or lower alkyl;

$R_{14}$ and $R_{15}$ are independently hydrogen or loweralkyl;

$n_3$ is 0, 1, 2, 3, 4 or 5;

$R_{12}$ and $R_{13}$ are independently hydrogen, or lower alkyl which is unsubstituted or substituted with hydroxy, mercapto, lower alkoxy, lower alkylcarbonyloxy, carboxy, or carboloweralkoxy or $R_{12}$ and $R_{13}$ taken together with the a nitrogen to which they are attached form a 3–6 membered heterocyclic ring with said ring containing a nitrogen ring heteroatom and optionally an O or S ring heteroatom; and D is a chemical bond, or taken together with $NR_{12}$ forms a 5 or 6-membered heterocyclic ring with said ring containing nitrogen ring heteroatom and optionally an O or S ring heteroatom.

36. A compound of the formula

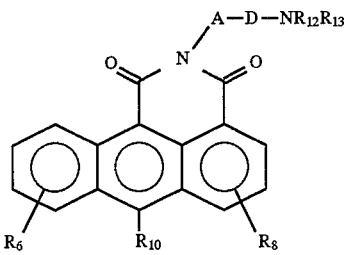

or pharmaceutically acceptable salts thereof wherein $R_6$ is aminoloweralkyleneoxy, monoloweralkylaminoloweralkyleneoxy, diloweralkylaminoloweralkyleneoxy, or

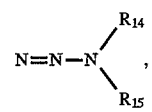

$R_9$ and $R_{10}$ are independently hydrogen, lower alkyl, aryl, lower alkanoyl, formyl, halogen, hydrazino nitro, $NR_2R_3$, heterocyclic lower alkyl, lower alkyl sulfonyl, $OR_1$, amino lower alkyleneoxy, monoloweralkylaminoloweralkyleneoxy, diloweralkylaminoloweralkyleneoxy, diloweralkylaminolowerlalkyleneamino, loweralkyanoylamino,

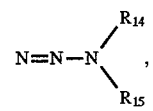

$SR_1$, cyano, $CO_2H$, $SO_2NR_1R_2$, or $CONR_1R_2$;

$R_1$ is hydrogen, lower alkyl, aryl lower alkyl, aryl, formyl or lower alkanoyl;

$R_2$ and $R_3$ are independently hydrogen, lower alkyl, aryl, aryl lower alkyl, formyl, lower alkanoyl, monoloweralkyl amino lower alkylene, diloweralkylamino lower alkylene or hydroxy lower alkyl amino;

A is $(CR_4R_5)n_3$, lower cycloalkylene or arylene or a chemical bond;

each $R_4$ and $R_5$ are independently hydrogen or lower alkyl;

$n_3$ is 0, 1, 2, 3, 4, or 5;

$R_{14}$ and $R_{15}$ are independently hydrogen or lower alkyl;

$R_{12}$ and $R_{13}$ are independently hydrogen or lower alkyl, which is unsubstituted or substituted with hydroxy, mercapto, lower alkoxy, lower alkylcarbonyloxy, carboxy, or carboloweralkoxy or $R_{12}$ and $R_{13}$ taken together with the nitrogen to which they are attached form a 3–6-membered heterocyclic ring, with said ring containing a nitrogen as a ring heteroatom and optionally a sulfur or oxygen ring heteroatom; and D is a chemical bond, or taken together with $NR_{12}$ forms a 5 or 6-membered heterocyclic ring, with said ring containing a nitrogen as a ring heteroatom and optionally a sulfur or oxygen ring heteroatom.

37. A compound of the formula:

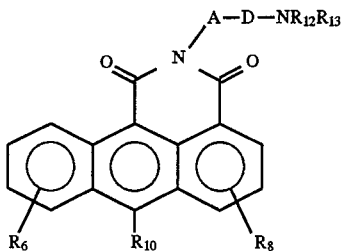

or pharmaceutically acceptable salts thereof wherein $R_{10}$ is aminoloweralkyleneoxy, monoloweralkylaminoloweralkyleneoxy, diloweralkylaminoloweralkleneoxy or

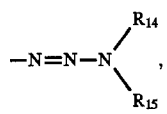

$R_6$ and $R_8$ are independently hydrogen, lower alkyl, aryl, lower alkanoyl, formyl, halogen, hydrazino, nitro, $NR_2R_3$, heterocyclic lower alkyl, lower alkylsulfonyl, $OR_1$, amino lower alkyleneoxy, monoloweralkylamino-loweralkyleneoxy, diloweralkylaminoloweralkyleneoxy, diloweralkylamino loweralkyleneamino, loweralkyanoylamino,

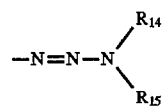

$SR_1$, cyano, $CO_2H$, $SO_2NR_1R_2$, or $CONR_1R_2$;

$R_1$ is hydrogen, lower alkyl, aryl lower alkyl, aryl, formyl or lower alkanoyl;

$R_2$ and $R_3$ are independently hydrogen, lower alkyl, aryl, aryl lower alkyl, formyl, lower alkanoyl, monoloweralkyl amino lower alkylene, diloweralkylamino lower alkylene or hydroxy lower alkyl amino;

A is $(CR_4R_5)n_3$, lower cycloalkylene or arylene or a chemical bond;

each $R_4$ and $R_5$ are independently hydrogen or lower alkyl;

$R_{14}$ and $R_{15}$ are independently hydrogen or loweralkyl;

$n_3$ is 0, 1, 2, 3, 4 or 5;

$R_{12}$ and $R_{13}$ are independently hydrogen or lower alkyl which is unsubstituted or substituted with hydroxy, mercapto, lower alkoxy, lower alkylcarbonyloxy, carboxy, or carboloweralkoxy or $R_{12}$ and $R_{13}$ taken together with the nitrogen to with they are attached form a 3–6-membered heterocyclic ring, with said ring containing a nitrogen ring heteroatom and optionally an oxygen or sulfur ring heteroatom; and D is a chemical bond, or taken together with $NR_{12}$ forms a 5 or 6-membered heterocyclic ring, said ring containing a nitrogen ring heteroatom, and optionally a sulfur or oxygen ring heteroatom.

38. The compound according to claim 35 or claim 37 wherein $R_6$ is hydrogen, amino, nitro, hydroxy, halo, sulfonamido, amino lower alkanoyl, diloweralkyltriazino, or lower alkoxy and $n_3$ is 1.

39. The compound according to claim 36 or claim 37 wherein $R_8$ is hydrogen.

40. The compound according to claim 35 or claim 37 wherein $R_6$ is hydrogen.

41. The compound according to claim 35 or claim 36 wherein $R_{10}$ is hydrogen.

42. The compound according to claim 36 wherein $R_8$ and $R_{10}$ are hydrogen.

43. The compound according to claim 36 wherein $R_8$ and $R_{10}$ are hydrogen, $R_6$ is amino lower alkanoyl (or diloweralkyltriaenyl) and $n_3$ is 1.

44. The compound according to claim 43 wherein $R_6$ is t-butylcarbonylamino or $-N=N-(CH_3)_2$.

45. The compound according to claim 37 wherein $R_8$ and $R_6$ are hydrogen.

46. The compound according to claim 35 or claim 36 wherein $R_{10}$ is hydrogen, lower alkyl, halo, hydroxy, lower alkoxy, lower alkylthio, lower alkanoylamino, diloweralkylamino lower alkylene amino, amino or aziridino lower alkylene.

47. The compound according to claim 36 or 37 in which $R_8$ is hydrogen, lower alkyl, lower alkanoylamino, diloweralkylaminoloweralkyleneoxy, loweralkanoylamino, nitro, amino, halo, diloweralkylamino lower alkylene amino, or lower alkylsulfonyl.

48. The compound according to claim 35 or claim 36 in which $R_6$ and $R_{10}$ are hydrogen.

49. The compound according to claim 35 in which $R_6$ and $R_{10}$ are hydrogen and $R_8$ is diloweralkylaminoloweralkyleneoxy.

50. The compound according to any one of claims 35, 36 or 37 wherein A is $(CR_4R_5)n_3$ and D is a chemical bond.

51. The compound according to claim 50 wherein $n_3$ is 2–4.

52. The compound according to claim 50 wherein $R_4$ and $R_5$ are independently hydrogen and $n_3$ is 2–4.

53. The compound according to any one of claims 35, 36 or 37 wherein $R_{12}$ and $R_{13}$ are hydrogen or lower alkyl unsubstituted or substituted with hydroxy.

54. The compound according to any one of claims 35, 36 or 37 wherein $R_{12}$ and $R_{13}$ are the same.

55. The compound according to any one of claims 35, 36 or 37 wherein D taken together with $NR_{12}$ form a 5 or 6-membered nitrogen containing ring.

56. The compound according to any one of claims 35, 36 or 37 wherein $ADNR_{12}R_{13}$ is

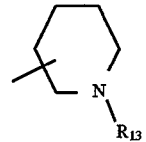

pyridyl, pyridyl lower alkylene, aziridino lower alkylene, pyrazino lower alkylene, pyrrolidyl lower alkylene, N-loweralkyl pyrrolidino lower alkylene, or morpholino lower alkylene.

57. The compound according to claim 56 in which alkylene contains 1 or 2 carbon atoms.

58. The compound according to any one of claims 35, 36 and 37 in which $ADNR_{12}R_{13}$ is $CH_2CH_2N(CH_3)_2$, piperidinoethylene, pyrrolidinoethylene, N-ethyl-3-piperidino, 2-pyridylmethylene, 3-pyridylmethylene, N-ethyl-2-pyrrolidinomethylene, N-methyl-2-pyrrolidinoethylene, 2-N-piperazinoethylene, or aziridinoethylene.

59. The compound according to claim 50 in which ADNR$_{12}$R$_{13}$ is CH$_2$CH$_2$N(CH$_3$)$_2$.

60. The compound according to claim 35 in which R$_6$ is hydrogen, R$_8$ is diloweralkylaminoloweralkyleneoxy and R$_{10}$ is hydrogen, lower alkoxy, halo or amino.

61. The compound according to claim 36 in which R$_8$ is hydrogen, chloro, hydroxy, methoxy, ethoxy, acetamido, or (CH$_3$)$_2$N(CH$_2$)$_2$NH and R$_{10}$ is hydrogen, methoxy or amino.

62. The compound according to any one of claims 35, 36 or 37 in which R$_8$ is substituted at the 6-position.

63. The compound according to claim 36 or 37 in which R$_8$ is 6-halo, 6-hydroxy, 6-lower alkoxy or 6-diloweralkyl amino lower alkylene amino.

64. The compound according to claim 63 wherein R$_8$ is 6-loweralkoxy.

65. The compound according to claim 64 wherein R$_8$ is 6-ethoxy.

66. The compound according to claim 1 which is 2-[2'-(dimethylamino)ethyl]-1,2-dihydro-3H-dibenz(deh)-isoquinoline-1,3-dione, [2'-(dimethylamino)ethyl]-1,2-dihydro-8-nitro-3 H-dibenz(deh)isoquinoline-1,3-dione, 2-[2'-(dimethylamino)ethyl]1,2-dihydro-6-ethyl-3H-dibenz (deh)isoquinoline-1,3-dione, 10-chloro-2-[2'-(dimethylamino)ethyl]-1,2-dihydro-3H-dibenz(deh) isoquinoline-1,3-dione, 2-[2'-(dimethyl-amino)ethyl]-1,2-dihydro-7-hydroxy-3H-dibenz(deh) isoquinoline-1,3-dione, 2-[2'-(dimethylamino)ethyl]-1,2-dihydro-7-methoxy-3H-dibenz(deh)isoquinoline-1,3-dione, 2-[2'-(dimethylamino)-ethyl]-1,2-dihydro-7-methyl-3H-dibenz(deh)isoquinoline-1,3-dione, or 1,2-dihydro-2-[2'-methylaminoethyl]-3H-dibenz (deh)-isoquinoline-1,3-dione.

67. The compound according to claim 1 which is 2-[2'-(N-pyrrolidino)ethyl]-1,2-dihydro-3H-dibenz(deh)-isoquinoline-1,3-dione, 2-[2'-(N-piperidino)ethyl]-1,2-dihydro-3H-dibenz(deh)isoquinoline-1,3-dione, 2-[1'-ethyl-3'-piperidinyl]-1,2-dihydro-3H-dibenz(deh)-isoquinoline-1,3-dione, 2-[3'-(bis-2-hydroxyethyl)amino-propyl]-1,2-dihydro-3H-dibenz(deh)isoquinoline-1,3-dione, 2-[3'-(dimethylamino)propyl]-1,2-dihydro-3H-dibenz(deh)-isoquinoline-1,3-dione, 2-(4'-dimethylaminophenyl)-1,2-dihydro-3H-dibenz(deh)isoquinoline-1,3-dione, 2-[2'-(dimethylamino)ethyl]-1,2-dihydro-11-nitro-3H-dibenz-(deh)isoquinoline-1,3-dione, 8-amino-2-[2'-dimethylamino-ethyl]-1,2-dihydro-3H-dibenz(deh)isoquinoline-1,3-dione, 11-amino-2-[2'-(dimethylaminoethyl)]-1,2-dihydro-3H-dibenz-(deh)isoquinoline-1,3-dione; 2-[2'-(dimethylamino) ethyl]-6-ethyl-1,2-dihydro-3H-dibenz(deh)isoquinoline-1,3-dione 8-sulfonamide, 7-chloro-2-[2'-(dimethylamino) ethyl]-1,2-dihydro-3H-dibenz-(deh)isoquinoline-1,3-dione, 2-[2'-(1 -piperazinyl)ethyl]-1,2-dihydro-3H-dibenz(deh) isoquinoline-1, 3-dione, 2-[2'-(N-morpholinyl)ethyl]-1,2-dihydro-3H-dibenz(deh)-isoquinoline-1, 3-dione, 2-[(1'-ethyl-2-pyrrolidinyl)methyl]-1,2-dihydro-3H-dibenz(deh) isoquinoline-1, 3-dione, 2-[2'-(1-methyl)-2-pyrrolidinyl) ethyl]-1,2-dihydro-3H-dibenz-(deh)isoquinoline-1, 3-dione, 2-[(2'-imidazolinyl)methyl]-1,2-dihydro-3H-dibenz(deh) isoquinoline-1, 3-dione, 2-(3'-pyridyl)-1,2-dihydro-3H-dibenz(deh)isoquinoline- 1,3-dione, 2-[2'-(2-pyridyl)ethyl]-1,2-dihydro-3H-dibenz(deh)-isoquinoline-1, 3-dione and, 2-[(1'-aziridinyl)ethyl]-1,2-dihydro-3H-dibenz(deh)-isoquinoline-1, 3-dione.

68. The compound according to claim 1 which is 4-acetamido-2-[(2'-dimethylamino)ethyl]-1,2-dihydro-3H-dibenz(deh)isoquinoline1,3-dione, 4-amino-2-[(2'-dimethyl-amino)ethyl]-1,2-dihydro-3H-dibenz(deh) isoquinoline-1,3-dione, 4-hydroxy-2-[(2'-dimethylamino) ethyl]-1,2-dihydro-3H-dibenz(deh)isoquinoline-1,3-dione, 4-methoxy-2-[(2'-dimethylamino)ethyl]-1,2-dihydro-3H-dibenz(deh)isoquinoline-1,3-dione, 4-chloro-2-[(2'-dimethylamino)ethyl]-1,2-dihydro-3H-dibenz(deh) isoquinoline-1,3-dione, 4-trifluoromethyl-2-[(2'-dimethylamino)ethyl]-1,2-dihydro-3H-dibenz(deh) isoquinoline-1,3-dione, 5-acetamido-2-[(2'-dimethylamino) ethyl]-1,2-dihydro-3H-dibenz(deh)isoquin-oline-1,3-dione, 5-amino-2-[(2'-dimethylamino)ethyl]-1,2-dihydro-3H-dibenz(deh)isoquinoline-1,3-dione, 5-methoxy-2-[(2'-dimethylamino)ethyl]-1,2-dihydro-3H-dibenz(deh) isoquinoline-1,3-dione, 5-nitro-2-[(2'-dimethylamino)ethyl] -1,2-dihydro-3H-dibenz(deh)isoquinoline- 1,3-dione, 6-acetamido-2-[(2'-dimethylamino)ethyl]-1,2-dihydro-3H-dibenz(deh)isoquinoline-1,3-dione, 6-amino-2-[(2'-dimethylamino)ethyl]-1,2-dihydro-3H-dibenz(deh) isoquinoline-1,3-dione, 6-hydroxy-2-[(2'-dimethylamino) ethyl]-1,2-dihydro-3H-dibenz(deh)isoquinoline-1,3-dione, 6-methoxy-2-[(2'-dimethylamino)ethyl]-1,2-dihydro-3H-dibenz(deh)isoquin-oline-1,3-dione, 6-chloro-2-[(2'-dimethylamino)ethyl]-1,2-dihydro-3H-dibenz(deh) isoquinoline-1,3-dione, 6-trifluoro-methyl-2-[(2'-dimethylamino)ethyl]-1,2-dihydro-3H-dibenz(deh) isoquinoline-1,3-dione, 6-nitro-2-[(2'-dimethylamino)ethyl] -1,2-dihydro-3H-dibenz(deh)isoquinoline-1,3-dione, 6-methyl-2-[(2'-dimethylamino)ethyl]-1,2-dihydro-3H-dibenz(deh)isoquinoline-1,3-dione, 7-acetamido-2-[(2'-dimethylamino)ethyl]-1,2-dihydro-3H-dibenz(deh)isoquin-oline-1,3-dione, 7-amino-2-[(2'-dimethylamino)ethyl]-1,2-dihydro-3H-dibenz(deh)isoquinoline-1,3-dione, 7-trifluoro-methyl-2-[(2'-dimethylamino)ethyl]-1,2-dihydro-3H-dibenz (deh)isoquinoline-1,3-dione, 7-methylthio-2-[(2'-dimethyl-amino)ethyl]-1,2-dihydro-3H-dibenz(deh)isoquinoline-1,3-dione, 8-acetamido-2-[(2'-dimethylamino)ethyl]-1,2-dihydro-3H-dibenz(deh)isoquinoline-1,3-dione, 8-hydroxy-2-[(2'-dimethylamino)ethyl]-1,2-dihydro-3H-dibenz(deh) isoquinoline-1,3-dione, 8-methoxy-2-[(2'-dimethylamino) ethyl]-1,2-dihydro-3H-dibenz(deh)isoquinoline-1,3-dione, 8-chloro-2-[(2'-dimethylamino)ethyl]-1,2-dihydro-3H-dibenz(deh)isoquinotine-1,3-dione, 8-trifluoromethyl-2-[ (2'-dimethylamino)ethyl]-1,2-dihydro-3H-dibenz(deh) isoquin-oline-1,3-dione, 9-acetamido-2-[(2'-dimethylamino)ethyl]-1,2-dihydro-3H-dibenz(deh) isoquinoline-1,3-dione, 9-amino-2-[(2'-dimethylamino) ethyl]-1,2-dihydro-3H-dibenz(deh)isoquinoline-1,3-dione, 9-hydroxy-2-[(2'-dimethylamino)ethyl]-1,2-dihydro-3H-dibenz(deh)isoquinoline-1,3-dione, 9-methoxy-2-[(2'-dimethylamino)ethyl]-1,2-dihydro-3H-dibenz(deh) isoquinoline-1,3-dione, 9-chloro-2-[(2'-dimethyl-amino) ethyl]-1,2-dihydro-3H-dibenz(deh)isoquinoline-1,3-dione, 9-trifluoromethyl-2-[(2'-dimethylamino)ethyl]-1,2-dihydro-3H-dibenz(deh)isoquinoline-1,3-dione, 9-nitro-2-[(2'-dimethylamino)ethyl]-1,2-dihydro-3H-dibenz(deh) isoquinoline-1,3-dione, 10-acetylamino-2-[(2'-dimethylamino)-ethyl]-1,2-dihydro-3H-dibenz(deh) isoquinoline-1,3-dione, 10-amino-2-[(2'-dimethylamino) ethyl]-1,2-dihydro-3H-dibenz(deh)isoquinoline-1,3-dione, 10-hydroxy-2-[(2'-dimethyl-amino)ethyl]-1,2-dihydro-3H-dibenz(deh)isoquinoline-1,3-dione, 10-methoxy-2-[(2'-dimethylamino)ethyl]-1,2-dihydro-3H-dibenz(deh) isoquinoline-1,3-dione, 10-trifluoromethyl-2-[(2'-dimethylamino)ethyl]-1,2-dihydro-3H-dibenz(deh) isoquinoline-1,3-dione, 10-nitro-2-[(2'-dimethylamino) ethyl]-1,2-dihydro-3H-dibenz(deh)isoquinoline-1,3-dione, 11-acetamido-2-[(2'-dimethylamino)ethyl]-1,2-dihydro-3H-dibenz(deh)isoquinoline-1,3-dione, 11-hydroxy-2-[(2'-dimethylamino)ethyl]-1,2-dihydro-3H-dibenz(deh) isoquinoline-1,3-dione, 11-methoxy-2-[(2'-dimethylamino)

ethyl]-1,2-dihydro-3H-dibenz(deh)isoquinoline-1,3-dione, or 2-[2'-(dimethylamino)ethyl]-1,2-dihydro-5-nitro-3H-dibenz(deh)isoquinoline-1,3-dione.

69. The compound according to claim 1 in which the compound is 6-chloro-2-[2'-(dimethylamino)]-1,2-dihydro-3H-dibenz(deh)isoquinoline-1,3-dione, 2-[2'-(dimethylamino)ethylamino]-1,2-dihydro-3H-dibenz(deh)isoquinoline-1,3-dione, 7-amino-2-[2'-(dimethylamino)ethyl]-1,2-dihydro-3H-dibenz(deh)isoquinoline-1,3-dione 2-[2'-(dimethylamino)ethyl]-6-hydroxy-1,2-dihydro-3H-dibenz(deh)isoquinoline-1,3-dione, 2-[2'-(dimethylamino)ethyl]-6-methoxy-1,2-dihydro-3H-dibenz(deh)isoquinoline-1,3-dione, or 2-[2'-(dimethylamino)ethyl]-7-methoxy-1,2-dihydro-3H-dibenz(deh)isoquinoline-1,3-dione.

70. The compound according to claim 1 in which the compound is 2-(3-pyridylmethyl)-1,2-dihydro-3H-dibenz(deh)isoquinoline-1,3-dione, 2-(2-pyridylmethyl)-1,2-dihydro-3H-dibenz(deh)isoquinoline-1,3-dione, 2-[2-(N-morpholinyl)ethyl]-1,2-dihydro-3H-dibenz(deh)-isoquinoline-1,3-dione, 2-[(N-ethyl-2-pyrrolidinyl)-methyl]-1,2-dihydro-3H-dibenz(deh)isoquinoline-1,3-dione, 2-[2'-(N-methyl-2-pyrrolidinyl)ethyl]-1,2-dihydro-3H-dibenz(deh)isoquinoline-1,3-dione, 2-[2-(2'-(pyridyl)ethyl]-1,2-dihydro-3H-dibenz(deh)isoquinoline-1,3-dione, 2-(3-pyridyl)-1,2-dihydro-3H-dibenz(deh)isoquinoline-1,3-dione, 2-[2-(N-piperazino)ethyl]-1,2-dihydro-3H-dibenz(deh)isoquinoline-1,3-dione, 2-[2(2-hydroxyethylamino)ethyl]-1,2-dihydro-3H-dibenz(deh)isoquinoline-1,3-dione, 2-(2-aminoethyl)-1,2-dihydro-3H-dibenz(deh)isoquinoline-1,3-dione, 2-[2-(1-aziridinyl)ethyl]-1,2-dihydro-3H-dibenz(deh)isoquinoline-1,3-dione, 2-[2-(methylamino)ethyl]-1,2-dihydro-3H-dibenz(deh)isoquinoline-1,3-dione, 4-,9-,10-acetylamino-2-[2'-(dimethylamino)ethyl]-1, 2-dihydro-3H-dibenz(deh)isoquinoline 1,3-diones, 6-acetylamino-2-[2'-(dimethylamino)ethyl]-1,2-dihydro-3H-dibenz(deh)isoquinoline-1,3-dione, 8-acetylamino-2-[2'-(dimethylamino)ethyl]-1,2-dihydro-3H-dibenz(deh)isoquinoline-1,3-dione, 11-acetylamino-2-[2'-(dimethylamino)ethyl]-1,2-dihydro-3H-dibenz(deh)isoquinoline-1,3-dione, 7-acetylamino-2-[2'-(dimethylamino)ethyl]-1,2-dihydro-3H-dibenz(deh)isoquinoline-1,3-dione, 7-chloro-2-[2'-(dimethylamino)ethyl]-1,2-dihydro-3H-dibenz(deh)isoquinoline-1,3-dione, 2-[2'-(dimethylamino)ethyl]-7-[2'-(dimethylamino)ethylamino]-1,2-dihydro-3H-dibenz(deh)-isoquinoline-1,3-dione, 10-chloro-2-[2'-(dimethylamino)ethyl]-1,2-dihydro-3H-dibenz(deh)isoquinoline-1,3-dione, 2-[2'-dimethylamino)ethyl]-10-iodo-1,2-dihydro-3H-dibenz(deh)isoquinoline-1,3-dione, 6,8-dichloro-2-[2'-(dimethylamino)ethyl]-1,2-dihydro-3H-dibenz(deh)isoquinoline-1,3-dione, 8-chloro-2-[2'-(dimethylamino)ethyl]-6-[2'-(dimethylamino)ethylamino]1, 2-dihydro-3H-dibenz(deh)isoquinoline-1,3-dione, 2-[2'-(dimethylamino)ethyl]-11-hydroxy-1,2-dihydro-3H-dibenz(deh)-isoquinoline-1,3-dione, 11-chloro-2-[2'-(dimethylamino)ethyl]-1,2-dihydro-3H-dibenz(deh)isoquinoline-1,3-dione, 8-chloro-2-[2'-(dimethylamino)ethyl]-1,2-dihydro-3H-dibenz(deh)isoquinoline-1,3-dione, 4-amino-2-[2'-(dimethylamino)ethyl]-1, 2-dihydro-3H-dibenz(deh)isoquinoline-1,3-dione, 2-[2'-(dimethylamino)ethyl]-4-trimethylacetylamino-1,2-dihydro-3H-dibenz(deh)isoquinoline-1,3-dione, 2-[2'-(dimethylamino)ethyl]-5-trimethylacetylamino-1,2-dihydro-3H-dibenz(deh)isoquinoline-1,3-dione, 6-amino-2-[2'-(dimethylamino)ethyl]-1,2-dihydro-3H-dibenz(deh)isoquinoline-1,3-dione, 2-[2'-(dimethylamino)ethyl]-6-(2'-hydroxyethylamino)-1,2-dihydro-3H-dibenz(deh)isoquinoline-1,3-dione, 2-[2'-(dimethylamino)ethyl]-6-hydrazino-1,2-dihydro-3H-dibenz(deh)isoquinoline-1,3-dione, 7-[2'-(N-ethyleneimino)ethyl]-2-[2'-(dimethylamino)ethyl]-1,2-dihydro-3H-dibenz(deh)isoquinoline-1,3-dione, 9-amino-2-[2'-(dimethylamino)ethyl]-1,2-dihydro-3H-dibenz(deh)isoquinoline-1,3-dione, 10-amino-2-[2'-(dimethylamino)ethyl]-1,2-dihydro-3H-dibenz(deh)isoquinoline-1,3-dione, 10-chloro-2-[2'-(dimethylamino)ethyl]-1,2-dihydro-3H-dibenz(deh)isoquinoline-1,3-dione, 2-[2'-(dimethylamino)-ethyl]-4-hydroxy-1,2-dihydro-3H-dibenz(deh)isoquinoline-1,3-dione, 2-[2'-(dimethylamino)ethyl]-4-methoxy-1,2-dihydro-3H-dibenz(deh)-isoquinoline-1,3-dione, 2-[2'-(dimethylamino)ethyl]-4-[2'-(dimethylamino)ethylamino]1,2-dihydro-3H-dibenz(deh)isoquinoline-1,3-dione, 2-[2'-(dimethylamino)ethyl]-7-hydroxy-1,2-dihydro-3H-dibenz(deh)isoquinoline-1,3-dione, 2-[2'-(dimethylamino)ethyl]-9-hydroxy-1,2-dihydro-3H-dibenz(deh)-isoquinoline-1,3-dione, 2-[2'-(dimethylamino)ethyl]-6-ethoxy-1,2-dihydro-3H-dibenz(deh)isoquinoline-1,3-dione, 2-[2'-(dimethylamino)ethyl]-10-hydroxy-1,2-dihydro-3H-dibenz(deh)isoquinoline-1,3-dione, 2-[2'-(dimethylamino)ethyl]-10-methoxy-1,2-dihydro-3H-dibenz(deh)isoquinoline-1,3-dione, 2-[2'-(dimethylamino)ethyl]-6-methylthio-1,2-dihydro-3H-dibenz(deh)isoquinoline-1,3-dione, 2-[2'-(dimethylamino)ethyl]-7-methylthio-1,2-dihydro-3H-dibenz(deh)isoquinoline-1,3-dione, 2-[2'-(dimethylamino)ethyl]-6-methylsulfonyl-1,2-dihydro-3H-dibenz(deh)isoquinoline-1,3-dione, 2-[2'-(dimethylamino)ethYl]-6-methyl-1,2-dihydro-3H-dibenz(deh)isoquinoline-1,3-dione, 2-[2'-(dimethylamino)ethyl]-7-methyl-1,2-dihydro-3H-dibenz(deh)isoquinoline-1,3-dione, 10-chloro-2-[2'-(methylamino)ethyl]-1,2-dihydro-3H-dibenz(deh)isoquinoline-1,3-dione, 6-chloro-2-[2'-(methylamino)ethYl]-1,2-dihydro-3H-dibenz(deh)isoquinoline-1,3-dione, 2-[2'-(methylamino)ethyl]-6-methoxy-1,2-dihydro-3H-dibenz(deh)isoquinoline-1,3-dione, or 2-(dimethylamino)-1,2-dihydro-3H-dibenz(deh)isoquinoline-1,3-dione.

71. A compound which 8-chloro-2-[2'-(dimethyl(amino)ethyl)-1,2-dihydro-3H-dibenz(deh)isoquinoline-1,3-dione, 2-[2'(dimethylamino)ethyl]-8-hydroxy-1,2-dihydro-3H-dibenz(deh)isoquinoline-1,3-dione, 2-[2'-(dimethylamino)ethyl]-10-nitro-1,2-dihydro-3H-dibenz(deh)isoquinoline-1,3-dione, 7-bromo-2-[(2'-(dimethylamino)ethyl]-1,2-dihydro-3H-dibenz(deh)isoquinoline-1,3-dione, or 9-acetylamino-2-[2'-(dimethylamino)ethyl]-1,2-dihydro-3H-dibenz(deh)isoquinoline-1,3-dione.

72. A pharmaceutical composition for the treatment of tumors comprising an anti-tumor effective amount of a compound according to claim 1 and a pharmaceutical carrier therefor.

73. A method of treating a tumor in an animal which comprises administering to an animal in need of such treatment an anti-tumor effective amount of a compound according to claim 1, said tumor being a hematological tumor or a solid tumor.

74. The compound according to claim 1 wherein $R_8$, $R_6$, and $R_{10}$ are independently hydrogen, lower alkyl, aryl, lower alkanoyl, formyl, halo, nitro, $NR_2R_3$, $OR_1$, $SR_1$, hydroxy, methoxy, cyano, $CO_2H$, $SO_2NR_1R_2$, or $CONR_1R_2$;

$R_1$, $R_2$ and $R_3$ are independently hydrogen, lower alkyl, aryl, aryl lower alkyl, formyl, or lower alkanoyl, $R_9$, $R_{11}$, $R_{10}$ and $R_7$ are independently hydrogen, or lower alkyl A is $(CR_4R_5)n_3$, lower cycloalkylene, or arylene or a chemical bond;

each $R_4$ and $R_5$ are independently hydrogen or lower alkyl, $R_{12}$ and $R_{13}$ are independently hydrogen, or lower alkyl which is unsubstituted or substituted with hydroxy, mercapto, lower alkoxy, lower alkylcarbonyloxy, carboxy or carboloweralkoxy or $R_{12}$ and $R_{13}$ taken together with the nitrogen atom to which they are attached form a 3–6 membered heterocyclic ring said ring containing nitrogen as a ring heteroatom and optionally a sulfer or oxygen ring heteroatom;

D is a chemical bond or taken together with $NR_{12}$ forms a 5- or 6-membered heterocyclic ring said ring containing a nitrogen ring heteroatom and optionally a sulfur or oxygen ring heteroatom;

$n_1$ and $n_2$ are independently 0, 1 or 2 and $n_3$ is 0, 1, 2, 3, 4, or 5.

75. The compound according to claim 74 wherein $R_6$ is hydrogen, amino, nitro, hydroxy or halo and $n_1$ is 1.

76. The compound according to claim 75 wherein $R_6$ is hydrogen, nitro or amino.

77. The compound according to claim 74 wherein A is $(CR_4R_5)n_3$ and D is a chemical bond.

78. The compound according to claim 74 wherein $n_3$ is 2–4.

79. The compound according to claim 74 wherein $R_4$ and $R_5$ are independently hydrogen.

80. A pharmaceutical composition for the treatment of a tumor comprising an anti-tumor effective amount of a compound according to any one of claims 35, 36 or 37 and a pharmaceutical carrier therefor.

81. A method of treating tumors in an animal which comprises administering to an animal in need of such treatment an anti-tumor effective amount of a compound according to any one of claims 35, 36 or 37, said tumor being a hematological tumor or a solid tumor.

82. The method according to claim 73 wherein said tumor is colon tumor, leukemia, ovarian tumor, melanoma, adenocarcinoma, lung cancer, myeloma, sarcoma, rectum cancer, or breast cancer, mitomycin C resistant tumors, adriamycin resistant tumors.

83. 6-[2-(dimethylamino)ethoxy]-2-[[2'(dimethylamino) ethyl]-1,2-dihydro-3H-dibenz (deh)isoquinoline-1,3-dione, 10-cyano-2-[2'(dimethylamino)ethyl]-1,2-dihydro-3H-dibenz (deh)isoquinoline-1,3-dione, 2-[2'(dimethylamino) ethyl]-10-dimethyltriazino-1,2-dihydro-3H-dibenz(deh) isoquinoline-1,3-dione or 2-[2'-(dimethylamino)ethyl]-10-fluoro-1,2-dihydro-3H-dibenz(deh)-isoquinoline-1,3-dione.

* * * * *

UNITED STATES PATENT AND TRADEMARK OFFICE
CERTIFICATE OF CORRECTION

PATENT NO.   : 5,635,506
DATED        : June 3, 1997
INVENTOR(S)  : D. Alberts et al.

Page 1 of 5

It is certified that error appears in the above-identified patent and that said Letters Patent is hereby corrected as shown below:

Column 1,
Line 4, add the following: "This invention was made with government support awarded by the National Institute of Health. The government has certain rights in the invention".

Column 2,
Line 46, "cytotoxtc" should read -- cytotoxic --

Column 3,
Line 15, "amino-loweralkyleneoxy" should read -- aminoloweralkyleneoxy --

Column 4,
Line 17, "In" should read -- in --

Column 6,
Line 1, "imtdazolidine" should read -- imidazolidine --
Lines 2 & 20, "piperidtne" should read -- piperidine --

Column 7,
Line 42, "alkyl" should read -- alkyl; --

Column 9,
Line 64, "of simple addition by" should read -- by simple addition of --

Column 12,
Line 4, "It" should read -- it --

Column 13,
Line 17, "dioine" should read -- dione (1) --
Line 28, "[s" should read -- (s --

Column 14,
Line 21, "CDC1 $_1$" should read -- CDC1 $_3$ --
Line 34, "mmole" should read -- mmol --
Line 43, "1.8" should read -- δ 1.8 --

Column 15,
Lines 5 & 7, "mmole" should read -- mmol --

Column 17,
Lines 53 & 56, "mmole" should read -- mmol --

UNITED STATES PATENT AND TRADEMARK OFFICE
CERTIFICATE OF CORRECTION

PATENT NO.   : 5,635,506
DATED        : June 3, 1997
INVENTOR(S)  : D. Alberts et al.

It is certified that error appears in the above-identified patent and that said Letters Patent is hereby corrected as shown below:

Column 18,
Line 27, "It had a of" should read -- It had a melting point of --
Line 64, "H-S" should read -- H-8 --

Column 19,
Line 9, "H-S" should read -- H-8 --

Column 22,
Line 8, "hexanestoluene" should read -- hexanes/toluene --
Line 47, "acetamtdooxalylanthracenes" should read -- acetamidooxalylanthracenes --
Line 59, "4-,9-" should read -- 4-, 9- --
Line 67, "mmole" should read -- mmol --
Line 67, delete "at once"

Column 23,
Line 3, delete "at once"
Line 25, "toluenemethanol" should read -- toluene/methanol --
Line 37, "13,32" should read -- 13.32 --
Line 54, "H-8.61" should read -- H-4),8.61 --

Column 24,
Line 8, after "solvent" delete -- . --

Column 25,
Line 14, "mmole" should read -- mmol --

Column 26,
Line 10, "i,3" should read -- 1,3 --
Line 23, delete " ' "
Line 36, "2,-" should read -- 2'- --
Line 66, "mmole" should read -- mmol --

Column 27,
Line 57, after "4" insert -- - --

Column 28,
Line 9, "mmole" should read -- mmol --
Line 59, "817" should read -- 8.17 --

UNITED STATES PATENT AND TRADEMARK OFFICE
CERTIFICATE OF CORRECTION

PATENT NO. : 5,635,506
DATED : June 3, 1997
INVENTOR(S) : D. Alberts et al.

It is certified that error appears in the above-identified patent and that said Letters Patent is hereby corrected as shown below:

Column 30,
Lines 19 & 20, "mmole" should read -- mmol --

Column 31,
Line 43, "sis." should read -- sis: --

Column 32,
Line 3, "2'[" should read -- 2'( --
Line 11, "S"should read -- s --
Line 16, "give melting point" should read -- give a melting point of --
Line 24, after "heated" insert -- in --
Line 64, "mmole" should read -- mmol --

Column 33,
Line 13, after "9" insert -- ' --
Lines 42 & 65, "mmole" should read -- mmol --

Column 34,
Line 23, "mmole" should read -- mmol --
Line 36, "58." should read -- 58 --

Column 36,
Line 21, "mmole" should read -- mmol --

Column 46,
Line 43, "thin layer" should read -- thin-layer --

Column 47,
Line 8, "thin layer" should read -- thin-layer --
Line 60, "105" should read -- $10^5$ --
Line 66, "uM" should read -- μM --

Column 63,
Line 36, "[Tris" should read -- [tris --

Column 65,
Line 2, "$SR_1$ , cyano" should read -- $SR_1$ ,hydroxy, methoxy, cyano --
Lines 3-5, delete "aminoloweralkyleneoxy, monoloweralkylaminoloweralkyleneoxy, diloweralkylaminoloweralkyleneoxy, $SO_2$ $NR_1$ $R_2$"
Line 34, after "with" insert -- $NR_{12}$ --

UNITED STATES PATENT AND TRADEMARK OFFICE
CERTIFICATE OF CORRECTION

PATENT NO. : 5,635,506
DATED : June 3, 1997
INVENTOR(S) : D. Alberts et al.

It is certified that error appears in the above-identified patent and that said Letters Patent is hereby corrected as shown below:

Column 66,
Line 23, "claim i" should read -- claim 1 --
Line 56, after "piperidinoethylene" insert -- , --

Column 67,
Line 64, after "hydrogen" delete -- , --

Column 68,
Line 7, after "containing" insert -- a --
Line 9, after "formula" insert -- : --
Line 32, "R $_9$" should read -- R $_8$ --

Column 70,
Line 11, "claim 36" should read -- claim 1 --
Lines 12-13, delete "(ordiloweralkyltriaenyl)"
Line 14, delete "or--N=N--(CH $_3$ )$_2$"
Line 27, "claim 36" should read -- claim 1 --

Column 71,
Line 46, "dione;" should read -- dione, --
Line 59, "and," should read -- or, --
Line 64, "isoquinoline1" should read -- isoquinoline-1 --

Column 72,
Lines 7, 19 & 41, "isoquin-oline" should read -- isoquinoline --
Line 39, "isoquinotine" should read -- isoquinoline --

Column 74,
Line 12, "i" should read -- 1 --
Lines 27 & 32, "ethYl" should read -- ethyl --
Line 37, after "which" insert -- is --

UNITED STATES PATENT AND TRADEMARK OFFICE
CERTIFICATE OF CORRECTION

PATENT NO. : 5,635,506
DATED : June 3, 1997
INVENTOR(S) : D. Alberts et al.

It is certified that error appears in the above-identified patent and that said Letters Patent is hereby corrected as shown below:

<u>Column 75,</u>
Line 1, after "hydrogen" delete -- , --

<u>Column 76,</u>
Line 16, "2-[[2" should read -- 2-[2 --

Signed and Sealed this

Twenty-eighth Day of May, 2002

*Attest:*

*Attesting Officer*

JAMES E. ROGAN
*Director of the United States Patent and Trademark Office*